(12) United States Patent
Nguyen et al.

(10) Patent No.: US 11,649,195 B2
(45) Date of Patent: May 16, 2023

(54) SMART RELEASE NITROGEN-CONTAINING FERTILIZER GRANULES

(71) Applicant: RYNAN TECHNOLOGIES PTE. LTD., Singapore (SG)

(72) Inventors: My T. Nguyen, Tra Vinh (VN); Hoa V. Tran, Tra Cu District (VN); Man M. Ly, Tran De District (VN); Van T. Kim, Tra Vinh (VN); Nhien H. Le, Can Tho (VN); Na Thach, Tra Cu District (VN); Sony T. Vo, Cang Long District (VN); Vinh Q. Nguyen, Tieu Can District (VN)

(73) Assignee: RYNAN TECHNOLOGIES PTE LTD., Singapore (SG)

( * ) Notice: Subject to any disclaimer, the term of this patent is extended or adjusted under 35 U.S.C. 154(b) by 265 days.

(21) Appl. No.: 16/967,973

(22) PCT Filed: Feb. 6, 2019

(86) PCT No.: PCT/CA2019/050155
§ 371 (c)(1),
(2) Date: Aug. 6, 2020

(87) PCT Pub. No.: WO2019/153081
PCT Pub. Date: Aug. 15, 2019

(65) Prior Publication Data
US 2021/0363073 A1    Nov. 25, 2021

Related U.S. Application Data

(60) Provisional application No. 62/628,646, filed on Feb. 9, 2018.

(51) Int. Cl.
*C05G 5/12* (2020.01)
*C05G 3/30* (2020.01)
(Continued)

(52) U.S. Cl.
CPC ............... *C05G 5/12* (2020.02); *C05F 11/10* (2013.01); *C05G 3/30* (2020.02); *C05G 3/90* (2020.02);
(Continued)

(58) Field of Classification Search
None
See application file for complete search history.

(56) References Cited

U.S. PATENT DOCUMENTS 3,502,458 A    3/1970  Schenk
4,019,890 A    4/1977  Fujita et al.
(Continued)

FOREIGN PATENT DOCUMENTS

CN    101200399 A    6/2008
CN    101875584 A    11/2010
(Continued)

OTHER PUBLICATIONS

Dong et al., "Humic acids buffer the effects of urea on soil ammonia oxidizers and potential nitrification", Soil Biol Biochem, 2009, vol. 41, No. 8, pp. 1612-1621 (22 pages total).
(Continued)

*Primary Examiner* — Wayne A Langel
(74) *Attorney, Agent, or Firm* — Sughrue Mion, PLLC

(57) ABSTRACT

There is provided a nitrogen fertilizer granule in which the nitrogen release can be timed and the nitrogen release rate can be controlled according to the needs of the plants to be fertilized. The smart release nitrogen-containing fertilizer granule comprises a nitrogen-containing fertilizer core; an organic functional layer covering the core, wherein the organic functional layer comprises at least one functional organic compound that is an enzyme inhibitor, a microbial suppressor, a phosphorus solubilizer, and/or a plant hormone; a controlled release layer covering the organic func-
(Continued)

tional layer, wherein the controlled release layer comprises water-swellable copolymeric nanoparticles; and an anticaking layer covering the controlled release layer, wherein the anticaking layer comprises water-insoluble copolymeric nanoparticles.

19 Claims, 12 Drawing Sheets

(51) Int. Cl.
  *C05G 5/30* (2020.01)
  *C05G 3/90* (2020.01)
  *C05F 11/10* (2006.01)
  *B82Y 5/00* (2011.01)
  *B82Y 30/00* (2011.01)

(52) U.S. Cl.
  CPC *C05G 5/37* (2020.02); *B82Y 5/00* (2013.01); *B82Y 30/00* (2013.01)

(56) References Cited

U.S. PATENT DOCUMENTS

| | | | |
|---|---|---|---|
| 4,657,576 A | 4/1987 | Lambie | |
| 4,851,027 A | 7/1989 | Murayama et al. | |
| 4,880,455 A | 11/1989 | Blank | |
| 5,089,041 A | 2/1992 | Thompson et al. | |
| 6,187,074 B1 | 2/2001 | von Locquenghien et al. | |
| 7,267,707 B2 | 9/2007 | Rosenthal et al. | |
| 8,764,873 B2 | 7/2014 | Nevin | |
| 2014/0328884 A1* | 11/2014 | Reyes | A61K 8/00 521/149 |
| 2015/0239790 A1 | 8/2015 | Iwig et al. | |
| 2017/0362139 A1* | 12/2017 | Zhang | C05B 17/00 |
| 2018/0343854 A1* | 12/2018 | Lillard, Jr. | C05B 17/00 |
| 2018/0346659 A1* | 12/2018 | Miller | C05D 9/02 |
| 2020/0140353 A1* | 5/2020 | Hegde | C05G 5/35 |

FOREIGN PATENT DOCUMENTS

| | | |
|---|---|---|
| CN | 102391051 A | 3/2012 |
| CN | 102653491 A | 9/2012 |
| CN | 104355874 A | 2/2015 |
| EP | 0 848 906 A1 | 6/1998 |
| JP | 9-67206 A | 3/1997 |
| JP | 11-512097 A | 10/1999 |
| WO | 97/07676 A1 | 3/1997 |

OTHER PUBLICATIONS

Sempeho et al., "Meticulous Overview on the Controlled Release Fertilizers", Advances in Chemistry, 2014, vol. 2014, Article ID 363071, pp. 1-16 (17 pages total).
Varadachari et al., "Slow-release and Controlled-release Nitrogen Fertilizers", ING Bulletins on Regional Assessment of Reactive Nitrogen, Bulletin No. 11, Jan. 2010, (Ed. Bijay Singh), SCON-ING, New Delhi, pp. i-iv & 1-42 (49 pages total).
Written Opinion for PCT/CA2019/050155, dated Apr. 29, 2019.
International Search Report for PCT/CA2019/050155, dated Apr. 29, 2019.
Tian-Lai Zhang et al., "Urea caking causes and anti-caking technique", M-sized Nitrogenous Fertilizer Progress, 2002, Issue 2, pp. 8-11 (13 pages total).
Partial Machine Translation of CN101875584A published Nov. 3, 2010 (3 pages).

* cited by examiner

SMART RELEASE NITROGEN-CONTAINING FERTILIZER GRANULES

CROSS REFERENCE TO RELATED APPLICATIONS

This application is a National Stage of International Application No. PCT/CA2019/050155 filed Feb. 6, 2019, claiming benefit, under 35 U.S.C. § 119(e), of U.S. provisional application Ser. No. 62/628,646, filed on Feb. 9, 2018.

FIELD OF THE INVENTION

The present invention relates to smart release nitrogen-containing fertilizer granules. More specifically, the present invention is concerned with nitrogen fertilizer granules in which the nitrogen release can be timed and the nitrogen release rate can be controlled according to the needs of the plants to be fertilized.

BACKGROUND OF THE INVENTION

Nitrogen-containing fertilizers, such as urea, ammonium sulfate, monoammonium phosphate, and diammonium phosphate are widely used in agriculture, especially in rice farming in Asia. However, over 50% of the nitrogen applied via conventional fertilizers is lost due to leaching, water run-off, soil immobilization, and volatilization of ammonia and nitrous oxide gases. Indeed, nitrogen fertilizers added to the soil are readily transformed through a number of undesirable biological and chemical processes, including nitrification, leaching, and evaporation. Many of these transformation processes reduce the level of nitrogen available for uptake by the targeted plant.

One such process is nitrification, a process by which certain widely occurring soil bacteria metabolize the ammonium form of nitrogen in the soil, transforming the nitrogen into nitrite and nitrate forms of nitrogen, which are more susceptible to loss from the soil through leaching or volatilization. The decrease in available nitrogen due to nitrification necessitates the addition of more nitrogen-rich fertilizer to compensate for the loss of agriculturally active nitrogen available to the plants. These concerns intensify the demand for improved management of nitrogen, in order to reduce costs associated with the use of additional nitrogen fertilizer. Methods for reducing nitrification include treating soil with agriculturally active compounds that inhibit or at least reduce the metabolic activity of at least some of the bacteria in the soil that contribute to nitrification. These compounds are called nitrification inhibitors.

The most widely used and agriculturally important nitrogen fertilizer is urea. After application of urea to soil, it is readily hydrolyzed to yield ammonia and carbon dioxide. This process is catalyzed by the enzyme urease, which is produced by some bacteria and fungi that may be present in the soil. The gaseous products formed by the hydrolysis reaction (i.e., ammonia and carbon dioxide) can volatilize to the atmosphere and thus, substantial losses from the total amount of the nitrogen applied to the soil can occur. Attempts to reduce losses of applied nitrogen have utilized urease inhibitors, which are compounds capable of inhibiting the catalytic activity of the urease enzyme on urea in the soil, as additives to the fertilizer.

Urea granules coated with humus, chitosan, N-(n-butyl) thiophosphoric triamide, or dicyandiamide are commercially available and have been proven to increase fertilizer use efficiency in farming due to the inhibition of the urease and nitrification processes. However, these products find limited use in lowland rice cultivation due to their high water solubility. Indeed, in traditional rice farming in Vietnam and other Asian countries, rice paddy fields are continuously flooded with water. Because of nitrogen fertilizer losses, to meet the nitrogen requirements of the rice plants, farmers must apply nitrogen-containing fertilizers three to five times per harvest season, which increases production costs (including labor, transportation, etc.) In addition, urea granules coated with the humus, chitosan, N-(n-butyl)thiophosphoric triamide, or dicyandiamide strongly absorb moisture. As a result, they tend to stick together, which makes them unsuitable for use with fertilizer applicators.

Nitrogen-containing fertilizers bearing various coatings are known—see U.S. Pat. Nos. 4,019,890; 4,657,576; 4,851,027; 4,880,455; and 6,187,074 as well as Chinese patents CN101875584 and CN104355874.

SUMMARY OF THE INVENTION

In accordance with the present invention, there is provided:

1. A nitrogen-containing fertilizer granule comprising:
   a nitrogen-containing fertilizer core;
   an organic functional layer covering the core, wherein the organic functional layer comprises at least one functional organic compound that is an enzyme inhibitor, a microbial suppressor, a phosphorus solubilizer, and/or a plant hormone;
   a controlled release layer covering the organic functional layer, wherein the controlled release layer comprises water-swellable copolymeric nanoparticles; and
   an anticaking layer covering the controlled release layer, wherein the anticaking layer comprises water-insoluble copolymeric nanoparticles.
2. The fertilizer granule of item 1, wherein the nitrogen-containing fertilizer is urea and or a water-soluble ammonium salt, such as an ammonium sulfate, an ammonium phosphate, or an ammonium nitrate.
3. The fertilizer granule of item 1 or 2, wherein the nitrogen-containing fertilizer is urea, ammonium nitrate, calcium ammonium nitrate, ammonium sulfate, monoammonium phosphate, diammonium phosphate, or triammonium phosphate, preferably urea, ammonium nitrate, ammonium sulfate, monoammonium phosphate, diammonium phosphate, or triammonium phosphate, and more preferably urea or diammonium phosphate.
4. The fertilizer granule of any one of items 1 to 3, wherein the core is a conventional nitrogen-containing fertilizer granule.
5. The fertilizer granule of any one of items 1 to 4, wherein the core ranges from about 1.0 to about 5.0 mm in size.
6. The fertilizer granule of any one of items 1 to 5, wherein the organic functional layer comprises two or more functional organic compounds.
7. The fertilizer granule of any one of items 1 to 6, wherein the microbial suppressor is a nitrification inhibitor.
8. The fertilizer granule of item 7, wherein the nitrification inhibitor is dicyandiamide, 2-chloro-6-(trichloromethyl) pyridine, 5-ethoxy-3-trichloromethyl-1,2,4-thiadiazole, 2-amino-3-chloro-6-methylpyridine, 2-mercaptobezothiazole, 2-sulfanimalamidothiazole, or a combination thereof.
9. The fertilizer granule of item 7 or 8, wherein the nitrification inhibitor is dicyandiamide.

10. The fertilizer granule of any one of items 1 to 9, wherein the phosphorus solubilizer is an organic acid or a salt thereof.
11. The fertilizer granule of any one of items 1 to 10, wherein the phosphorus solubilizer is citric acid, lauric acid, alkyl sulfuric acid, wherein the alkyl group is preferably a linear or branched alkyl chain with 4 to 24 carbon atoms, oxalic acid, or gluconic acid or a salt thereof.
12. The fertilizer granule of any one of items 1 to 11, wherein the phosphorus solubilizer is citric acid, gluconic acid, or oxalic acid, or a salt thereof, or an alkyl sulfuric acid salt.
13. The fertilizer granule of item 11 or 12, wherein the alkyl sulfuric acid is lauryl sulfuric acid.
14. The fertilizer granule of any one of items 11 to 13, wherein the salt is an alkali salt, and preferably a sodium salt or a potassium salt.
15. The fertilizer granule of any one of items 1 to 14, wherein the phosphorus solubilizer is an alkyl sulfuric acid salt, preferably sodium alkyl sulfate or potassium alkyl sulfate.
16. The fertilizer granule of any one of items 1 to 15, wherein the plant hormone is a plant growth hormone or a plant immune hormone.
17. The fertilizer granule of any one of items 1 to 16, wherein the plant hormone is abscisic acid; an auxin; a gibberellin; gluconic acid, salicylic acid; jasmonic acid; oxalic acid; citric acid; or pipecolic acid.
18. The fertilizer granule of item 17, wherein the auxin is a native auxin, preferably indole-3-acetic acid, 4-chlorindole-3-acetic acid, 2-phenylacetic acid, indole-3-butanoic acid, or indole-3-propanoic acid, or a synthetic auxin, preferably 1-naphthaleneacetic acid, 2,4,5-trichlorophenoxyacetic acid, 2,4-dichlorophenoxyacetic acid, 4-chlorophenoxyacetic acid, 2-methoxy-3,6-dichlorobenzoic acid, 4-nitrobenzoic acid, 2-hydroxybenzoic acid, 4-chlorobenzoic acid, 2,4-dichlorobenzoic acid, 2,4,5,-trichlorobenzoic acid, or 4-amino-3,5,6-trichloropicolinic acid.
19. The fertilizer granule of item 17 or 18, wherein the gibberellin is GA1, gibberellic acid (GA3), GA4, GA5, GA6, GA7, or GA13, preferably gibberellic acid.
20. The fertilizer granule of any one of items 1 to 19, wherein the plant hormone is 4-chlorophenyloxy acetic acid, indole-3-acetic acid, gibberellic acid, 1-naphthalene acetic acid, 4-nitrobenzoic acid, salicylic acid or a combination thereof.
21. The fertilizer granule of any one of items 1 to 20, wherein the enzyme inhibitor is an urease inhibitor.
22. The fertilizer granule of item 21, wherein the urease inhibitor is:
chitosan,
humic acids, for example provided in the form of humus,
fulvic acids,
a polyphenol, unsubstituted or substituted,
saponin,
N-(n-butyl)thiophosphoric triamide,
phenylphosphorodiamidate,
acetohydroxamic acid,
alkyl hydroxamic acid,
trans-cinnamoyl hydroxamic acid,
benzohydroxamic acid, or
hydroxamic acid,
or a combination thereof.
23. The fertilizer granule of item 21 or 22, wherein the urease inhibitors is humic acids in the form of humus, chitosan, N-(n-butyl)thiophosphoric triamide, phenylphosphorodiamidate, or an unsubstituted or substituted polyphenol, preferably an unsubstituted or substituted polyphenol, more preferably unsubstituted or substituted tannic acid, and most preferably substituted tannic acid.
24. The fertilizer granule of item 22 or 23, wherein the polyphenol is a substituted polyphenol.
25. The fertilizer granule of item 24, wherein the polyphenol bears one or more, preferably two or more, more preferably five substituents.
26. The fertilizer granule of item 25, wherein one or more, preferably two or more, and more preferably five hydroxy groups of the polyphenol are replaced by —OR$^1$ groups, in which R$^1$ is said substituent.
27. The fertilizer granule of item 25 or 26, wherein the polyphenol is substituted tannic acid.
28. The fertilizer granule of item 27, wherein one terminal hydroxy group on each of the five phenolic branches of the tannic acid is replaced by a —OR$^1$ group, in which R$^1$ is said substituent.
29. The fertilizer granule of any one of items 25 to 28, wherein said substituent comprises afunctional group bearing negative or positive charge and an oppositely charged counterion.
30. The fertilizer granule of item 29, wherein the functional group a bearing negative or positive charge is carboxylate, sulfonate, ammonium, alkyl ammonium, or dialkyl ammonium, wherein the alkyl is preferably a $C_{1-6}$ alkyl.
31. The fertilizer granule of item 29 or 30, wherein the functional groups bearing negative or positive charge is attached to the polyphenol directly or indirectly via a linking group, preferably indirectly via a linking group.
32. The fertilizer granule of item 31, wherein the linking group is an alkylene group, preferably comprising between 1 and 6 carbon atoms, and more preferably comprising between 1 and 4 carbon atoms.
33. The fertilizer granule of items 31 or 32, wherein the functional group and linking group together form:
acetate,
butyl sulfonate, or
ethyl ammonium.
34. The fertilizer granule of any one of items 29 to 33, wherein the oppositely charged counterion is a metal cation or a carboxylate or sulfonate anion of an organic acid that is a microbial suppressor, a phosphorus solubilizer, and/or a plant hormone, preferably a plant hormone.
35. The fertilizer granule of item 34, wherein the metal cation is alkali cation, preferably K$^+$.
36. The fertilizer granule of item 34 or 35, wherein the organic acid that is an enzyme inhibitor is one of the organic acids listed in item 22 or 23.
37. The fertilizer granule of any one of items 34 to 36, wherein the organic acid that is a phosphorus solubilizer is one of the organic acids listed in any one of items 11 to 13.
38. The fertilizer granule of any one of items 34 to 37, wherein the organic acid that is a plant hormone is one of the organic acids listed in any one of items 17 to 20.
39. The fertilizer granule of any one of items 34 to 38, wherein the carboxylate or sulfonate anion of the organic acid that is a microbial suppressor, a phosphorus solubilizer, and/or a plant hormone is a carboxylate anion of gibberellic acid, 1-napthanlene acetic acid, or 4-nitrobenzoic acid.
40. The fertilizer granule of any one of items 25 to 39, wherein said substituent is:
acetic acid potassium salt,
butyl sulfonic acid potassium salt, ethyl ammonium gibberellic acid salt,
ethyl ammonium 1-napthanlene acetic acid salt, or
ethyl ammonium 4-nitrobenzoic acid salt.
41. The fertilizer granule of any one of items 23 to 40, wherein the substituted tannic acid has the following ideal chemical structure:
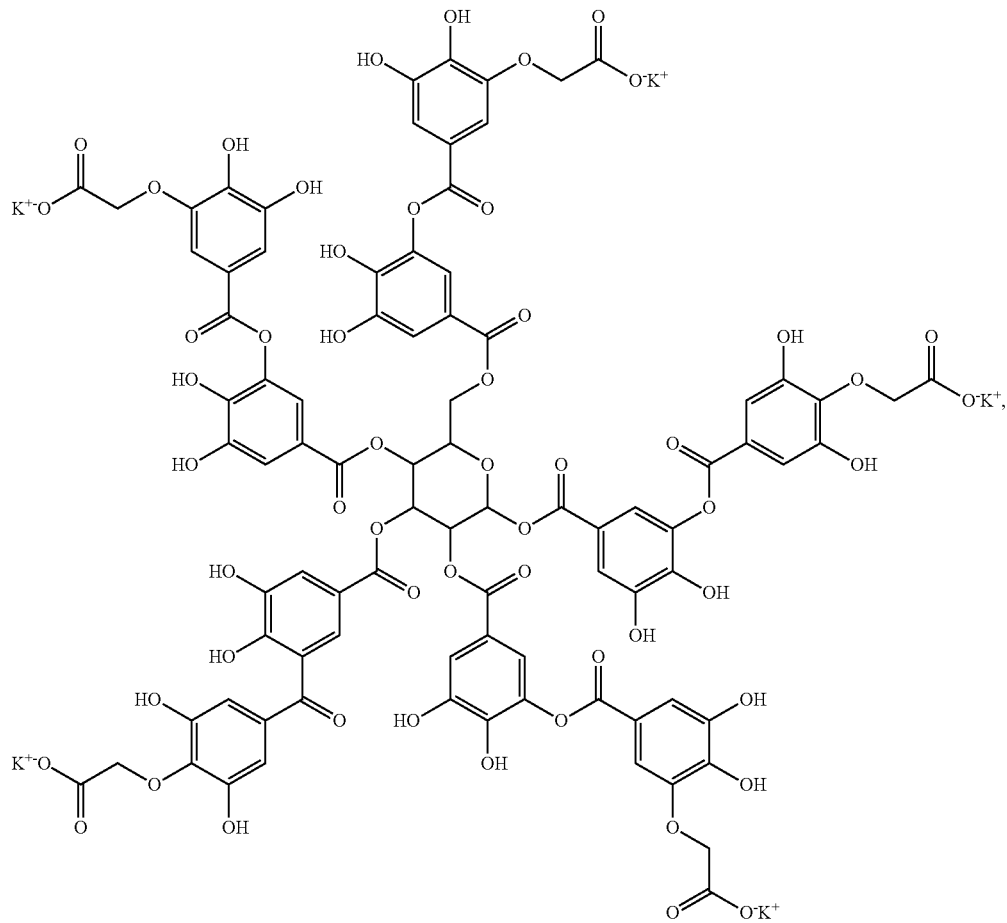
Tannic acid substituted with acetic acid potassium salt (TAAA)

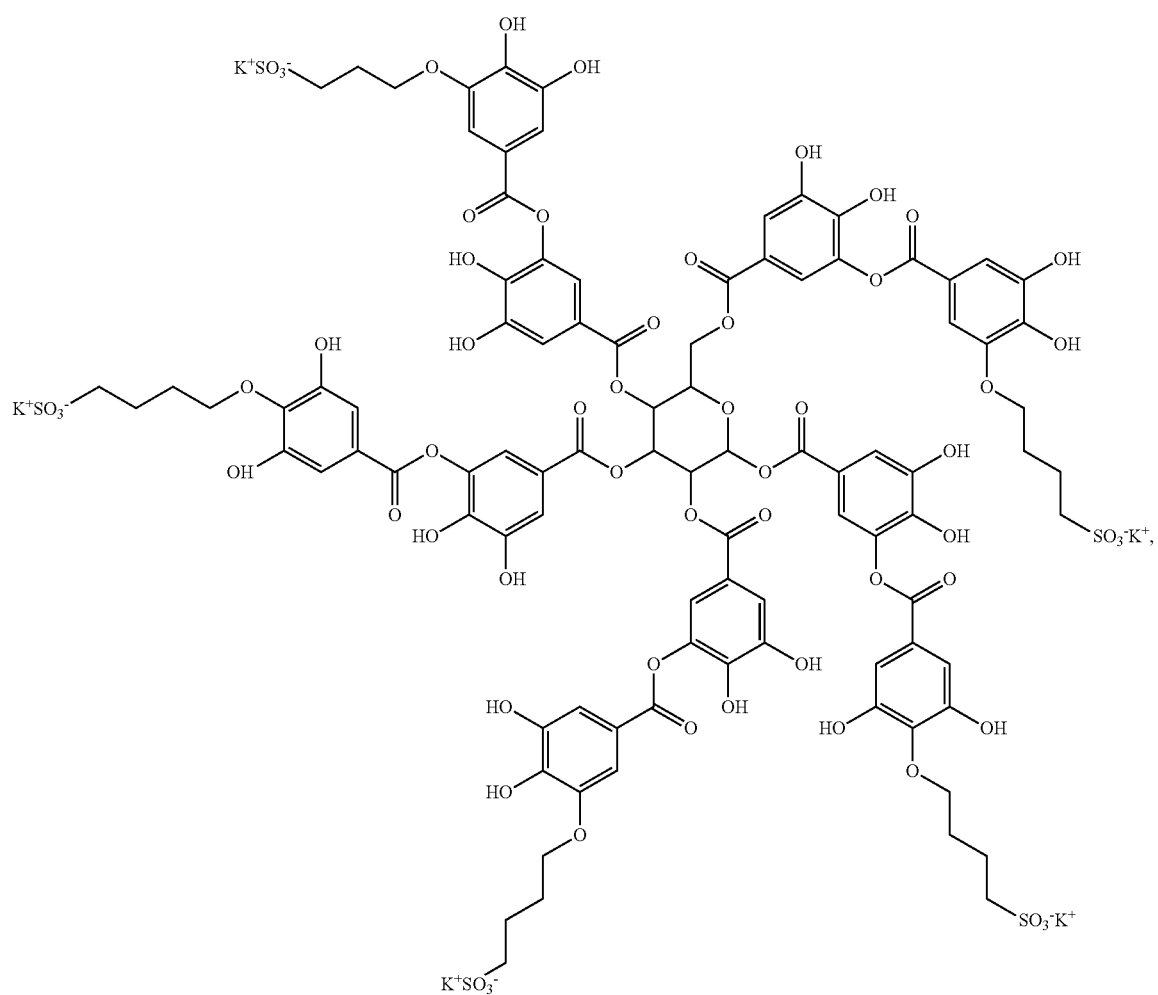
Tannic acid substituted with butyl sulfonic acid potassium salt (TABS)

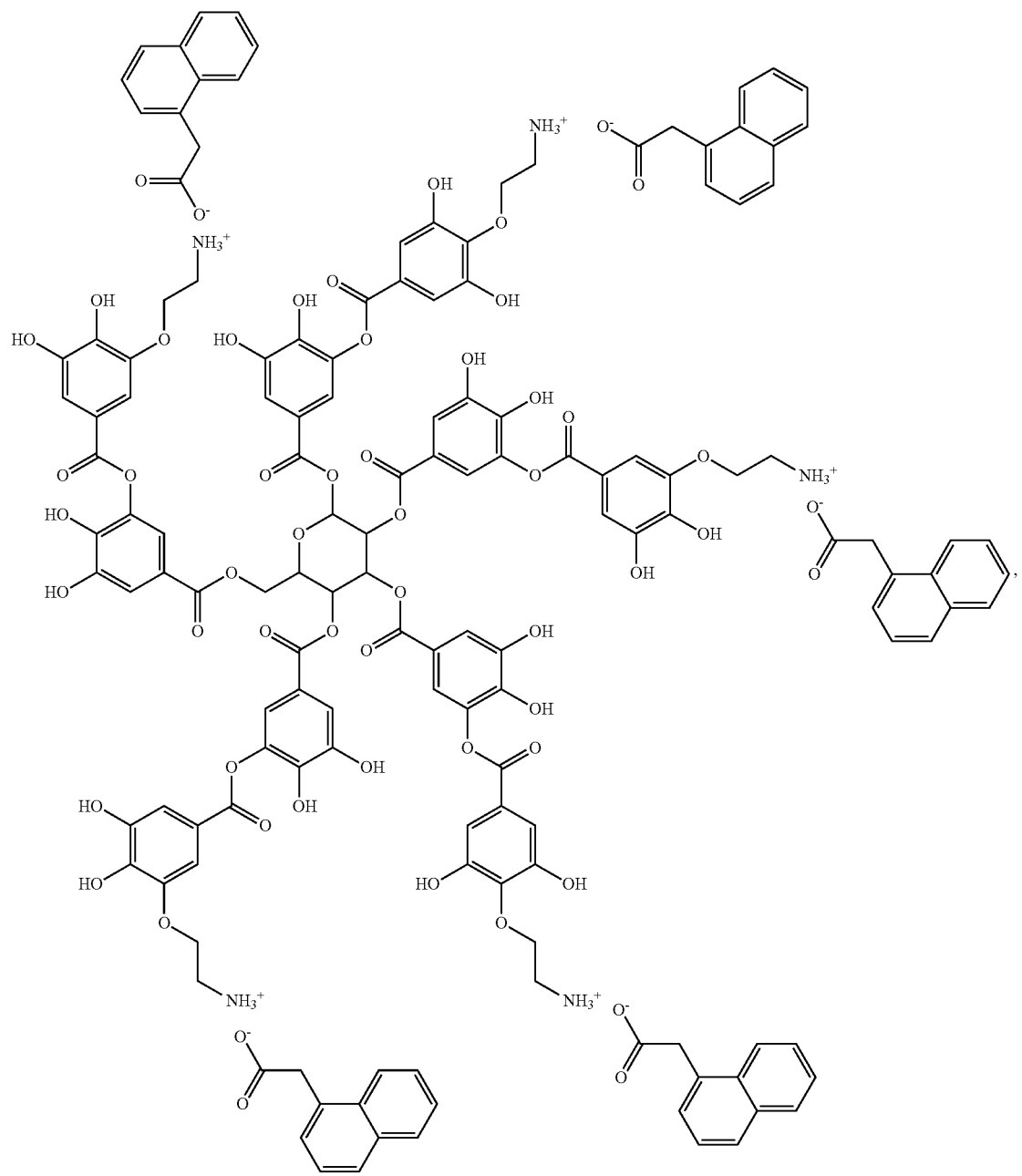
Tannic acid substituted with ethyl ammonium 1-napthanlene acetic acid salt (TANAA)

-continued
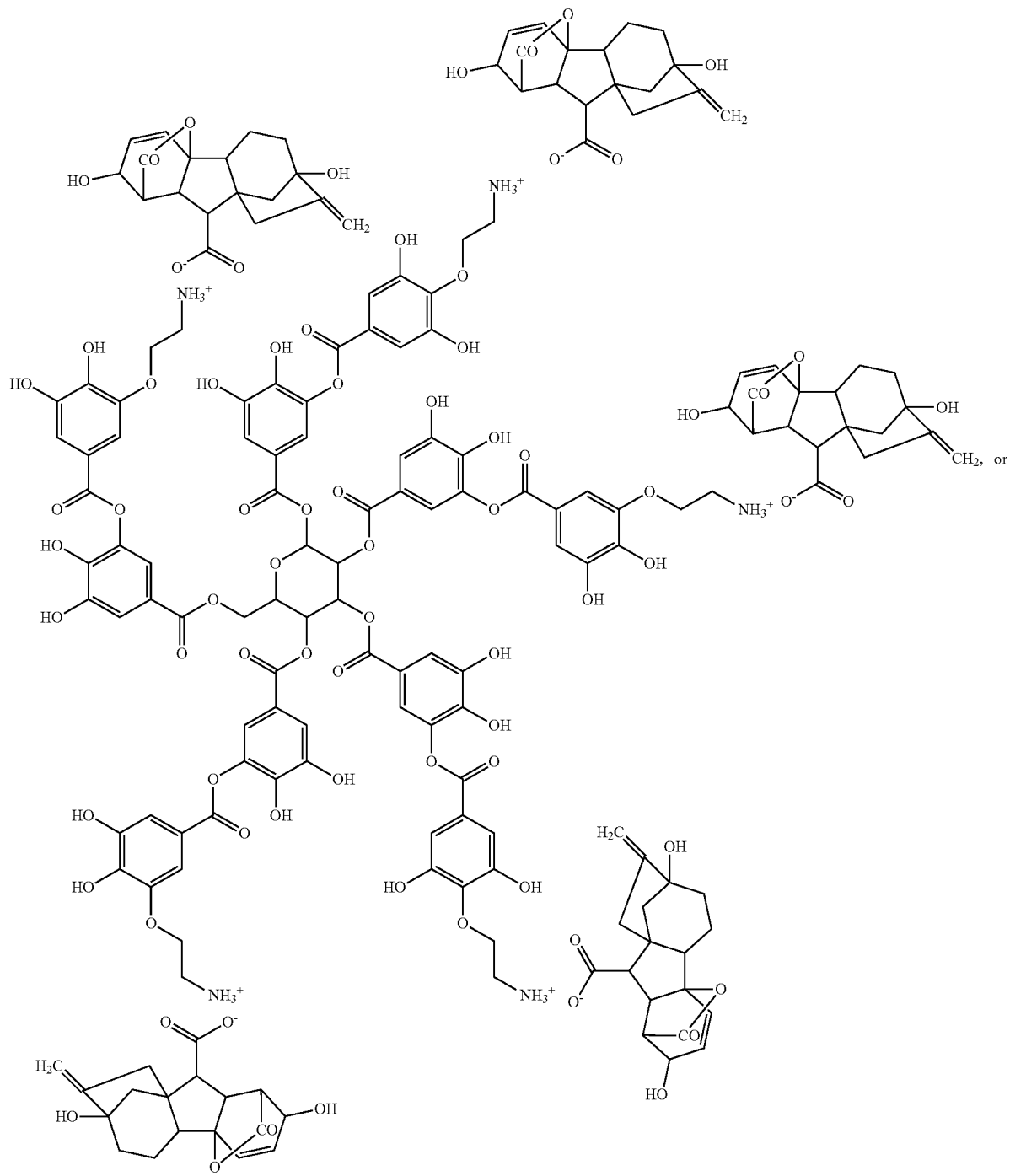
Tannic acid substituted with ethyl ammonium gibberellic acid salt (TAGA)

-continued

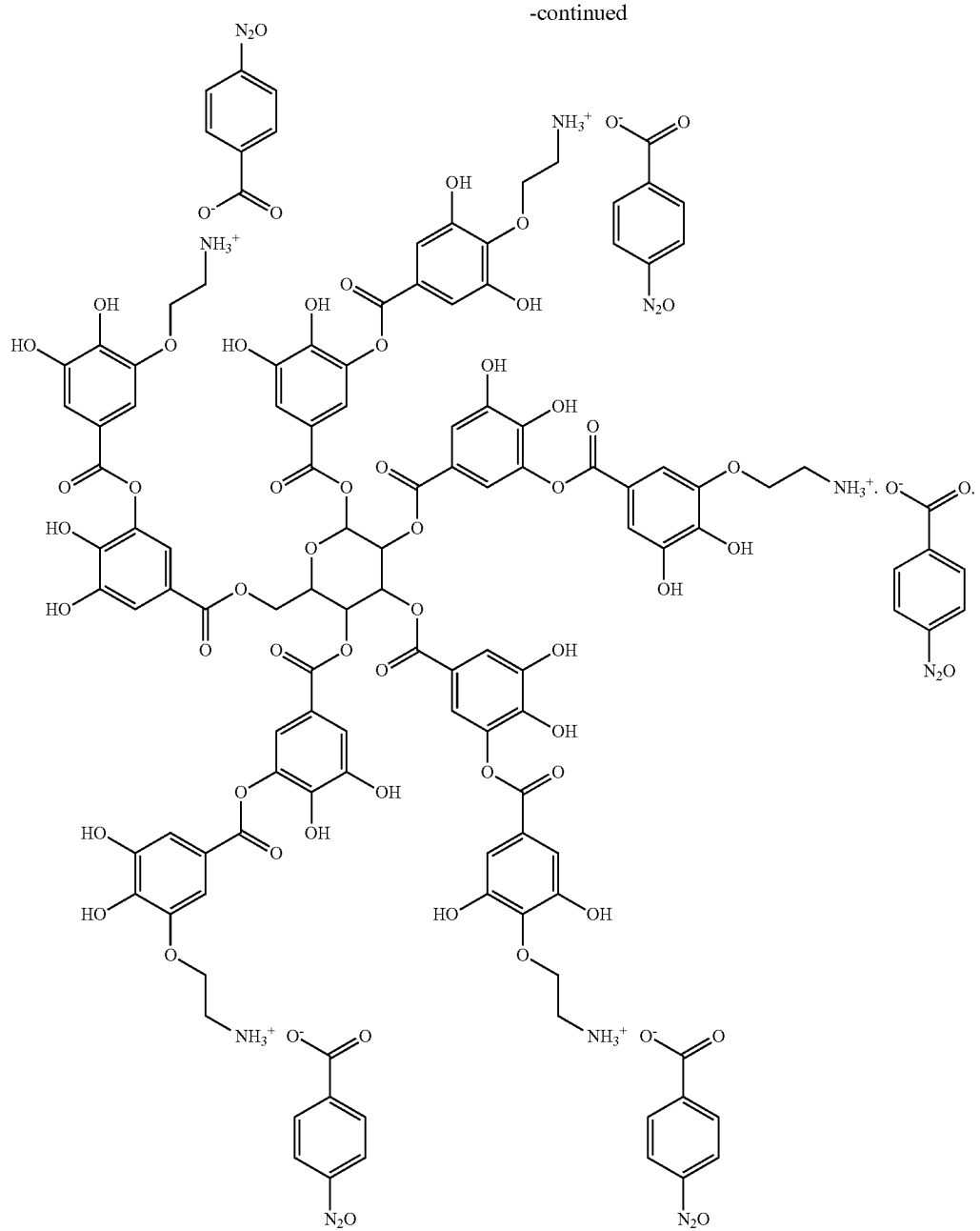

Tannic acid substituted with ethyl ammonium 4-nitrobenzoic acid salt (TABA)

42. The fertilizer granule of item 22 or 23, wherein the polyphenol is unsubstituted.
43. The fertilizer granule of any one of items 22, 23, or 42, wherein the polyphenol is unsubstituted tannic acid.
44. The fertilizer granule of any one of items 1 to 43, wherein the organic functional comprises about 40 wt % or more, about 50 wt % or more, about 60 wt % or more, about 70 wt % or more, about 80 wt % or more, or about 90 wt % or more; and/or about 100 wt % or less, about 90 wt % or less, about 80 wt % or less, about 70 wt % or less, or about 60 wt % or less of the functional organic compounds (in total), based on the weight of the organic functional layer.
45. The fertilizer granule of any one of items 1 to 44, wherein the organic functional layer comprises about 50 wt %, 64 wt %, or 100 wt % of the functional organic compounds (in total), based on the weight of the extended release layer.
46. The fertilizer granule of any one of items 1 to 45, wherein the organic functional layer further comprises a water-soluble, water-swellable, or water-dispersible polymeric binder, preferably a water-swellable polymeric binder.
47. The fertilizer granule of item 46, wherein the organic functional layer comprises about 0 wt % or more, about 10 wt % or more, about 20 wt % or more, about 30 wt % or more, about 40 wt % or more, or about 50 wt % or; and/or about 60 wt % or less, about 50 wt % or less, about 40 wt % or less, about 30 wt % or less, about 20 wt %, or about 10 wt % or less of the polymeric binder, based on the weight of the organic functional layer.
48. The fertilizer granule of item 46 or 47, wherein the organic functional layer comprises about 0 wt %, 33 wt %, or 50 wt % of the polymeric binder based on the weight of the organic functional layer.
49. The fertilizer granule of any one of items 46 to 48, wherein the polymeric binder is in the form of water-swellable copolymeric nanoparticles.
50. The fertilizer granule of item 49, wherein the copolymer making the water-swellable copolymeric nanoparticles comprises crosslinkable repeat units.
51. The fertilizer granule of item 49 or 50, wherein the glass transition temperature of the copolymer, before crosslinking if any, ranges between about 18° C. and about 25° C.
52. The fertilizer granule of any one of items 49 to 51, wherein the copolymer making the water-swellable copolymeric nanoparticles is of formula (I):

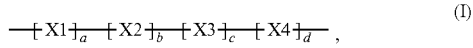     (I)

wherein:
X1 represents styrene repeat units;
X2 represents alkyl acrylate or alkyl methacrylate repeat units;
X3 represents alkoxy dialkyl vinylsilane, dialkoxy alkyl vinylsilane, or trialkoxy vinylsilane repeat units;
X4 represents acrylic acid, methacrylic acid, acrylamide, methacrylamide, vinyl phosphoric acid, or N,N-dimethylaminoethyl methacrylamide repeat units; and
a, b, c and d represent the weight percent of repeat units X1, X2, X3, and X4, respectively, based on the total weight of the copolymer, and each vary between about 0.5 wt % and about 50 wt %, and
wherein the X3 repeat units are optionally crosslinked with each other within the nanoparticles.
53. The fertilizer granule of item 52, wherein some of the X3 repeat units are crosslinked with each other within the nanoparticles.
54. The fertilizer granule of item 52 or 53, wherein up to about 3% of the X3 repeat unit are crosslinked with each other within the nanoparticles.
55. The fertilizer granule of any one of items 52 to 54, wherein the alkyl group of the alkyl acrylate or alkyl methacrylate repeat unit is butyl.
56. The fertilizer granule of any one of items 52 to 55, wherein X2 represents alkyl acrylate, preferably butyl acrylate.
57. The fertilizer granule of any one of items 52 to 56, wherein the alkoxy group of the alkoxy dialkyl vinylsilane, dialkoxy alkyl vinylsilane, or trialkoxy vinylsilane repeat units is ethoxy.
58. The fertilizer granule of any one of items 52 to 57, wherein X3 represents trialkoxy vinylsilane, preferably triethoxy vinylsilane repeat units.
59. The fertilizer granule of any one of items 52 to 58, wherein X4 represents acrylic acid, acrylamide, or vinyl phosphoric acid repeat units.
60. The fertilizer granule of any one of items 52 to 59, wherein a is about 25 wt % or more, about 35 wt % or more, about 40 wt % or more, or about 45 wt % or more; and/or about 75 wt % or less, about 65 wt % or less, about 60 wt % or less, about 55 wt % or less, or about 50 wt % or less.
61. The fertilizer granule of any one of items 52 to 60, wherein a is about 48 wt %.
62. The fertilizer granule of any one of items 52 to 61, wherein b is about 25 wt % or more, about 35 wt % or more, about 40 wt % or more, or about 45 wt % or more; and/or about 75 wt % or less, about 65 wt % or less, about 60 wt % or less, about 55 wt % or less, or about 50 wt % or less.
63. The fertilizer granule of any one of items 52 to 62, wherein b is about 48 wt %.
64. The fertilizer granule of any one of items 52 to 63, wherein c is about 0.5 wt % or more, about 1 wt % or more, about 1.5 wt % or more, about 2 wt % or more, about 2.5 wt % or more; and/or about 15 wt % or less, about 10 wt % or less, about 7.5 wt % or less, about 5 wt % or less, about 4 wt % or less, or about 3.5 wt % or less.
65. The fertilizer granule of any one of items 52 to 64, wherein c is about 3 wt %.
66. The fertilizer granule of any one of items 52 to 65, wherein d is about 0.5 wt % or more, about 0.6 wt % or more, about 0.7 wt % or more, about 0.8 wt % or more, about 0.9 wt % or more; and/or about 10 wt % or less, about 5 wt % or less, about 3 wt % or less, about 2 wt % or less, or about 1.5 wt % or less.
67. The fertilizer granule of any one of items 52 to 69, wherein d is about 1 wt %.
68. The fertilizer granule of any one of items 51 to 67, wherein the copolymer making the water-swellable copolymeric nanoparticles has the following ideal chemical structure:

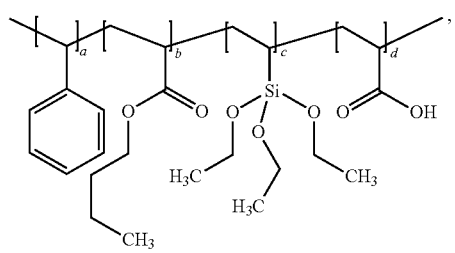

POLY-001

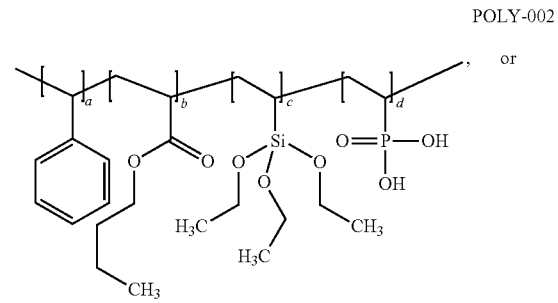

POLY-002, or

POLY-003

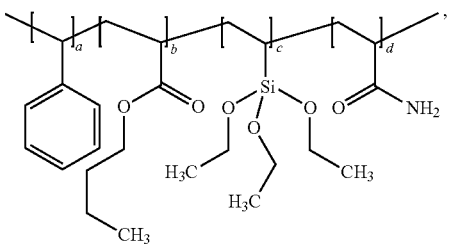

preferably POLY-001, preferably wherein a, b, c and d are about 48 wt %, about 48 wt %, about 3 wt % and about 1 wt %, respectively, based on the total weight of the copolymer.
69. The fertilizer granule of any one of items 1 to 68, wherein the organic functional layer has a coating weight between about 0.1 wt % and about 10 wt %, preferably between about 0.1 wt % and about 7 wt %, and more preferably between about 0.1 wt % and about 4.0 wt %, based on the weight of the nitrogen-containing fertilizer core.
70. The fertilizer granule of any one of items 1 to 69, wherein the controlled release layer has a coating weight between about 2 wt % and about 10 wt %, preferably between about 4 wt % and about 20 wt %, and more preferably between about 5 wt % and about 15 wt %, based on the weight of the nitrogen-containing fertilizer core.
71. The fertilizer granule of any one of items 1 to 70, wherein the controlled release layer has a larger coating weight than the organic functional layer.
72. The fertilizer granule of any one of items 1 to 71, wherein the copolymer making the water-swellable copolymeric nanoparticles of the controlled release layer comprise crosslinkable repeat units, that undergo crosslinking, with or without crosslinking agents, upon drying of the controlled release layer.
73. The fertilizer granule of any one of items 1 to 72, wherein the glass transition temperature of the copolymer making the water-swellable copolymeric nanoparticles of the controlled release layer, before crosslinking if any, ranges between about 18° C. and about 25° C.
74. The fertilizer granule of any one of items 1 to 73, wherein the copolymer making the water-swellable copolymeric nanoparticles of the controlled release layer is a copolymer as defined in any one of items 48 to 64.
75. The fertilizer granule of any one of items 1 to 74, wherein the anticaking layer has a coating weight between about 1 wt % and about 10 wt %, preferably between about 2 wt % and about 5 wt %, based on the weight of the nitrogen-containing fertilizer core.
76. The fertilizer granule of any one of items 1 to 75, wherein the glass transition temperature of the copolymer making the water-insoluble copolymeric nanoparticles ranges between about 35° C. and about 55° C.
77. The fertilizer granule of any one of items 1 to 76, wherein the copolymer making the water-insoluble copolymeric nanoparticles optionally comprises, preferably does comprise, repeat units having a plant hormone or a phosphorus solubilizer covalently or ionically attached as a pendant group.
78. The fertilizer granule of item 77, wherein the plant hormone or phosphorus solubilizer that is covalently or ionically attached as a pendant group to the copolymer making the water-insoluble copolymeric nanoparticles is:
a residue of an organic acid that is a plant hormone or phosphorus solubilizer or
a carboxylate anion of an organic acid that is a plant hormone or phosphorus solubilizer.
79. The fertilizer granule of item 77 or 78, wherein the plant hormone or phosphorus solubilizer is covalently attached as a pendant group to the copolymer making the water-insoluble copolymeric nanoparticles and is a residue of an organic acid that is a plant hormone or phosphorus solubilizer.
80. The fertilizer granule of any one of items 77 or 78, wherein the plant hormone or phosphorus solubilizer is ionically attached as a pendant group to the copolymer making the water-insoluble copolymeric nanoparticles and is a carboxylate anion of an organic acid that is a plant hormone or phosphorus solubilizer.
81. The fertilizer granule of any one of items 78 to 80, wherein the organic acid that is a plant hormone or phosphorus solubilizer is a phosphorus solubilizer.
82. The fertilizer granule of any one of items 78 to 81, wherein the organic acid that is a phosphorus solubilizer is one of the organic acids listed in any one of items 11 to 13.
83. The fertilizer granule of any one of items 78 to 80, wherein the organic acid that is a plant hormone or phosphorus solubilizer is a plant hormone.
84. The fertilizer granule of any one of items 78 to 80 and 83, wherein the organic acid that is a plant hormone is one of the organic acids listed in any one of items 17 to 20.
85. The fertilizer granule of any one of items 78 to 84, wherein the organic acid that is a plant hormone or phosphorus solubilizer is:
1-naphthalene acetic acid, 2,4,5-trichlorobenzoic acid, 2,4,5-trichlorophenoxyacetic acid, 2,4-dichlorobenzoic acid, 2,4-dichlorophenoxyacetic acid, 2-hydroxybenzoic acid, 4-chlorobenzoic acid, 4-chlorophenoxyacetic acid, 4-nitrobenzoic acid, abscisic acid, citric acid, gibberellic acid, gibberellin A13, gibberellin A3, gibberellin A4, gluconic acid, indole-3-acetic acid, indole-3-butanoic acid, oxalic acid, or salicylic acid;
preferably 1-naphthalene acetic acid, 4-chlorophenoxyacetic acid, abscisic acid, citric acid, gibberellic acid, gibberellin A3, gluconic acid, indole-3-acetic acid, indole-3-butanoic acid, oxalic acid, or salicylic acid;
more preferably 1-naphthalene acetic acid, 4-chlorophenoxyacetic acid, 4-nitrobenzoic acid, gibberellic acid, gibberellin A3, gluconic acid, indole-3-acetic acid, oxalic acid, salicylic acid, or citric acid; and
most preferably 1-naphthalene acetic acid or gibberellic acid.
86. The fertilizer granule of any one of items 77 to 85, wherein the copolymer making the water-insoluble copolymeric nanoparticles is of formula (II):

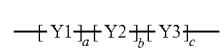 (II)

wherein:
Y1 represents styrene repeat units;
Y2 represents alkyl acrylate or alkyl methacrylate repeat units;

Y3 represents repeat units comprising, as a pendant group, an ionically or covalently attached said plant hormone or said phosphorus solubilizer;

a and b represents the weight percent of repeat units Y1 and Y2, respectively, based on the total weight of the copolymer, and vary between about 10 wt % to about 95 wt %; and c represents the weight percent of repeat units Y3, based on the total weight of the copolymer, and vary between 0 wt % to about 30 wt %.

87. The fertilizer granule of item 86, wherein Y2 represents alkyl acrylate, preferably butyl acrylate.

88. The fertilizer granule of item 86 or 87, wherein a is about 20 wt % or more, about 25 wt % or more, about 30 wt % or more, about 35 wt % or more, about 39 wt % or more, or about 40 wt % or more; and/or about 65 wt % or less, about 60 wt % or less, about 55 wt % or less, about 50 wt % or less, about 46 wt % or less, or about 45 wt % or less.

89. The fertilizer granule of any one of items 86 to 88, wherein, when c is zero, a is about 50 wt %.

90. The fertilizer granule of any one of items 86 to 89, wherein when c is greater than zero, a is between about 35 wt % and about 50 wt %, preferably between about 39 wt % and about 46 wt %.

91. The fertilizer granule of any one of items 86 to 90, wherein b is about 30 wt % or more, about 35 wt % or more, about 40 wt % or more, about 44 wt % or more, or about 45 wt % or more; and/or about 80 wt % or less, about 70 wt % or less, about 65 wt % or less, about 60 wt % or less, about 55 wt % or less, about 50 wt % or less, or about 49 wt % or less.

92. The fertilizer granule of any one of items 86 to 91, wherein when c is 0 wt %, b is about 50 wt %.

93. The fertilizer granule of any one of items 86 to 92, wherein when c is greater than 0 wt %, b is between about 40 wt % and about 50 wt %, preferably between about 44 wt % and about 49 wt %.

94. The fertilizer granule of any one of items 86 to 93, wherein c is about 0 wt % or more, about 1 wt % or more, about 2 wt % or more, about 3 wt % or more, about 4 wt % or more, about 5 wt % or more; and/or about 30 wt % or less, about 25 wt % or less, about 20 wt % or less, about 17 wt % or less, about 15 wt % or less, about 12 wt % or less, or about 10 wt % or less.

95. The fertilizer granule of any one of items 86 to 94, wherein c is 0 wt %.

96. The fertilizer granule of any one of items 86 to 94, wherein c is greater than 0 wt %.

97. The fertilizer granule of any one of items 86 to 96, wherein Y3 represents repeat units of formula (III):

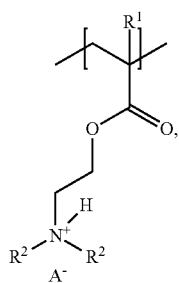

(III)

wherein:

R$^1$ is a hydrogen atom or methyl;

R$^2$ is the same or different C$_{1-6}$ alkyl; and

A$^-$ is a carboxylate anion of an organic acid that is a plant hormone or a phosphorus solubilizer.

98. The fertilizer granule of item 97, wherein R$^1$ is methyl.

99. The fertilizer granule of item 98 or 98, wherein both R$^2$ groups are methyl.

100. The fertilizer granule of any one of items 97 to 99, wherein Y3 is a repeat unit obtained by polymerizing one of the following monomer:

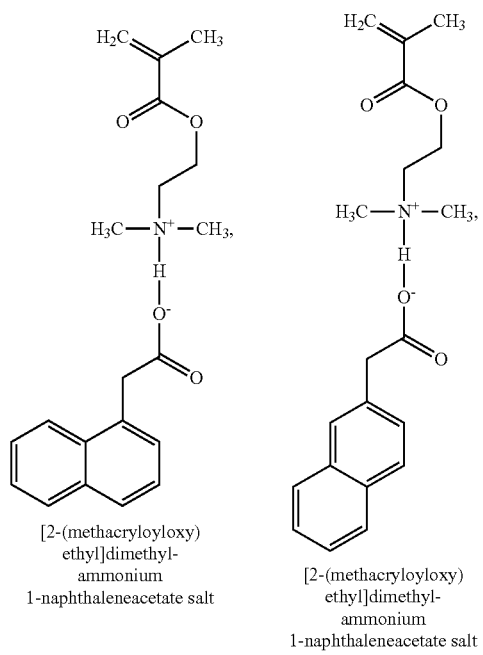

[2-(methacryloyloxy) ethyl]dimethyl-ammonium 1-naphthaleneacetate salt

[2-(methacryloyloxy) ethyl]dimethyl-ammonium 1-naphthaleneacetate salt

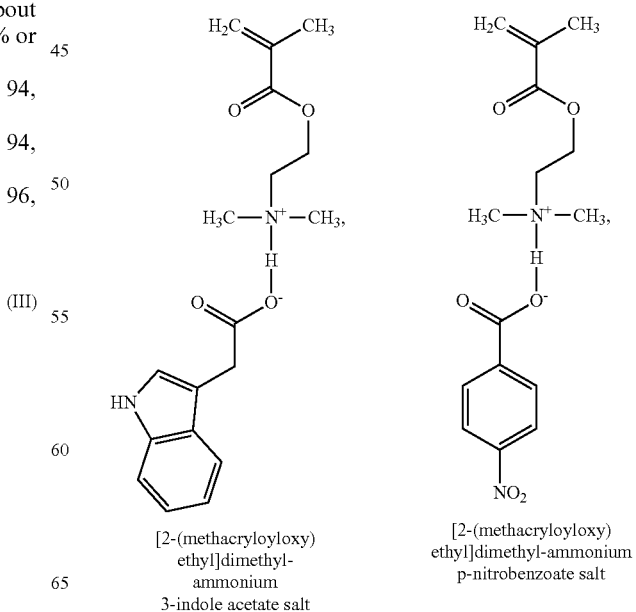

[2-(methacryloyloxy) ethyl]dimethyl-ammonium 3-indole acetate salt

[2-(methacryloyloxy) ethyl]dimethyl-ammonium p-nitrobenzoate salt

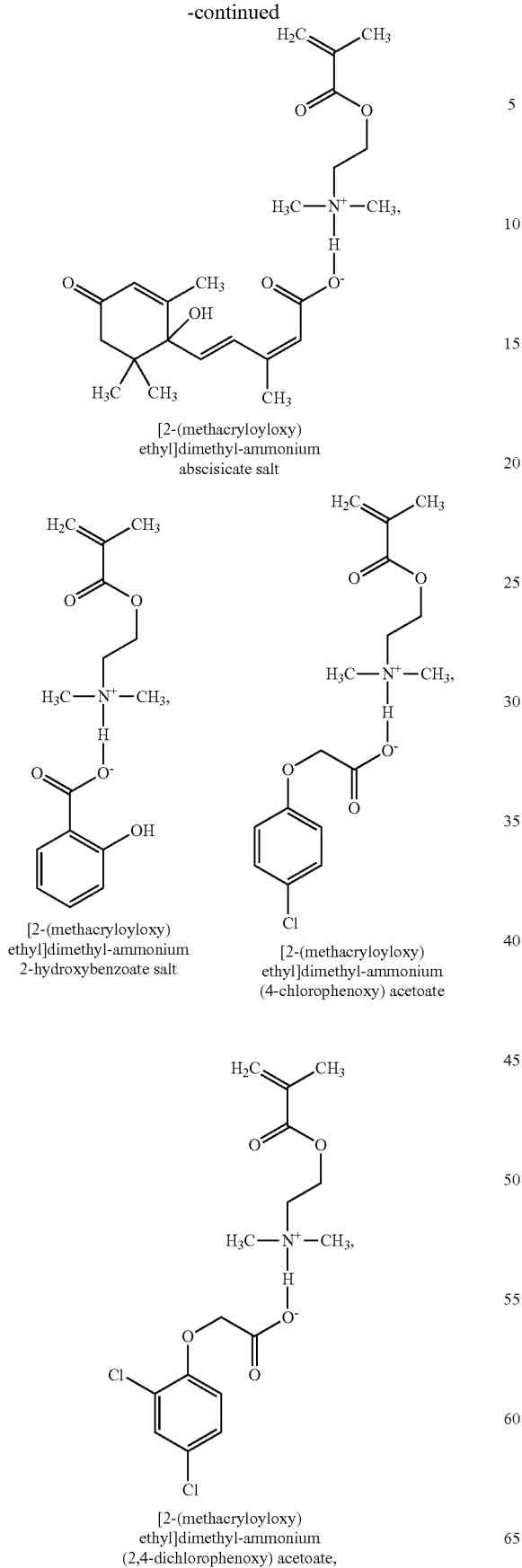
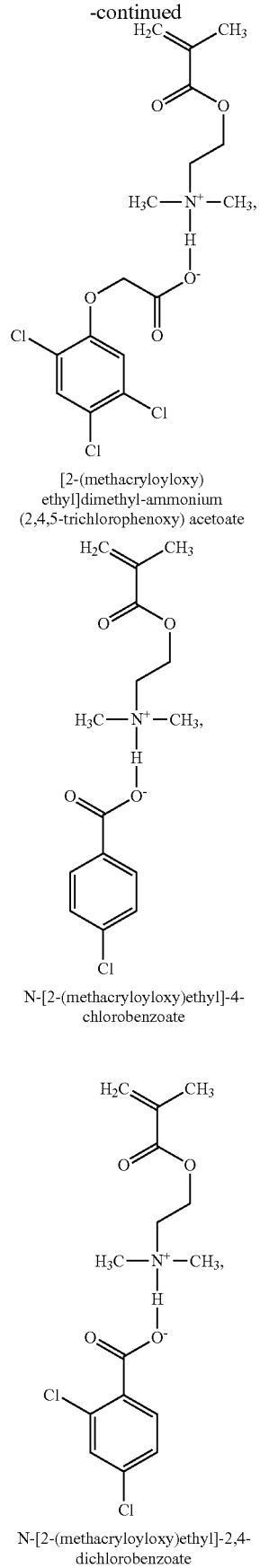

-continued

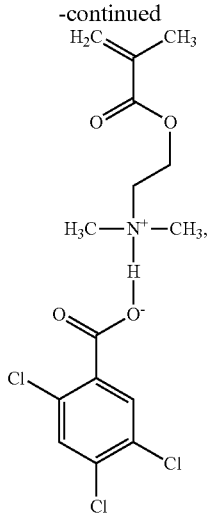

N-[2-(methacryloyloxy)
ethyl]-2,4,5-trichlorobenzoate

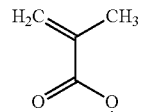
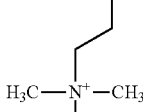
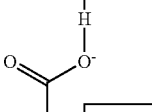
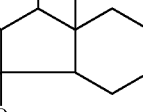

[2-(methacryloyloxy)
ethyl]dimethyl-ammonium
Gibberellate salt (GA3)

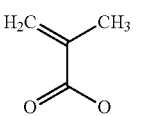
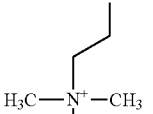
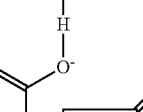
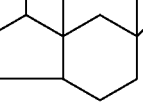

[2-(methacryloyloxy)
ethyl]dimethyl-ammonium
Gibberellate salt (GA4)

-continued

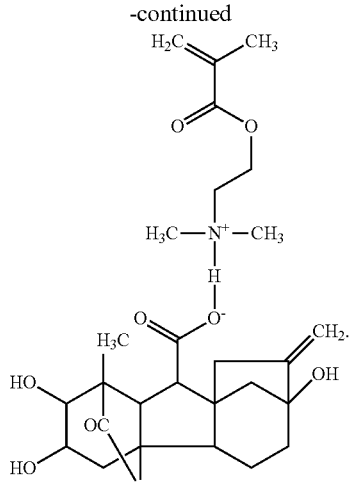

[2-(methacryloyloxy)
ethyl]dimethyl-ammonium
Gibberellate salt (GA13)

101. The fertilizer granule of any one of items 86 to 100, wherein the copolymers of formula (II) has the following ideal chemical structure:

POLY-004

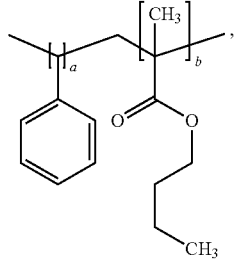

preferably wherein a is about
50 wt % and b is about 50 wt %,

POLY-005/POLY-006

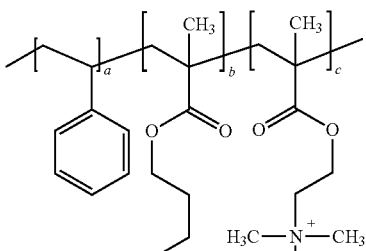

preferably wherein a is about 44 wt %,
b is about 47 wt %, and c is about 9 wt %,
or wherein a is about 39 wt %,
b is about 44 wt %, and c is about 17 wt %,
more preferably wherein a is about 44 wt %,
b is about 7 wt %, and c is about 9 wt %,

POLY-007/POLY-008

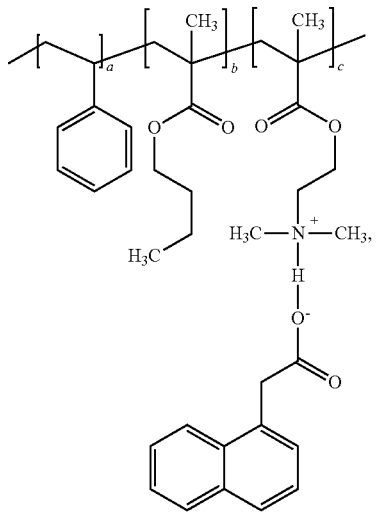

preferably wherein a is about 46 wt %,
b is about 48 wt %, and c is about 6 wt %,
or wherein a is about 41 wt %,
b is about 47 wt %, and c is about 12 wt %,
more preferably wherein a is about 46 wt %,
b is about 48 wt %, and c is about 6 wt %,

POLY-009

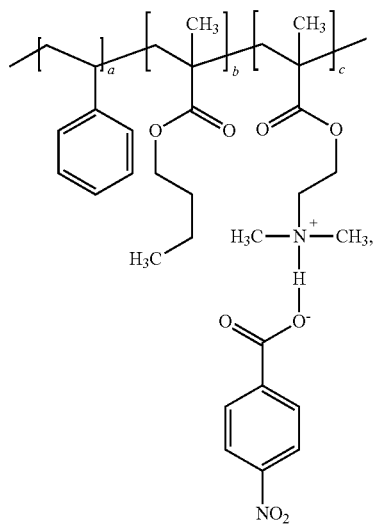

preferably wherein a is about 46 wt %,
b is about 48 wt %, and c is about 6 wt %,

POLY-010

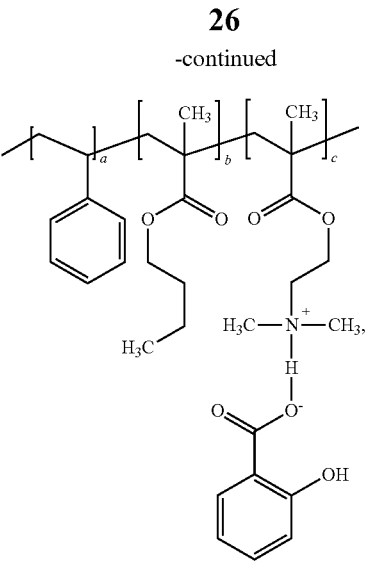

preferably wherein a is about 46 wt %,
b is about 49 wt %, and c is about 5 wt %, or

POLY-011

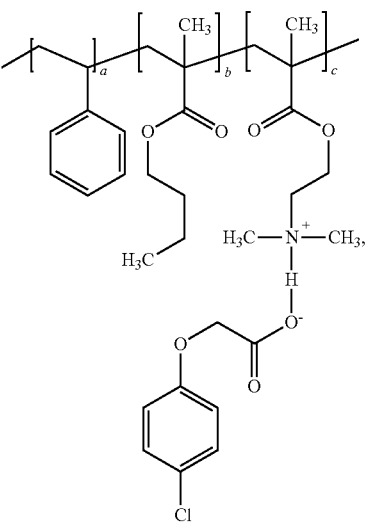

preferably wherein a is about 46 wt %,
b is about 48 wt %, and c is about 6 wt %.

102. The fertilizer granule of any one of items 86 to 101, wherein the copolymers of formula (II) is POLY-004, POLY-005, and POLY-007, preferably POLY-004.

103. The fertilizer granule of any one of items 86 to 96, wherein Y3 represents repeat units of formula (IV):

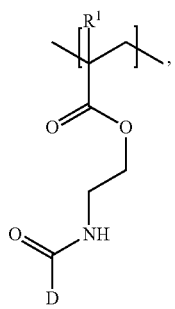

(IV)

wherein:
R¹ is a hydrogen atom or methyl;
D-C(=O)— is a residue of an organic acid that is a plant hormone or a phosphorus solubilizer.
104. The fertilizer granule of item 103, wherein the organic acid that is a plant hormone or a phosphorus solubilizer is gibberellic acid, indole-3-acetic acid, 1-naphthalene acetic acid, 2-naphthalene acetic acid, 4-nitrobenzoic acid, 4-chlorophenyloxyacetic acid, or salicylic acid.
105. The fertilizer granule of item 86 to 96, 103 and 104, wherein the copolymer of formula (II) has the following ideal chemical structures:

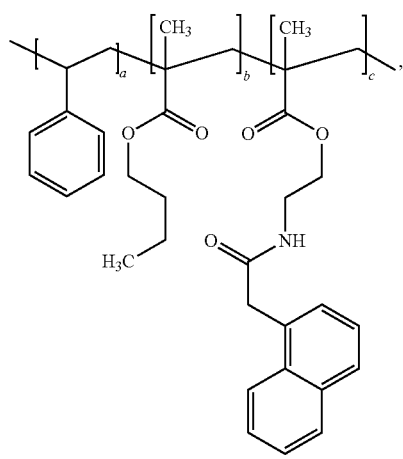

POLY-012 preferably wherein a is about 47 wt %, b is about 50 wt %, and c is about 3 wt %,

POLY-013

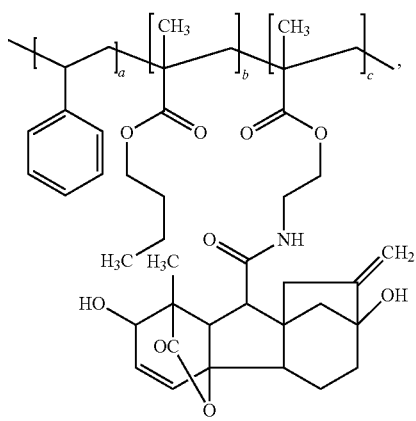

preferably wherein a is about 47 wt %, b is about 50 wt %, and c is about 3 wt %,

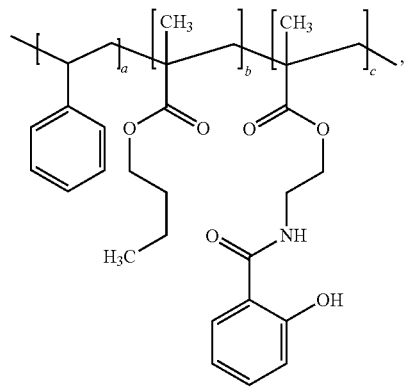

POLY-014 preferably wherein a is about 47 wt %, b is about 50 wt %, and c is about 3 wt %, or

POLY-015

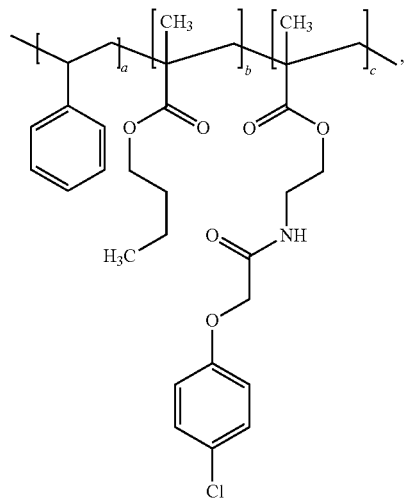

preferably wherein a is about 47 wt %, b is about 50 wt %, and c is about 3 wt %.

DETAILED DESCRIPTION OF THE INVENTION

Turning now to the invention in more details, there is provided a smart release nitrogen-containing fertilizer granule comprising:
  a nitrogen-containing fertilizer core;
  an organic functional layer covering the core, wherein the organic functional layer comprises at least one functional organic compound that is an enzyme inhibitor, a microbial suppressor, a phosphorus solubilizer, and/or a plant hormone;
  a controlled release layer covering the organic functional layer, wherein the controlled release layer comprises water-swellable copolymeric nanoparticles; and
  an anticaking layer covering the controlled release layer, wherein the anticaking layer comprises water-insoluble copolymeric nanoparticles.

Figure 1:
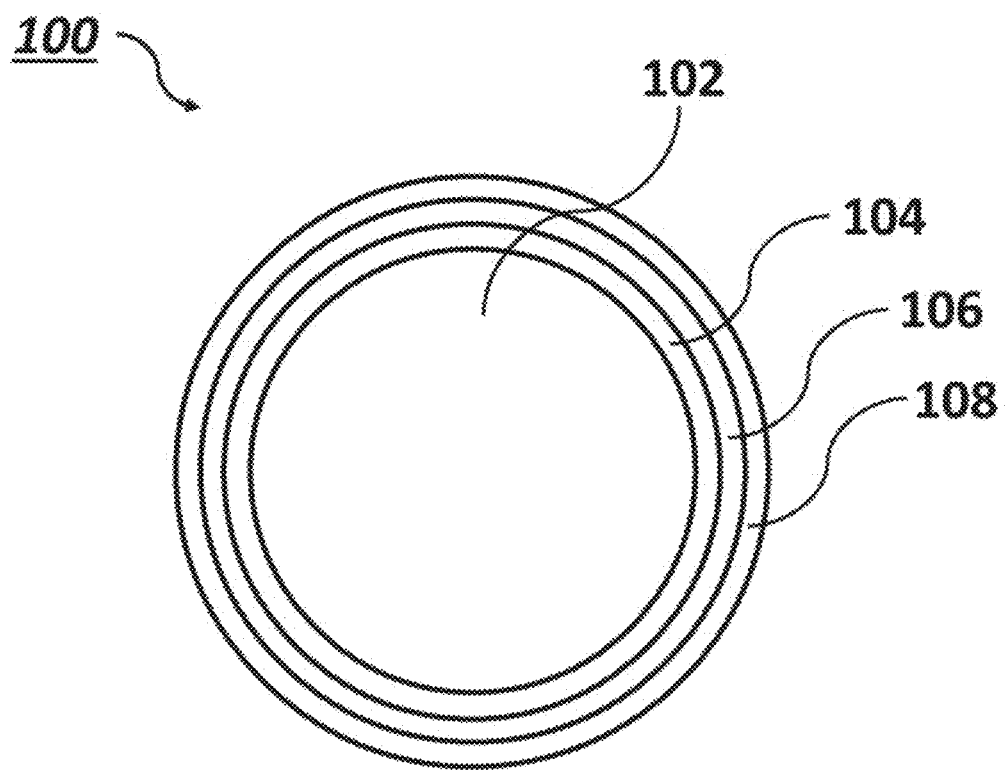
FIG. 1 is a 3D cutaway view an embodiment of the smart release nitrogen-containing fertilizer granule (100) of the invention.

FIG. 1 shows a cross-sectional scheme (not to scale) of an embodiment of the smart release nitrogen-containing fertilizer granule (100) of the invention with a nitrogen-containing fertilizer core (102). The core (102) is covered with the organic functional layer (104), which is in turn covered by the polymeric controlled release layer (106), which is finally covered with the polymeric anticaking layer (108).

When the smart release nitrogen-containing fertilizer granules are used (in fields, planting containers, etc.), water molecules from the surrounding environment (i.e. soil or another growing medium) will diffuse inward through the anticaking layer (108), then through the controlled release layer (106) and finally through the functional organic layer (104). When coming into contact with the controlled release layer (106) and the organic functional layer (104), the water will cause the water-swellable nanoparticles in the controlled release layer (106)—and, in certain embodiments, in the organic functional layer (104)—to swell, while the anticaking layer (108), which contains water-insoluble nanoparticles, will not swell. As a result, the anticaking layer (108) will become under pressure and will eventually crack and detach from the granule. Once the anticaking layer (108) is cracked/detached, water intake will increase. Water will reach the core where it will dissolve the nitrogen-containing fertilizer. The resulting nitrogen-containing aqueous solution will diffuse outward through the organic functional release layer (104) and the controlled release layer (106) to finally reach and fertilize the surrounding environment.

One of the purposes of the anticaking layer is to prevent the smart release nitrogen-containing fertilizer granules from sticking to each other, especially in the presence of humidity and at temperatures above 30° C., for example during storage and transport. It will be clear from the above that another purpose of the anticaking layer is to delay water intake and nitrogen release. Indeed, these will be delayed until the anticaking layer cracks/detaches from the granule. Yet another purpose of the anticaking layer is, in certain embodiments, to release a plant hormone or phosphorus solubilizer in the surrounding environment. Indeed, in embodiments in which the water-insoluble nanoparticles of the anticaking layer are made of a copolymer comprising repeat units having a plant hormone or phosphorus solubilizer covalently or ionically attached as a pendant group, this plant hormone or phosphorus solubilizer will be released in the environment.

It has been explained above that one of the purposes of the controlled release layer (106)—and, in embodiments, of the organic functional layer (104)—is to swell to create pressure that will cause the anticaking layer to crack/detach.

Another purpose of the controlled release layer (106) is to control the nitrogen release rate and the timing of nitrogen release. For example, when the controlled release layer is thicker, the nitrogen release rate is slower. When the controlled release layer is thinner, the nitrogen release rate is faster. See e.g. FIGS. 11 to 14.

In embodiments, the organic functional layer (104) may also affect the nitrogen release rate. Indeed, for example, a humus organic functional layer significantly increases the nitrogen release rate. See e.g. FIGS. 11 and 12.

Herein, "covered" or "covering" as in "an organic functional layer covering the core" means that the totality of the surface of the substrate (the core in this example) is covered by the layer (the organic functional layer in this example).

Herein, "nanoparticles" are particles with an average particle size between about 40 nm and about 200 nm. Preferably, the nanoparticles have an average particle size of about 40 nm or more, about 50 nm or more, about 60 nm or more, about 70 nm or more, about 75 nm or more, or about 80 nm or more; and/or an average particle size of about 200 nm or less, about 180 nm or less, about 160 nm or less, about 150 nm or less, about 140 nm or less, about 130 nm or less, about 125 nm or less, about 120 nm or less, about 115 nm or less, or about 110 nm or less. In preferred embodiments, the nanoparticles have an average particle size between about 75 nm and about 110 nm. The average particle size can be measured in a dilute water solution using a particle size analyzer, for example a Brookhaven® NanoBrook®173Plus.

Herein, "copolymeric nanoparticles" are nanoparticles made of a copolymer.

Herein, "water-swellable" nanoparticles are nanoparticles that, in the presence of water, absorb said water and swell, i.e. increase in volume.

Herein, "water-insoluble" nanoparticles are nanoparticles that do not significantly dissolve in water nor significantly swell in the presence of water. When these nanoparticles can be dispersed in water, they can also be called "water-dispersible" nanoparticles.

Herein, the thickness of the organic functional layer, controlled release layer, and anticaking layer is expressed as a coating weight calculated as follows:

$$\text{coating weight of a layer (wt \%)} = \frac{\text{weight of the layer}}{\text{weight of the core}} * 100.$$

When the coating thickness is less than 1 wt %, it can be expressed, if desired, in ppm (1 wt %=10000 ppm).

As noted above, the smart release nitrogen-containing fertilizer granule comprises one or more enzyme inhibitors, microbial suppressors, phosphorus solubilizers, and/or plant hormones. These compounds are comprised in the organic functional layer. In some instances, they may also be covalently or ionically attached to the copolymer forming the water-insoluble copolymeric nanoparticles of the anticaking layer. These compounds, once delivered to the surrounding environment, act according to their nature, i.e. enzyme inhibitors, microbial suppressors, phosphorus solubilizers, and/or plant hormones.

Core

Herein, a "nitrogen-containing fertilizer" has its regular meaning in the art in fertilizers, that is a water-soluble nitrogen-containing salt or organic compound conventionally used to provide nitrogen to plants.

Thus, herein, a "nitrogen-containing fertilizer core" is a core comprising one or more such nitrogen-containing fertilizers.

Non-limiting examples of nitrogen-containing fertilizers include those commonly found in conventional nitrogen-containing fertilizers, such as urea

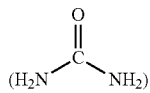

and water-soluble ammonium salts, including ammonium sulfates, ammonium phosphates and ammonium nitrates. Preferred nitrogen-containing fertilizers include urea, ammonium nitrate, calcium ammonium nitrate, ammonium sulfate, monoammonium phosphate (MAP), diammonium phosphate (DAP), and triammonium phosphate (TAP). More preferred nitrogen-containing fertilizers include urea, ammonium nitrate, ammonium sulfate, monoammonium phosphate, diammonium phosphate and triammonium phosphate, preferably urea and diammonium phosphate.

From the above, it will be apparent to the skilled person that in many cases, the nitrogen-containing fertilizers also contains phosphorus (often in the form of phosphate groups), which is a plant nutrient. Thus, in such cases, the fertilizer granules of the invention release both plant nutrients (N and P) in the environment.

In embodiments, the core is a conventional (preferably uncoated) nitrogen-containing fertilizer granule commercially sold for use as a fertilizer.

The core can be of any shape, for example roughly spherical. In embodiments, the core is of the shape of a conventional (preferably uncoated) granule commercially sold for use as a fertilizer.

The core can be of any size. In embodiments, the core is of the size of a conventional (preferably uncoated) granule commercially sold for use as a fertilizer. In embodiments, the core ranges from about 1.0 mm to about 5.0 mm in size, preferably from about 1.5 mm to about 5.0 mm.

Organic Functional Layer

The organic functional layer comprises at least one functional organic compound that is an enzyme inhibitor, a microbial suppressor, a phosphorus solubilizer, and/or a plant hormone, preferably an enzyme inhibitor. These functional organic compounds help maximizing nutrient use efficiency and/or stimulate plant growth and/or resistance to biotic and abiotic stress.

In embodiments, the organic functional layer comprises two or more functional organic compounds to further maximize these effects.

As noted above, the organic functional layer is coated on the nitrogen-containing fertilizer core. The organic functional layer can be produced on the nitrogen-containing fertilizer core by applying an aqueous solution or suspension of the functional organic compound with, optionally, a polymeric binder, followed by drying. This can be carried out for example by spray coating the solution or suspension on the nitrogen-containing fertilizer core in a fluidized bed. In embodiments, the temperature for the coating and drying steps is between about 25 and about 50° C.

In embodiments, the organic functional layer has a coating weight between about 0.1 wt % and about 10 wt % preferably between about 0.1 wt % and about 7 wt %, and more preferably between about 0.1 wt % and about 4.0 wt % (based on the weight of the nitrogen-containing fertilizer core).

Microbial Suppressors

Microbial suppressors are compounds that inhibit or at least reduce the metabolic activity of one or more microorganism that is deleterious to the action of the fertilizer.

Preferred microbial suppressors include nitrification inhibitors, which are compounds that inhibit or at least reduce the nitrification of ammonium salt to nitrite and nitrate by bacteria, such as autotrophic ammonia-oxidizing bacteria like nitrosomonas and nitrobacter.

Preferred nitrification inhibitors include dicyandiamide (DCD), 2-chloro-6-(trichloromethyl)pyridine (nitrapyrin), 5-ethoxy-3-trichloromethyl-1,2,4-thiadiazole (Terrazole®), 2-amino-3-chloro-6-methylpyridine (AM), 2-mercaptobezothiazole (MBT), and 2-sulfanimalamidothiazole (ST), as well as combinations thereof. More preferred nitrification inhibitors include dicyandiamide (DCD).

Phosphorus Solubilizers

Phosphorus solubilizers increase nutrient use efficiency. Phosphorus solubilizers are compounds, preferably organic acids and their salts, that help solubilize phosphorus immobilized in the soil due to complexation with aluminum and ferric cations or adsorption. Indeed, phosphorus (also in the form of phosphate) is found in water-soluble forms, adsorbed on solid particles and in water-insoluble forms, the latter being due to reaction of phosphate with $A^{3+}$ and $Fe^{3+}$ in the soil to form $AlPO_4$ and $FePO_4$. Using a phosphorus solubilizer, such as organic acids and their salts, it is possible to increase the amount of water-soluble phosphate in the soil due to the formation of $A^{3+}$ and $Fe^{3+}$ with the organic acid anion ($A^-$). For example, lauric acid dissolves more selectively $AlPO_4$, citric acid dissolves more selectively to $FePO_4$, and gluconic acid dissolves both Al and Fe phosphate salts.

Preferred phosphorus solubilizers include citric acid, lauric acid, alkyl sulfuric acid, wherein the alkyl group is preferably a linear or branched alkyl chain with 4 to 24 carbon atoms (preferably lauryl sulfuric acid), oxalic acid, and gluconic acid as well as their salts. Preferred such salts include for example alkali salts, such as sodium and potassium salts. More preferred phosphorus solubilizers include citric acid, gluconic acid, and oxalic acid as well as their salts and alkyl sulfuric acid salts. Most preferred phosphate solubilizers include alkyl sulfuric acid salts, such as sodium alkyl sulfate and potassium alkyl sulfate.

Plant Hormones

Plant hormones are well-known to the skilled person. Preferred plant hormones include, among others, plant growth hormones (PGH) that stimulate plant growth and plant immune hormones (PIH) that stimulate resistance to biotic and abiotic stressors. Of note, some plant hormones present both PGH and PIH activity. Non-limiting examples of plant hormones include:

abscisic acid (PGH);

auxins (PGH and in some cases also PIH), including:
- native auxins such as indole-3-acetic acid, 4-chloroindole-3-acetic acid, 2-phenylacetic acid, indole-3-butanoic acid, and indole-3-propanoic acid, and
- synthetic auxins such as 1-naphthaleneacetic acid, 2,4,5-trichlorophenoxyacetic acid, 2,4-dichlorophenoxyacetic acid, 4-chlorophenoxyacetic acid, 2-methoxy-3,6-dichlorobenzoic acid, 4-nitrobenzoic acid, 2-hydroxybenzoic acid, 4-chlorobenzoic acid, 2,4-dichlorobenzoic acid, 2,4,5,-trichlorobenzoic acid, and 4-amino-3,5,6-trichloropicolinic acid;

gibberellins, which are a group of more than 125 well-known closely related tetracyclic diterpene acids (PGH and in some cases also PIH);

Gibberellins are derived from the ent-gibberellane skeleton and have either 19 or 20 carbons. The 19-carbon gibberellins, such as gibberellic acid (GA3), have lost carbon 20 and, in place, possess a five-member lactone bridge that links carbons 4 and 10. Gibberellins are named GA1 through GAn in order of discovery. Non-liming examples of gibberellins include GA1, gibberellic acid (GA3), GA4, GA5, GA6, GA7, GA13, and preferably gibberellic acid.

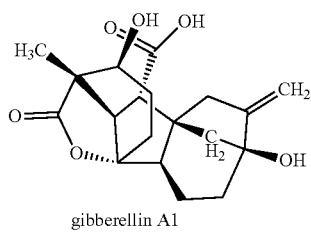

(GA1)

gibberellin A1

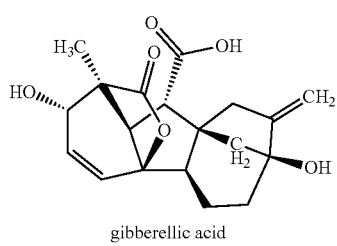

(GA3)

gibberellic acid

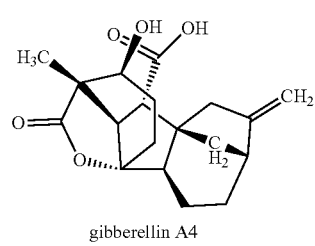

(GA4)

gibberellin A4

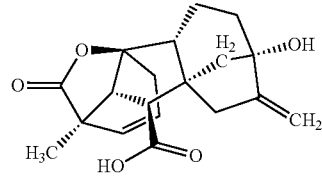

(GA5)

gibberellin A5

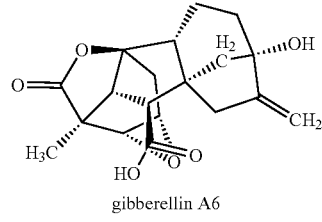

(GA6)

gibberellin A6

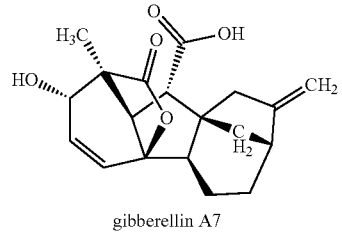

(GA7)

gibberellin A7

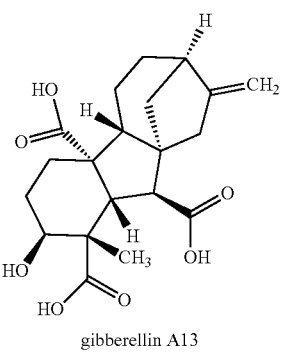

(G)

gibberellin A13 salicylic acid (PGH and PIH);
jasmonic acid (PGH and PIH);
oxalic acid (PGH);
citric acid (PGH); and
pipecolic acid (PIH),
and combinations thereof.

In preferred embodiments, the plant hormone is 4-chlorophenyloxy acetic acid, indole-3-acetic acid, gibberellic acid, 1-naphthalene acetic acid, 4-nitrobenzoic acid, salicylic acid, or a combination thereof.

Enzyme Inhibitors

Enzyme inhibitors are compounds that inhibit the action of an enzyme that is deleterious to the action of the fertilizer.

Preferred enzyme inhibitors include urease inhibitors, i.e. compounds that inhibit or at least reduce the activity of the urease enzyme, which undesirably hydrolyzes nitrogen-containing fertilizers, especially urea, into ammonium salt. Preferred urease inhibitors include:
- chitosan,
- humic acids (for example provided in the form of humus),
- fulvic acids,
- unsubstituted or substituted polyphenols,
- saponin,
- N-(n-butyl)thiophosphoric triamide (NBTPT),
- phenylphosphorodiamidate (PPDA),
- acetohydroxamic acid,
- alkyl hydroxamic acid,
- trans-cinnamoyl hydroxamic acid,
- benzohydroxamic acid, and
- hydroxamic acid, as well as combinations thereof. More preferred urease inhibitors include humic acids in the form of humus, chitosan, N-(n-butyl)thiophosphoric triamide (NBTPT), phenylphosphorodiamidate (PPDA), and unsubstituted or substituted polyphenols. Most preferred urease inhibitors include unsubstituted or substituted polyphenols.

Preferred polyphenols include tannic acid. Tannic acid is a polyphenol comprising, as can be seen in its chemical formula below, 5 polyphenolic branches, each branch bearing 3 terminal hydroxy (—OH) groups:

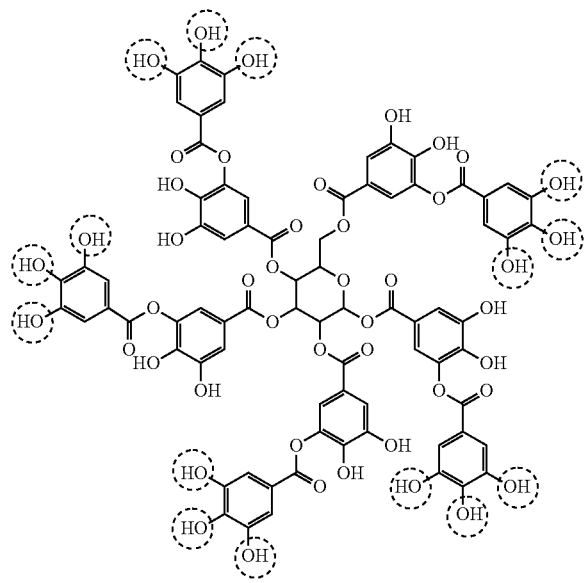

Tannic acid (with the terminal hydroxy groups of each phenolic branch circled).

Unfortunately, in practice, an organic functional layer comprising unsubstituted tannic acid can be sticky during coating on the fertilizer core, which causes difficulty when attempting to produce large quantities of fertilizer granules.

In preferred embodiments, the tannic acid (and polyphenols generally) is substituted as described below. It has been surprisingly found that such substitution allows to easily produce large quantities of the fertilizer granules as it reduces the stickiness of the granules during coating of the organic functional layer. Thus, in embodiments, the tannic acid (and polyphenols generally) bears one or more, preferably two or more, more preferably five substituents as described below. Preferably, one or more, preferably two or more, and more preferably five of the hydroxy groups of the tannic acid (and polyphenols generally) are replaced by —OR$^1$ groups in which R$^1$ is a substituent as described below. More preferably, one terminal hydroxy group on each of the phenolic branches of the polyphenol (e.g. one terminal hydroxy group on each of the five phenolic branches of the tannic acid) is replaced by a —OR$^1$ group, in which R$^1$ is a substituent as described below.

In embodiments, the substituent(s) (R$^1$) of the polyphenols (preferably tannic acid) comprise a functional group bearing negative or positive charge and an oppositely charged counterion.

Non-limiting examples of functional groups a bearing negative or positive charge include carboxylate (—COO$^-$), sulfonate (—SO$_3^-$), ammonium (—NH$_3^+$), alkyl ammonium (—N(alkyl)H$_2^+$), and dialkyl ammonium (—N(alkyl)$_2$H$^+$), wherein the alkyl is preferably a C$_{1-6}$ alkyl.

The functional groups bearing negative or positive charge can be attached to the polyphenols (preferably tannic acid) directly or indirectly via a linking group, preferably the functional groups are attached indirectly via a linking group. Non-limiting examples of linking groups include alkylene groups, preferably comprising between 1 and 6 carbon atoms and more preferably between 1 and 4 carbon atoms.

Preferred functional group and linking group couples include:
- acetate (—CH$_2$—COO$^-$),
- butyl sulfonate (—(CH$_2$)$_4$—SO$_3^-$), and
- ethyl ammonium (—(CH$_2$)$_2$—NH$_3^+$).

Non-limiting examples of oppositely charged counterion include metal cations and carboxylate or sulfonate anions of organic acids that are microbial suppressors, phosphorus solubilizers, and/or plant hormones, preferably plant hormones. Organic acids that are enzyme inhibitors, microbial suppressors, phosphorus solubilizers, and/or plant hormones have been described above—this matter is not repeated here.

Preferred metal cations include alkali cations, preferably K$^+$.

Preferred carboxylate or sulfonate anions of organic acids that are enzyme inhibitors, microbial suppressors, phosphorus solubilizers, and/or plant hormones include the carboxylate anions of gibberellic acid, 1-napthanlene acetic acid and 4-nitrobenzoic acid.

Preferred substituent(s) of polyphenols (preferably tannic acid), which comprise a functional group bearing negative or positive charge and an oppositely charged counterion, include:

- acetic acid potassium salt (-CH$_2$-COO-K$^+$),
- butyl sulfonic acid potassium salt (-(CH$_2$)$_4$-SO$_3$-K$^+$),
- ethyl ammonium gibberellic acid salt (-(CH$_2$)$_2$-NH$_3^+$

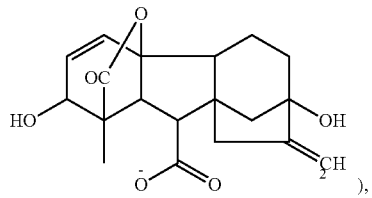

),

37
-continued
• ethyl ammonium 1-napthanlene acetic acid salt (-(CH$_2$)$_2$-NH$_3^+$
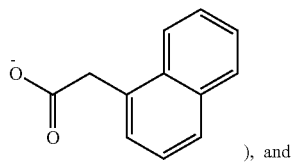
), and
38
-continued
• ethyl ammonium 4-nitrobenzoic acid salt (-(CH$_2$)$_2$-NH$_3^+$
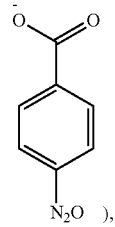
),
Preferred substituted tannic acids have the following ideal structures:
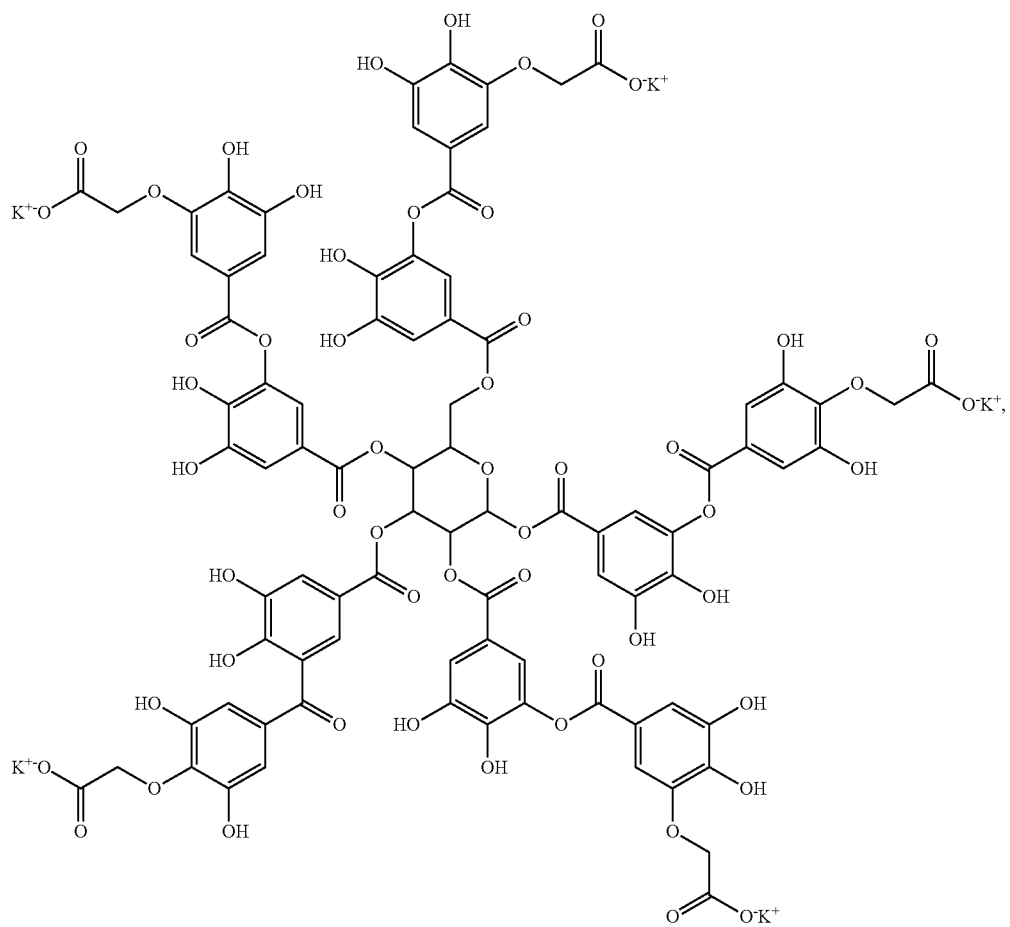
Tannic acid substituted with acetic acid potassium salt (TAAA)

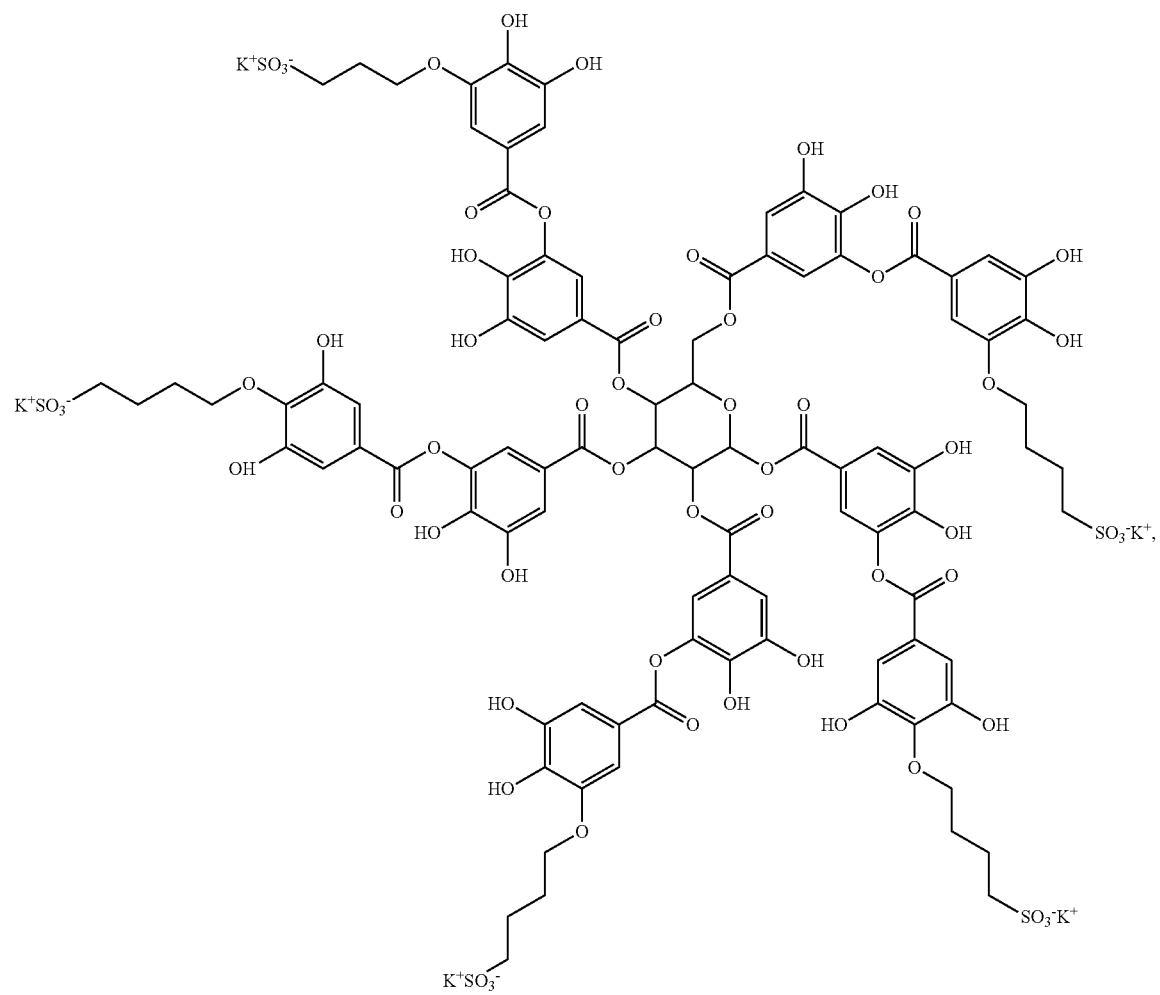
Tannic acid substituted with butyl sulfonic acid potassium salt (TABS)

-continued
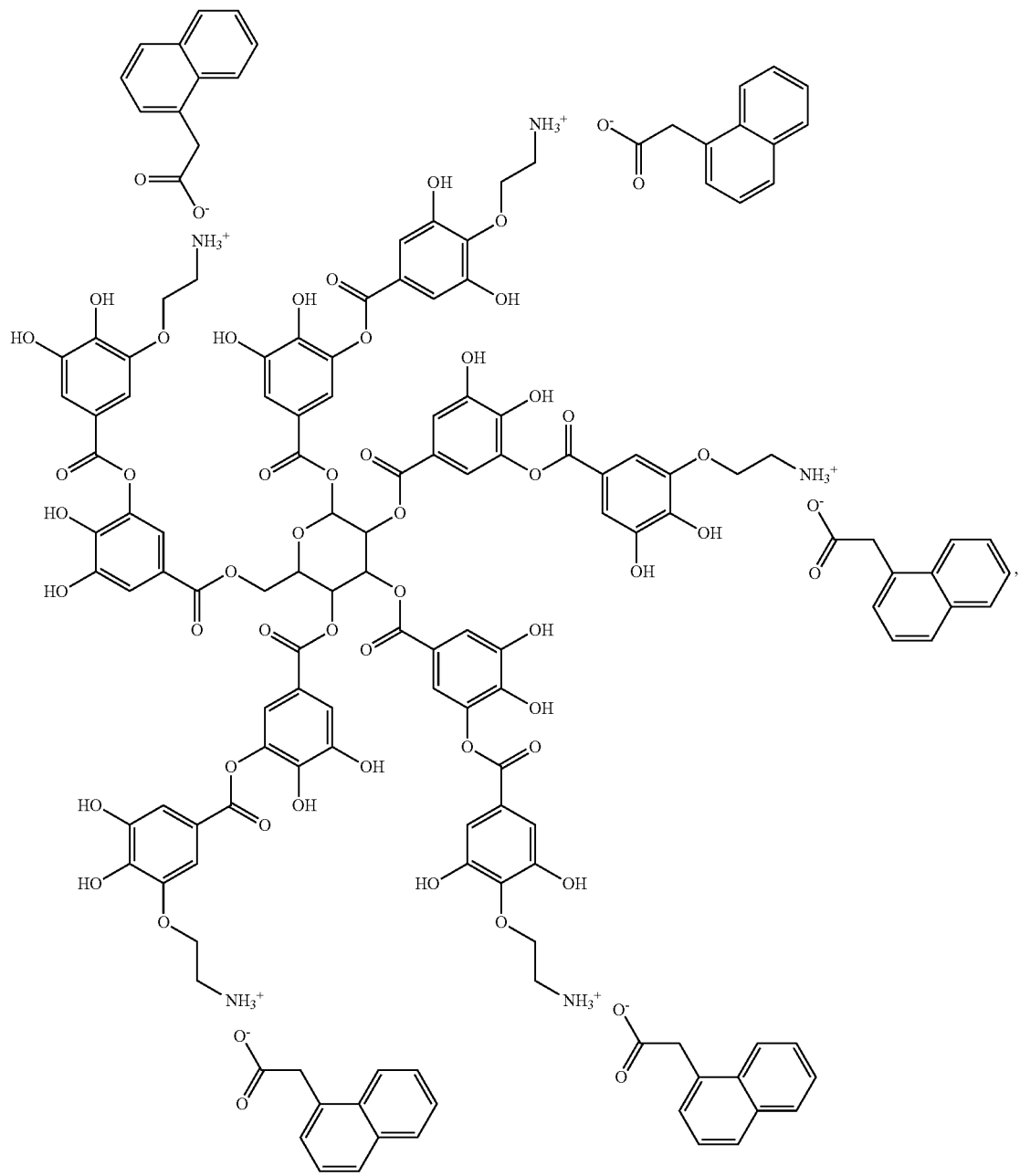
Tannic acid substituted with ethyl ammonium 1-napthanlene acetic acid salt (TANAA)

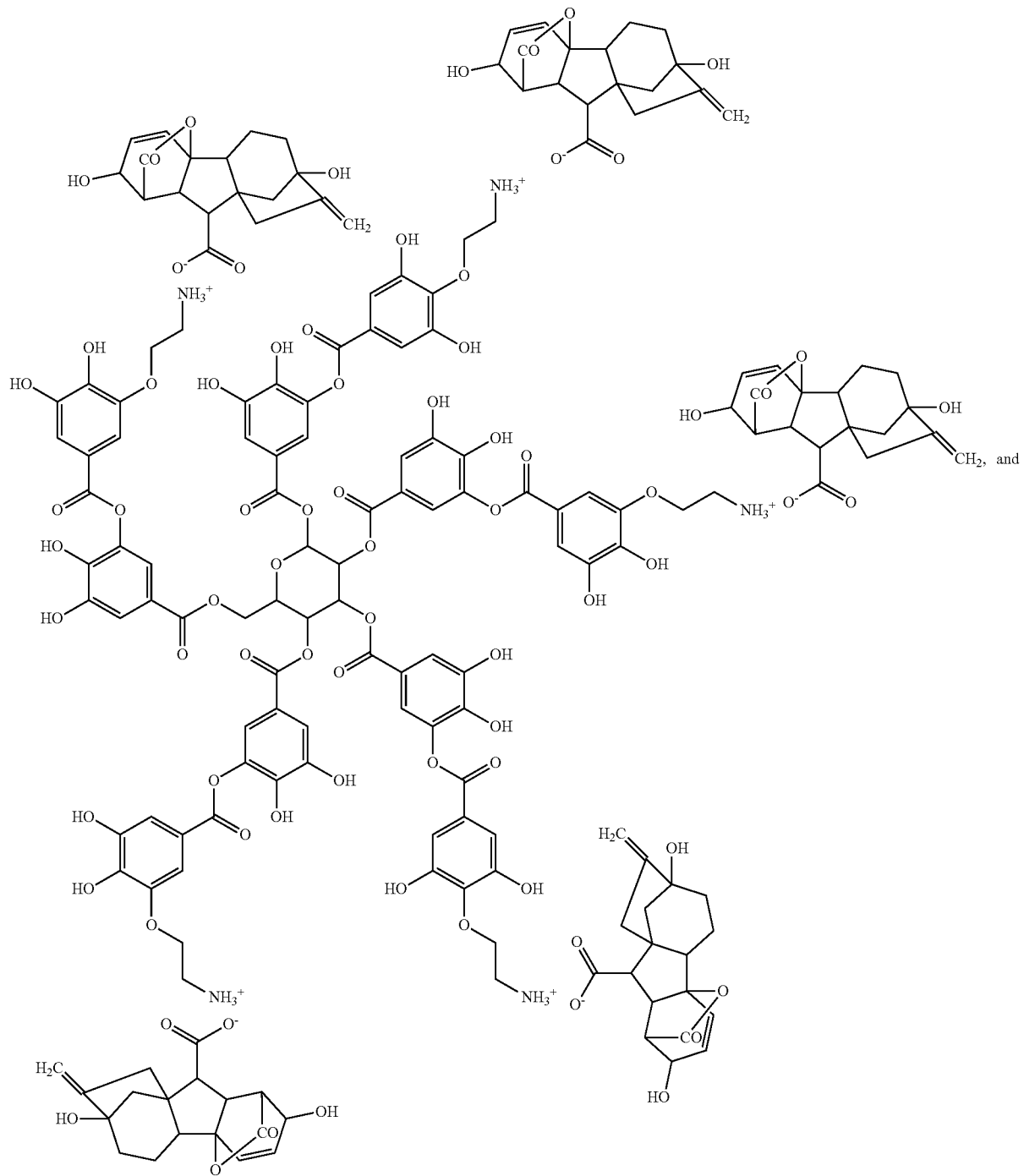
Tannic acid substituted with ethyl ammonium gibberellic acid salt (TAGA)

-continued

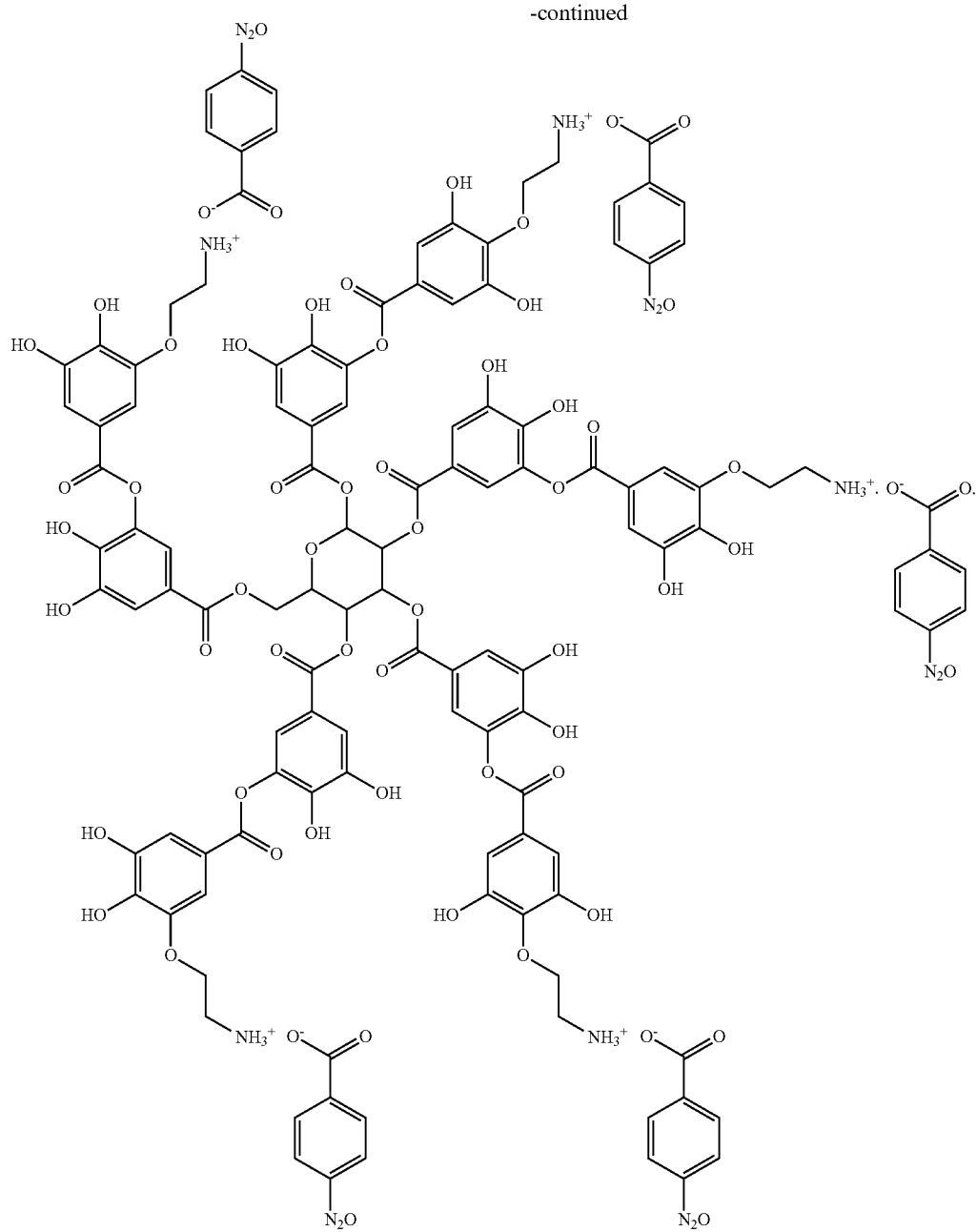

Tannic acid substituted with ethyl ammonium 4-nitrobenzoic acid salt (TABA, also called TANB)

Polymeric Binder

Optionally, in embodiments, the organic functional layer further comprises a water-soluble, water-swellable, or water-dispersible polymeric binder. The polymeric binder eases the formation of a cohesive coating, especially when the functional organic compound, when used by itself, does not allow the formation of such a coating.

In embodiments, the organic functional layer comprises about 0 wt % or more, about 10 wt % or more, about 20 wt % or more, about 30 wt % or more, about 40 wt % or more, or about 50 wt % or; and/or about 60 wt % or less, about 50 wt % or less, about 40 wt % or less, about 30 wt % or less, about 20 wt %, or about 10 wt % or less of the polymeric binder, based on the weight of the organic functional layer.

In preferred embodiments, the organic functional layer comprises about 0 wt %, 33 wt %, or 50 wt % of the polymeric binder based on the weight of the organic functional layer.

In embodiments, the organic functional layer comprises about 40 wt % or more, about 50 wt % or more, about 60 wt % or more, about 70 wt % or more, about 80 wt % or more, or about 90 wt % or more; and/or about 100 wt % or less, about 90 wt % or less, about 80 wt % or less, about 70 wt % or less, or about 60 wt % or less of the functional organic compounds (in total), based on the weight of the organic functional layer. In preferred embodiments, the organic functional layer comprises about 50 wt %, 64 wt %, or 100 wt % of the functional organic compounds (in total), based on the weight of the extended release layer.

In embodiments, the polymeric binder is water-swellable copolymeric nanoparticles. In embodiments, the copolymer making these water-swellable copolymeric nanoparticles comprises crosslinkable repeat units, i.e. at units that can undergo crosslinking with or without a crosslinking agent, upon drying of the organic functional layer.

The embodiments, the glass transition temperature of the copolymer, before crosslinking if any, ranges between about 18 and about 25° C.

In preferred embodiments, the copolymer making the water-swellable copolymeric nanoparticles of the organic functional layer is of formula (I):

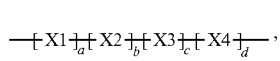

wherein:
- X1 represents styrene repeat units;
- X2 represents alkyl acrylate or alkyl methacrylate repeat units;
- X3 represents alkoxy dialkyl vinylsilane, dialkoxy alkyl vinylsilane, or trialkoxy vinylsilane repeat units;
- X4 represents acrylic acid, methacrylic acid, acrylamide, methacrylamide, vinyl phosphoric acid, or N,N-dimethylaminoethyl methacrylamide repeat units; and
- a, b, c and d represents the weight percent of repeat units X1, X2, X3, and X4, respectively, based on the total weight of the copolymer, and each vary between about 0.5 and about 50 wt %, wherein the X3 repeat units are optionally crosslinked with each other within the nanoparticles.

The above formula should be understood to represent copolymers in which all X2 repeat units are the same or in which X2 represents two or more alkyl acrylate and/or alkyl methacrylate repeat units. In preferred embodiments, all X2 repeat units are the same.

Similarly, the above formula should be understood to represent copolymers in which all X3 repeat units are the same or in which X3 represents two or more alkoxy dialkyl vinylsilane, dialkoxy alkyl vinylsilane, and/or trialkoxy vinylsilane repeat units. In preferred embodiments, all X3 repeat units are the same.

Similarly, the above formula should be understood to represent copolymers in which all X4 repeat units are the same or in which X4 represents two or more acrylic acid, methacrylic acid, acrylamide, methacrylamide, vinyl phosphoric acid, and/or N,N-dimethylaminoethyl methacrylamide repeat units. In preferred embodiments, all X4 repeat units are the same.

The alkyl group of the alkyl acrylate repeat units, alkyl methacrylate repeat units, alkoxy dialkyl vinylsilane repeat units, and dialkoxy alkyl vinylsilane repeat units can be linear or branched. In preferred embodiments, these alkyl groups comprise between 1 and 6 carbon atoms.

The alkoxy groups of the alkoxy dialkyl vinylsilane repeat units, dialkoxy alkyl vinylsilane repeat units, and trialkoxy vinylsilane repeat units can be linear or branched. In preferred embodiments, these alkoxy groups comprise between 1 and 6 carbon atoms.

As noted above, the X3 repeat units are optionally crosslinked with each other within the nanoparticles. Indeed, when producing the granules of the invention, the X3 repeat units can undergo self-crosslinking upon heating at a temperature between 40 and 50° C. In preferred embodiments, for example those in which the organic functional layer was produced in such conditions, some of the X3 repeat units are crosslinked with each other within the nanoparticles. In embodiments, up to about 3% of the X3 repeat units are crosslinked. More extensive crosslinking could yield an undesirably brittle organic functional layer. Crosslinking allows to modify the potassium release rate as desired. Indeed, crosslinking decreases the rate of swelling of the nanoparticles, which increase the potassium release rate, and allow using a thinner organic functional layer. In other embodiments, the X3 repeat units are not crosslinked with each other.

In preferred embodiments, the alkyl group of the alkyl acrylate or alkyl methacrylate repeat unit is butyl.

In preferred embodiments, X2 represents alkyl acrylate, preferably butyl acrylate.

In preferred embodiments, the alkoxy group of the alkoxy dialkyl vinylsilane, dialkoxy alkyl vinylsilane, or trialkoxy vinylsilane repeat units is ethoxy.

In preferred embodiments, X3 represents trialkoxy vinylsilane, preferably triethoxy vinylsilane repeat units.

In preferred embodiments, X4 represents acrylic acid, acrylamide, or vinyl phosphoric acid repeat units.

In preferred embodiments, a is about 25 wt % or more, about 35 wt % or more, about 40 wt % or more, or about 45 wt % or more; and/or about 75 wt % or less, about 65 wt % or less, about 60 wt % or less, about 55 wt % or less, or about 50 wt % or less. In more preferred embodiments, a is about 48 wt %.

In preferred embodiments, b is about 25 wt % or more, about 35 wt % or more, about 40 wt % or more, or about 45 wt % or more; and/or about 75 wt % or less, about 65 wt % or less, about 60 wt % or less, about 55 wt % or less, or about 50 wt % or less. In more preferred embodiments, b is about 48 wt %.

In preferred embodiments, c is about 0.5 wt % or more, about 1 wt % or more, about 1.5 wt % or more, about 2 wt % or more, about 2.5 wt % or more; and/or about 15 wt % or less, about 10 wt % or less, about 7.5 wt % or less, about 5 wt % or less, about 4 wt % or less, or about 3.5 wt % or less. In more preferred embodiments, c is about 3 wt %.

In preferred embodiments, d is about 0.5 wt % or more, about 0.6 wt % or more, about 0.7 wt % or more, about 0.8 wt % or more, about 0.9 wt % or more; and/or about 10 wt % or less, about 5 wt % or less, about 3 wt % or less, about 2 wt % or less, or about 1.5 wt % or less. In more preferred embodiments, d is about 1 wt %.

In most preferred embodiments, the copolymer making the water-swellable copolymeric nanoparticles of the organic functional layer has the following ideal chemical structure:

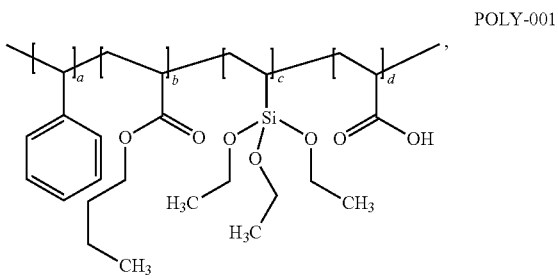

POLY-001

-continued

POLY-002

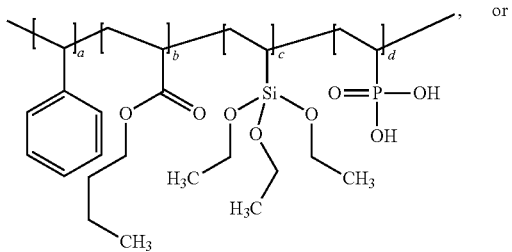

, or

POLY-003

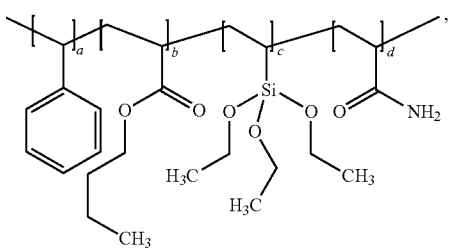

preferably wherein a, b, c and d are about 48 wt %, about 48 wt %, about 3 wt % and about 1 wt %, respectively, based on the total weight of the copolymer.

The polymeric binder may be a mixture of the above copolymeric nanoparticles.

The copolymeric nanoparticles may comprise a mixture of the above copolymers.

Copolymeric nanoparticles comprising crosslinkable trialkoxy vinylsilane repeat units, such as triethoxysilyl repeat units, can be synthesized by free radical emulsion copolymerization in an aqueous solution containing anionic and non-ionic surfactants, such as sodium n-dodecyl benzene sulfonate and n-octanol. A pH controlling agent, such as sodium bicarbonate might also be used in the copolymerization to provide a stable polymeric nanoparticle suspension with nanoparticles having a particle size in the 40 nm to 200 nm range.

Controlled Release Layer

As noted above, the controlled release layer covers the organic functional layer and comprises water-swellable copolymeric nanoparticles.

The controlled release layer can be produced on the organic functional layer by applying a suspension of the water-swellable copolymeric nanoparticles in an aqueous solvent, following by drying. This can be carried out for example by spray coating in a fluidized bed. In embodiments, the temperature for the coating and drying steps is from about 25 to below about 50° C.

In embodiments, the controlled release layer has a coating weight between about 2 wt % and about 10 wt % preferably between about 4 wt % and about 20 wt %, and more preferably between about 5 wt % and about 15 wt % (based on the weight of the nitrogen-containing fertilizer core). In preferred embodiments, the controlled release layer is thicker (has a larger coating weight) than the organic functional layer.

In embodiments, the copolymer making the water-swellable copolymeric nanoparticles of the controlled release layer comprise crosslinkable repeat units, that can undergo crosslinking, with or without crosslinking agents, upon drying of the controlled release layer.

The embodiments, the glass transition temperature of this copolymer, before crosslinking if any, ranges between about 18 and about 25° C.

In preferred embodiments, the copolymer making the water-swellable copolymeric nanoparticles of the controlled release layer is of formula (I) as defined above, including all preferred embodiments thereof. Thus, in most preferred embodiments, this copolymer is POLY-001, POLY-002 and POLY-003, more preferably POLY-001.

The copolymeric nanoparticles may comprise a mixture of the above copolymers.

The controlled release layer may comprise a mixture of the above copolymeric nanoparticles.

Anticaking Layer

The anticaking layer covers the controlled release layer and comprises water-insoluble copolymeric nanoparticles.

The anticaking layer can be produced on the controlled release layer by applying a suspension of the water-insoluble copolymeric nanoparticles in an aqueous solvent, followed by drying. This can be carried out for example by spray coating in a fluidized bed. In embodiments, the temperature for the coating and drying steps is between about 30° C. and about 70° C., preferably between about 35° C. and about 65° C.

In embodiments, the anticaking layer has a coating weight between about 1 wt % and about 10 wt %, preferably between about 2 wt % and about 5 wt % (based on the weight of the nitrogen-containing fertilizer core).

In embodiments, the copolymer making the water-insoluble copolymeric nanoparticles comprises repeat units having a plant hormone or a phosphorus solubilizer covalently or ionically attached as a pendant group.

The embodiments, the glass transition temperature of the copolymer ranges between about 35 and about 55° C.

In preferred embodiments, the copolymer making the water-insoluble copolymeric nanoparticles is of formula (II):

(II)

wherein:
Y1 represents styrene repeat units;
Y2 represents alkyl acrylate or alkyl methacrylate repeat units;
Y3 represents repeat units comprising, as a pendant group, an ionically or covalently attached plant hormone or phosphorus solubilizer;
a and b represents the weight percent of repeat units Y1 and Y2, respectively, based on the total weight of the copolymer, and vary between about 10 wt % to about 95 wt %; and
c represents the weight percent of repeat units Y3, based on the total weight of the copolymer, and vary between 0 wt % to about 30 wt %.

The above formula should be understood to represent copolymers in which all Y2 repeat units are the same or in which Y2 represents two or more alkyl acrylate and/or alkyl methacrylate repeat units. In preferred embodiments, all Y2 repeat units are the same.

Similarly, the above formula should be understood to represent copolymers in which all Y3 repeat units are the same or in which Y3 represents two or more different repeat units comprising, as a pendant group, ionically or covalently attached plant hormones and/or phosphorus solubilizers. In preferred embodiments, all Y3 repeat units are the same.

The alkyl groups of the alkyl acrylate repeat units and the alkyl methacrylate repeat units can be linear or branched. In preferred embodiments, these alkyl groups comprise between 1 and 6 carbon atoms, preferably butyl.

In preferred embodiments, Y2 represents alkyl acrylate, preferably butyl acrylate.

In embodiments, the plant hormone or phosphorus solubilizer that is covalently or ionically attached as a pendant group to the copolymer making the water-insoluble copolymeric nanoparticles, for example the copolymer of formula (II), is:
- a residue of an organic acid that is a plant hormone or phosphorus solubilizer or
- a carboxylate anion of an organic acid that is a plant hormone or phosphorus solubilizer.

When it is covalently attached, the plant hormone or phosphorus solubilizer is preferably a residue of an organic acid (that is a plant hormone or phosphorus solubilizer).

When it is ionically attached, the plant hormone or phosphorus solubilizer is preferably a carboxylate anion of an organic acid (that is a plant hormone or phosphorus solubilizer).

In preferred embodiments, the organic acid is a phosphorus solubilizer. Such phosphorus solubilizers are as defined above, including preferred embodiments thereof.

In preferred embodiments, the organic acid is a plant hormone. Such plant hormones are as defined above, including preferred embodiments thereof.

In preferred embodiments, the organic acid that is a plant hormone or phosphorus solubilizer is:
- 1-naphthalene acetic acid, 2,4,5-trichlorobenzoic acid, 2,4,5-trichlorophenoxyacetic acid, 2,4-dichlorobenzoic acid, 2,4-dichlorophenoxyacetic acid, 2-hydroxybenzoic acid, 4-chlorobenzoic acid, 4-chlorophenoxyacetic acid, 4-nitrobenzoic acid, abscisic acid, citric acid, gibberellic acid, gibberellin A13, gibberellin A3, gibberellin A4, gluconic acid, indole-3-acetic acid, indole-3-butanoic acid, oxalic acid, or salicylic acid;
- preferably 1-naphthalene acetic acid, 4-chlorophenoxyacetic acid, abscisic acid, citric acid, gibberellic acid, gibberellin A3, gluconic acid, indole-3-acetic acid, indole-3-butanoic acid, oxalic acid, or salicylic acid;
- more preferably 1-naphthalene acetic acid, 4-chlorophenoxyacetic acid, 4-nitrobenzoic acid, gibberellic acid, gibberellin A3, gluconic acid, indole-3-acetic acid, oxalic acid, salicylic acid, or citric acid; and
- most preferably 1-naphthalene acetic acid or gibberellic acid.

In preferred embodiments, the pendant group is ionically attached to repeat units Y3. In more preferred embodiments, Y3 represents repeat units of formula (III):

wherein:

$R^1$ is a hydrogen atom or methyl;

$R^2$ is the same or different $C_{1-6}$ alkyl; and $A^-$ is a carboxylate anion of an organic acid that is a plant hormone or a phosphorus solubilizer.

In preferred embodiments, $R^1$ is methyl.

In preferred embodiments, both $R^2$ groups are methyl.

As can be seen in the above, in formula (III), the pendant group $A^-$ is a carboxylate anion ($RCOO^-$) of an organic acid ($RCOOH$) that is a plant hormone or phosphorus solubilizer, preferably a plant hormone. Preferably, these organic acids that are a plant hormone or a phosphorus solubilizer are as defined above, including preferred embodiments thereof.

In preferred embodiment, Y3 is a repeat unit obtained by polymerizing the following monomers.

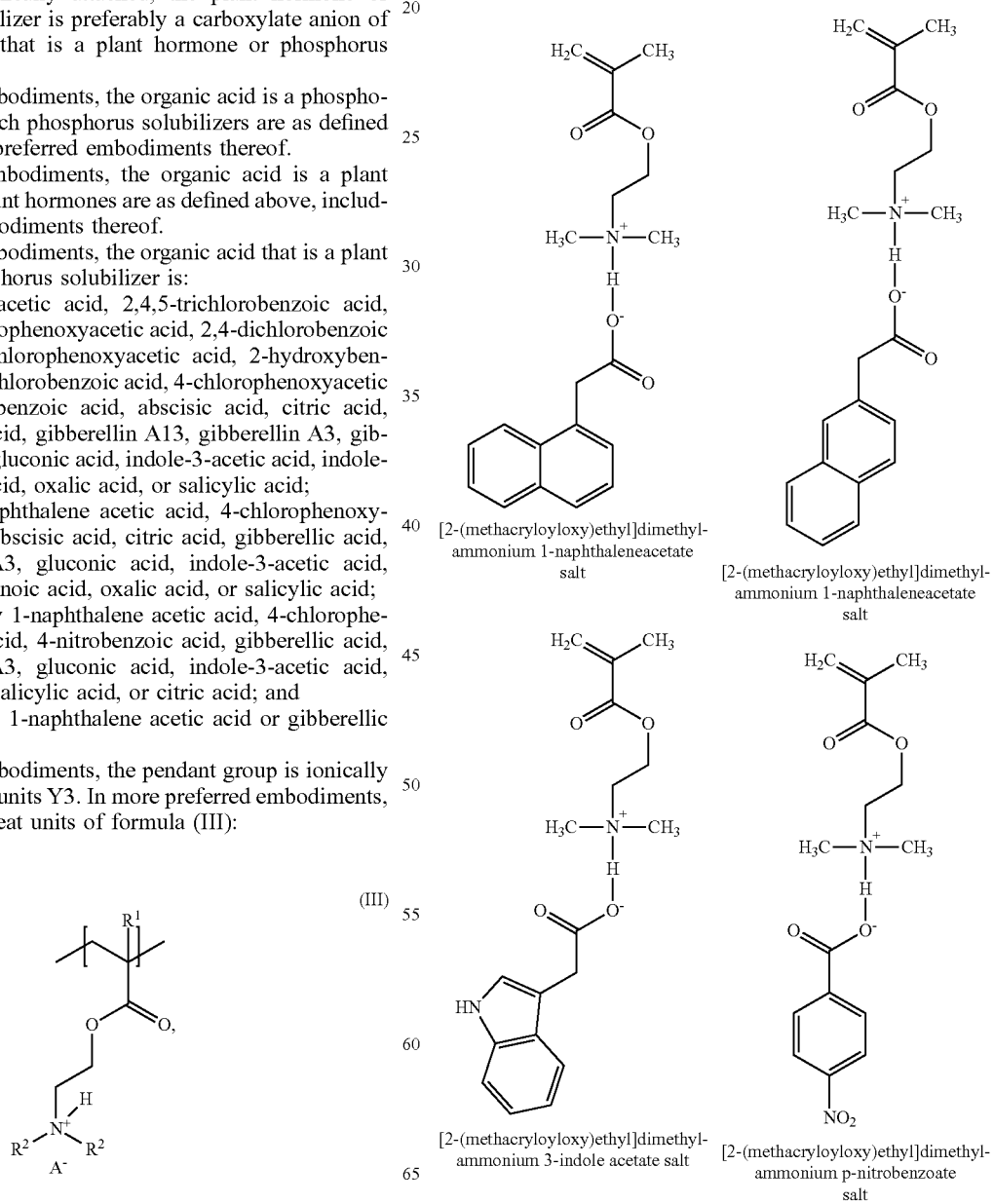

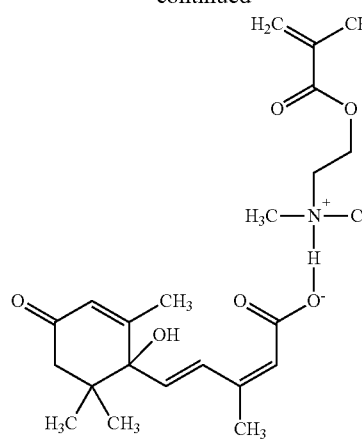

[2-(methacryloyloxy)ethyl]dimethyl-
ammonium abscisicate salt

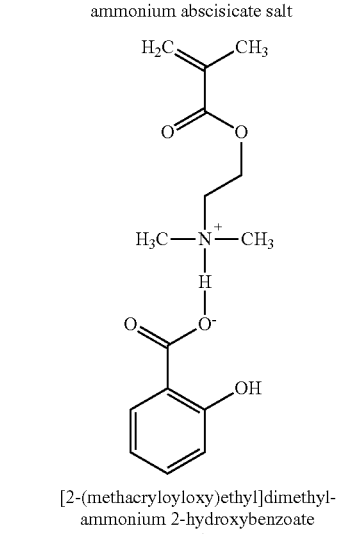

[2-(methacryloyloxy)ethyl]dimethyl-
ammonium 2-hydroxybenzoate
salt

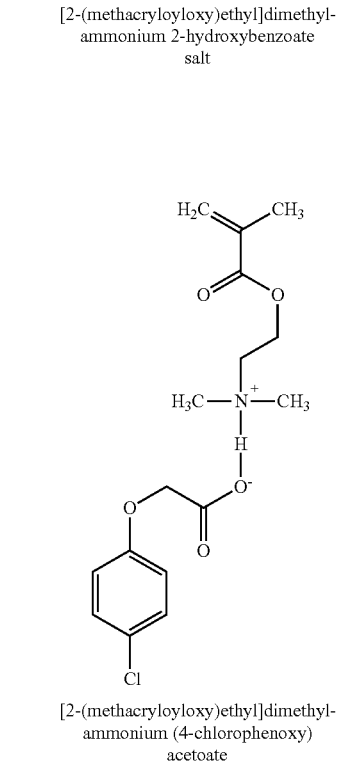

[2-(methacryloyloxy)ethyl]dimethyl-
ammonium (4-chlorophenoxy)
acetoate

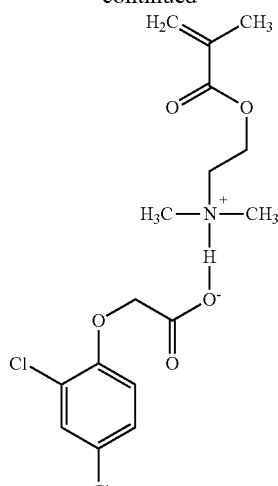

[2-(methacryloyloxy)ethyl]dimethyl-
ammonium (2,4-dichlorophenoxy)
acetoate

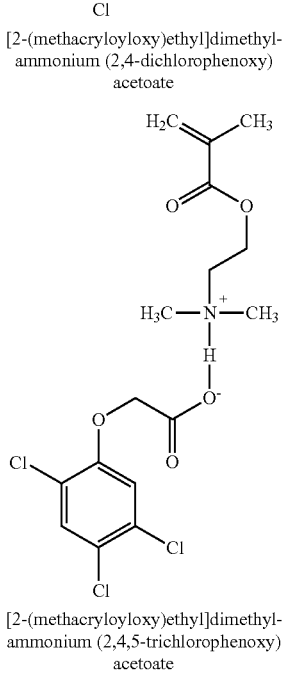

[2-(methacryloyloxy)ethyl]dimethyl-
ammonium (2,4,5-trichlorophenoxy)
acetoate

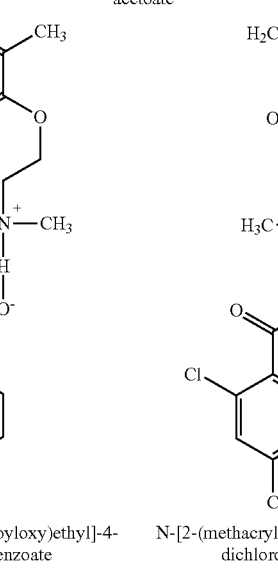

N-[2-(methacryloyloxy)ethyl]-4-
chlorobenzoate

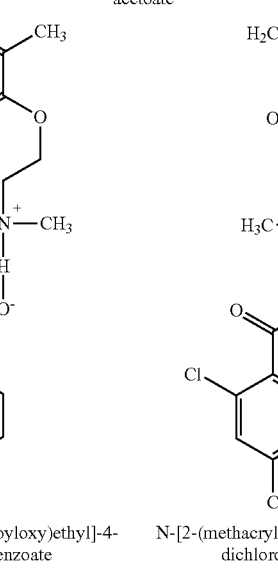

N-[2-(methacryloyloxy)ethyl]-2,4-
dichlorobenzoate

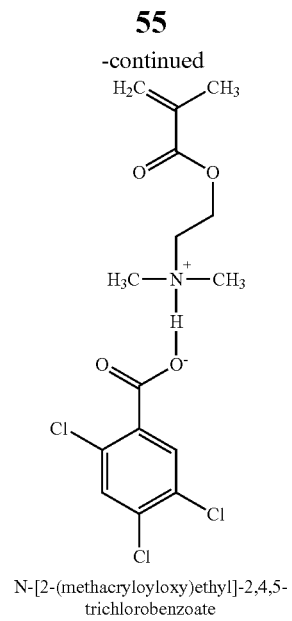

N-[2-(methacryloyloxy)ethyl]-2,4,5-trichlorobenzoate

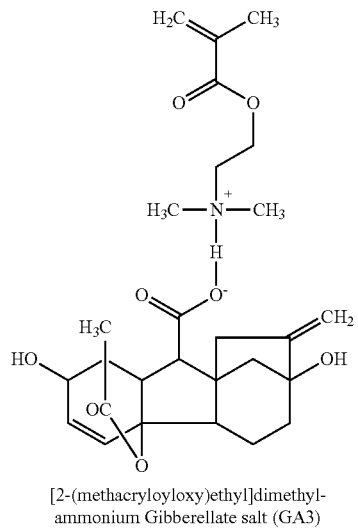

[2-(methacryloyloxy)ethyl]dimethyl-ammonium Gibberellate salt (GA3)

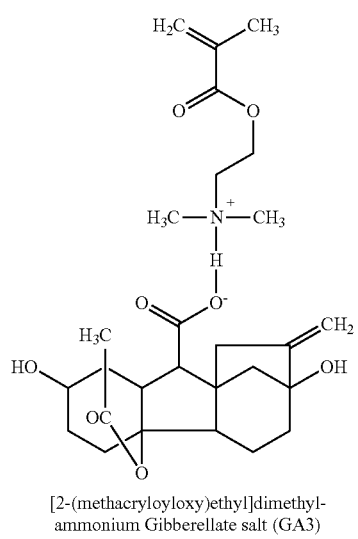

[2-(methacryloyloxy)ethyl]dimethyl-ammonium Gibberellate salt (GA3)

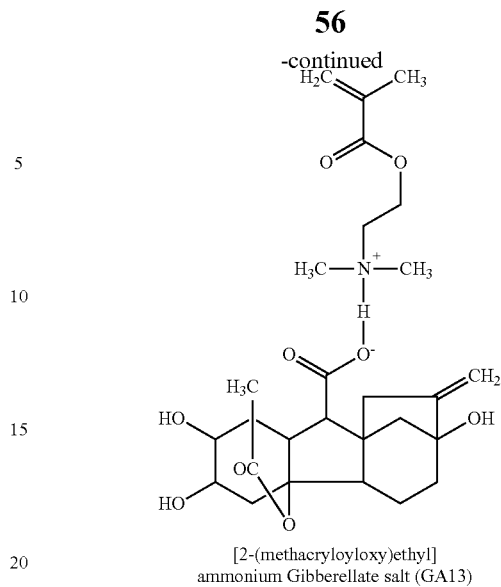

[2-(methacryloyloxy)ethyl] ammonium Gibberellate salt (GA13)

Of note, the structure of the Y3 repeat units obtained by polymerizing the above monomers can easily be deduced from the structure of the monomers as follows:

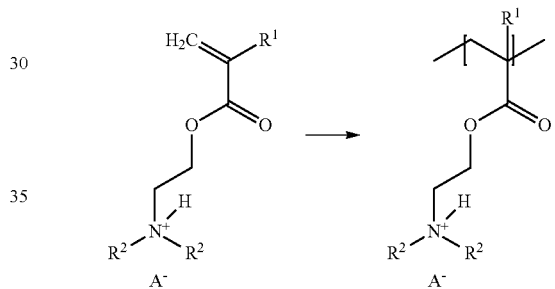

In preferred embodiments, a is about 20 wt % or more, about 25 wt % or more, about 30 wt % or more, about 35 wt % or more, about 39 wt % or more, or about 40 wt % or more; and/or about 65 wt % or less, about 60 wt % or less, about 55 wt % or less, about 50 wt % or less, about 46 wt % or less, or about 45 wt % or less. In embodiments when c is zero, a is preferably about 50 wt %. In embodiments when c is greater than zero, a is preferably between about 35 wt % and about 50 wt % and more preferably between about 39 wt % and about 46 wt %.

In preferred embodiments, b is about 30 wt % or more, about 35 wt % or more, about 40 wt % or more, about 44 wt % or more, or about 45 wt % or more; and/or about 80 wt % or less, about 70 wt % or less, about 65 wt % or less, about 60 wt % or less, about 55 wt % or less, about 50 wt % or less, or about 49 wt % or less. In embodiments when c is zero, b is preferably about 50 wt %. In embodiments when c is greater than zero, b is preferably between about 40 wt % and about 50 wt % and more preferably between about 44 wt % and about 49 wt %.

In preferred embodiments, c is about 0 wt % or more, about 1 wt % or more, about 2 wt % or more, about 3 wt % or more, about 4 wt % or more, about 5 wt % or more; and/or about 30 wt % or less, about 25 wt % or less, about 20 wt % or less, about 17 wt % or less, about 15 wt % or less, about 12 wt % or less, or about 10 wt % or less. In embodiments, c is 0 wt %. In other embodiments, c is greater than 0 wt %.

Preferred copolymers of formula (II) have the following ideal chemical structures:

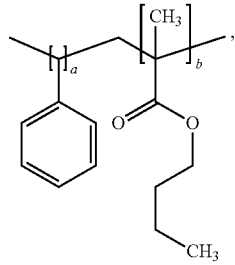
POLY-004 preferably wherein a is about
50 wt % and b is about 50 wt %,

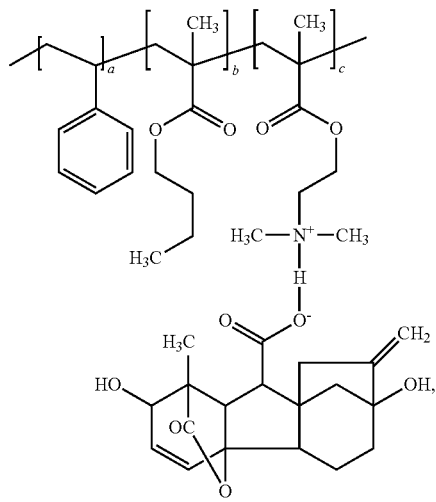
POLY-005/POLY-006 preferably wherein a is about 44 wt %,
b is about 47 wt %, and c is about 9 wt %,
or wherein a is about 39 wt %,
b is about 44 wt %, and c is about 17 wt %,
more preferably wherein a is about 44 wt %,
b is about 7 wt %, and c is about 9 wt %,

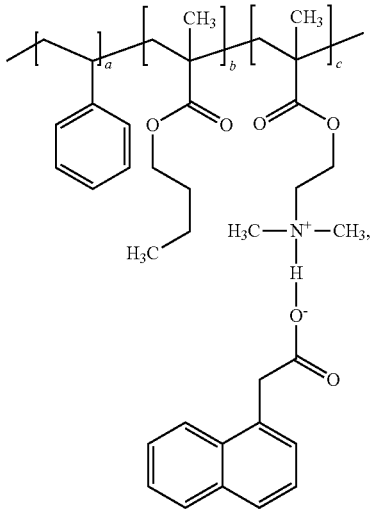
POLY-007/POLY-008 preferably wherein a is about 46 wt %,
b is about 48 wt %, and c is about 6 wt %,
or wherein a is about 41 wt %,
b is about 47 wt %, and c is about 12 wt %,
more preferably wherein a is about 46 wt %,
b is about 48 wt %, and c is about 6 wt %,

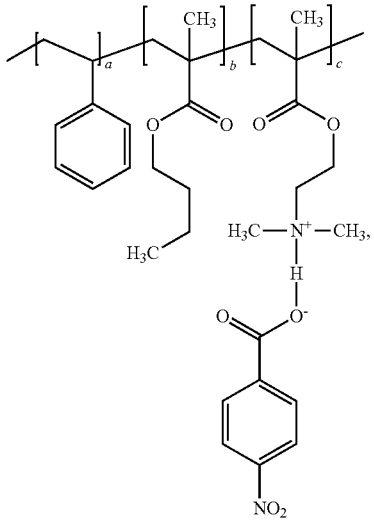
POLY-009 preferably wherein a is about 46 wt %,
b is about 48 wt %, and c is about 6 wt %,

POLY-010

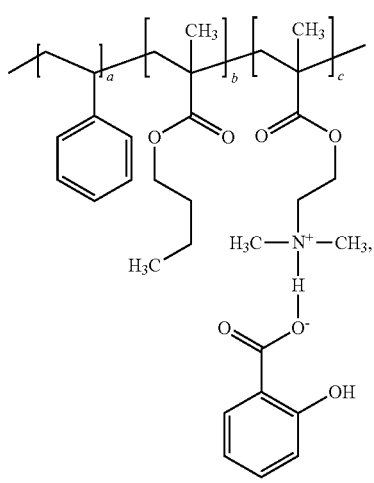

preferably wherein a is about 46 wt %,
b is about 49 wt %, and c is about 5 wt %, or

POLY-011

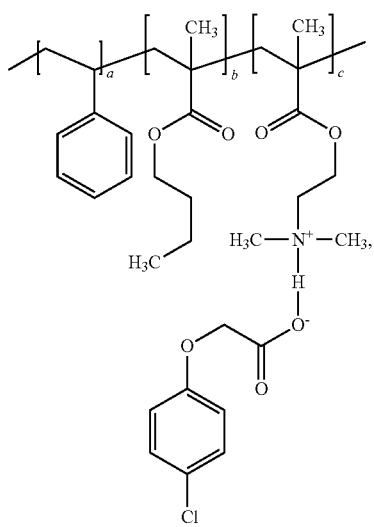

preferably wherein a is about 46 wt %,
b is about 48 wt %, and c is about 6 wt %.

Most preferred copolymers of formula (II) include POLY-004, POLY-005, and POLY-007, preferably POLY-004.

In embodiments, the pendant group is covalently attached to repeat units Y3. In more preferred embodiments, Y3 represents repeat units of formula (IV):

$$\text{(IV)}$$

wherein:

R$^1$ is a hydrogen atom or methyl;

D-C(=O)— is a residue of an organic acid that is a plant hormone or phosphorus solubilizer.

As can be seen in the above, in formula (IV), the pendant group D-C(=O)— is a residue of an organic acid (D-COOH) that is a plant hormone or a phosphorus solubilizer, preferably a plant hormone. Preferably, this organic acid that is a plant hormone or a phosphorus solubilizer are as defined above, including preferred embodiments thereof.

In preferred embodiments, the organic acid is gibberellic acid, indole-3-acetic acid, 1-naphthalene acetic acid, 2-naphthalene acetic acid, 4-nitrobenzoic acid, 4-chlorophenyloxyacetic acid, or salicylic acid.

In preferred embodiments, the repeat unit Y3 of formula (IV) is obtained by polymerization of the following monomer of formula (VI), which can be synthesized by the reacting the monomer of formula (V) with the organic acid in an oxygen atmosphere at temperature around 40° C. in presence of 1,4-dioxolane without catalyst.

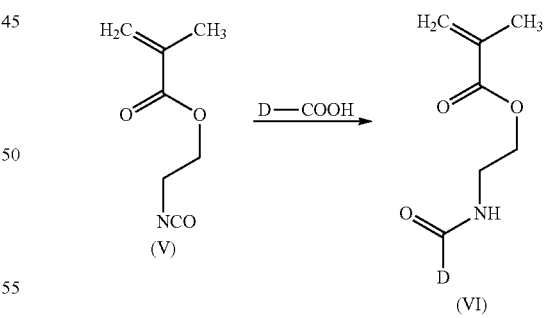

wherein D-COOH is the organic acid that is a plant hormone or a phosphorus solubilizer.

Preferred copolymers of formula (IV) have the following ideal chemical structures:

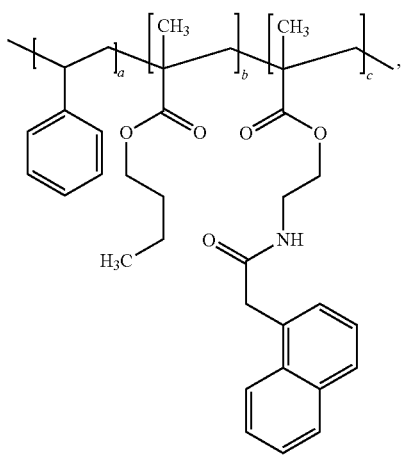

POLY-012 preferably wherein a is about 47 wt %,
b is about 50 wt %, and c is about 3 wt %,

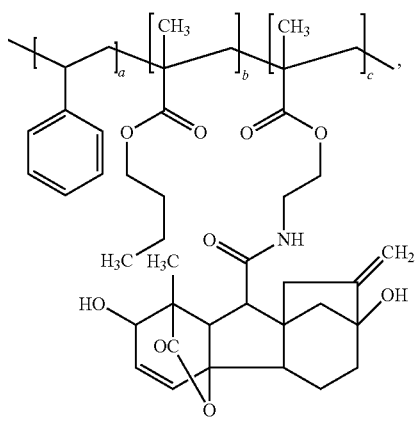

POLY-013 preferably wherein a is about 47 wt %,
b is about 50 wt %, and c is about 3 wt %,

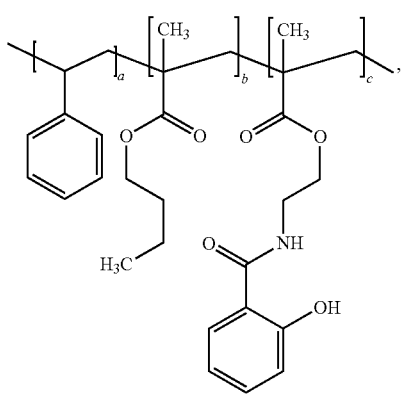

POLY-014 preferably wherein a is about 47 wt %,
b is about 50 wt %, and c is about 3 wt %, or

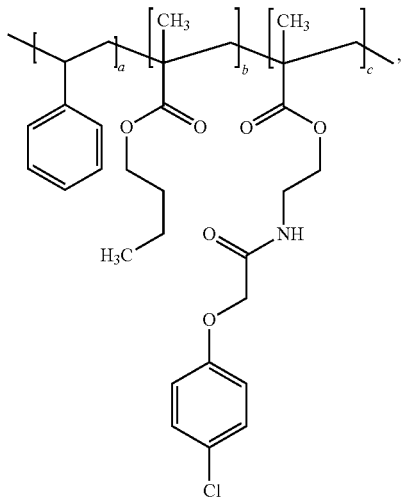

POLY-015 preferably wherein a is about 47 wt %,
b is about 50 wt %, and c is about 3 wt %.

The anticaking layer may comprise a mixture of the above water-insoluble copolymeric nanoparticles.

The water-insoluble copolymeric nanoparticles may comprise a mixture of the above copolymers.

The copolymer for the water-insoluble copolymeric nanoparticles for the anticaking layer can be synthesized, for example, by free radical emulsion copolymerization in an aqueous solution containing anionic and non-ionic surfactants, such as sodium n-dodecyl benzene sulfonate and n-octanol. A pH controlling agent, such as sodium bicarbonate can also be used in the copolymerization to provide a stable polymeric nanoparticle suspension.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure, such as Formulas I to IX, with various substituents ($R^1$, $R^2$, etc.) and various radicals (alkyl, halogen atom, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

For clarity, an organic acid can be represented as RCOOH, in which R is an organic group.

An organic carboxylate salt can be represented as RCOO⁻M⁺, i.e. an organic carboxylate anion (RCOO⁻) with a cation (M⁺), in which R is an organic group.

Since a salt is often conceptualized as the result of an acid-base reaction:

| HA | + | BOH | → | AB | + | H₂O |
| Acid | | Base | | Salt | | Water | wherein A is an anion and B is a cation,
it is often said for simplicity that a given anion (A⁻) is "the carboxylate anion of a given corresponding acid" (HA). This means that the anion (A⁻) corresponds to the following underlined part of the acid: HA. For example, the carboxylate anion of acetic acid (CH₃COOH) is acetate (CH₃COO—).

Herein, a "residue" of an organic acid or a carboxylate anion is a group obtained by covalently attaching an organic acid or a carboxylate anion to another molecule. For example, an organic acid RCOOH can be reacted with a —NCO group to attach the organic acid as follows: —N—C(=O)—R, wherein R—C(=O)— is the residue of the organic acid.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Herein, the terms "alkyl", "alkylene", "alkenyl", "alkenylene", "alkynyl", "alkynylene" and their derivatives (such as alkoxy, alkyleneoxy, etc.) have their ordinary meaning in the art.

For more certainty, herein:

| Term | Definition |
|---|---|
| alkyl | monovalent saturated aliphatic hydrocarbon radical of general formula —C$_n$H$_{2n+1}$ |
| alkylene | bivalent saturated aliphatic hydrocarbon radical of general formula —C$_n$H$_{2n}$— (also called alkanediyl) |

It is to be noted that, unless otherwise specified, the hydrocarbon chains of the above groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, preferably 1, or preferably 2 carbon atoms.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Materials

The following chemicals were used as received without further purification.

CTA Citric Acid, available from Sigma-Aldrich, Canada
CPA 4-Chlorophenoxyacetic Acid, available from Sigma-Aldrich, Canada
GBA Gibberellic Acid, available from Sigma-Aldrich, Canada
GNA Gluconic Acid, available from Sigma-Aldrich, Canada
IAA Indole-3-Acetic Acid, available from Sigma-Aldrich, Canada
NAA 1-Naphthalene Acetic Acid, available from Sigma-Aldrich, Canada
SAA Salicylic Acid, available from Sigma-Aldrich, Canada
BZQ 1,4-benzoquinone, available from Sigma-Aldrich, Canada
DAP Diammonium phosphate fertilizer, available from Phu My Fertilizers, Vungtau, Vietnam
DCD Dicyandiamide 99%, available from Sigma-Aldrich, Canada
DDL Dibutyltin dilaurate, available from Sigma-Aldrich, Canada
DMA 2-(N,N-Dimethylamino)ethyl methacrylate, available from Sigma-Aldrich, Canada
DMF N,N-dimethylformamide, available from Sigma-Aldrich, Canada
DXL 1,4-dioxolane, available from Sigma-Aldrich, Canada
ICM 2-isocyanatoethyl methacrylate, available from Korea Showa Chemicals, Seoul, Korea.
NBA p-Nitrobenzoic Acid, available from Sigma-Aldrich, Canada
NBTPT N-(n-Butyl)thiophosphoric triamide, available from Sigma-Aldrich, Canada.
N-Humus Ureafertilizer coated with humic acid (N: 35% and Humus 7%), available from Ca Mau Fertilizers, Camau, Vietnam
N-46.NANO.C+ Urea fertilizer coated with chitosan (N: 46% and Chitosan 3.5%), available from Ca Mau Fertilizers, Camau, Vietnam
N-46-Plus Urea fertilizer coated with NBTPT and DCD (N: 46%, 230 ppm NBTPT and 950 ppm DCD), available from Ca Mau Fertilizers, Camau, Vietnam
SDS Sodium dodecyl sulfonate, available from Signa Aldrich, Canada
TA Tannic acid, available from Sigma Aldrich, Canada
UREA Urea fertilizer containing 46% nitrogen, available from Ca Mau Fertilizers, Camau, Vietnam Syntheses and Characterization of Copolymeric Nanoparticles Copolymeric nanoparticles were synthesized in a 500 Kg oil heated double wall glass-lined reactor equipped with a water condenser, mechanical stirrer, dropping funnel, thermometer and nitrogen or air inlet.

The products were characterized with a Perkin Elmer® Spectrum Two® FTIR spectrometer.

The particle size of the copolymeric nanoparticles was measured in a dilute water solution using a Brookhaven® NanoBrook® 173Plus particle size analyzer.

The molecular weight of the copolymers was measured using a Waters® size exclusion chromatography column using N,N-dimethylformamide as an eluent and using polystyrene standards.

Example 1—Water-Swellable Copolymeric Nanoparticles POLY-001

The synthesis of copolymeric nanoparticles POLY-001 (as an aqueous suspension) was done by mixing a prepolymer solution, which comprised 236 Kg of deionized water, 39.6 Kg of styrene, 39.6 Kg of n-butylacrylate, 0.82 Kg of acrylic acid, 2.48 Kg of triethoxy vinylsilane, 0.82 Kg of ammonium bicarbonate and 0.82 Kg n-octanol in a 1,000-liter stainless steel tank with a high shear mixer. In a separate smaller tank, a solution of ammonium persulfate free radical initiator was prepared by dissolving 0.42 Kg of ammonium persulfate into 10 Kg deionized water.

One hundred and sixty kilograms of the prepolymer solution were loaded in the reactor. The temperature was slowly raised to 80° C. and the remaining prepolymer solution was added to the reactor using a dosing pump at a rate 32.0 Kg per hour. Simultaneously, the ammonium persulfate solution was also added to the reactor using a dosing pump at a rate of 2.00 Kg per hour.

After both solutions were completely added into the reactor, the polymerization was continued at 80° C. under nitrogen atmosphere and constant stirring for additional 15 hours. Reaction samples were removed from the reactor after 16, 20 and 24 hours to measure the solid weight for monitoring the completeness of the polymerization. After the polymerization was completed, deionized water was added to the reactor to adjust the solid weight to 25%, thus producing a suspension that could directly be used (with optional further dilution as desired) to produce smart N-Fertilizers.

Copolymer POLY-001 was:

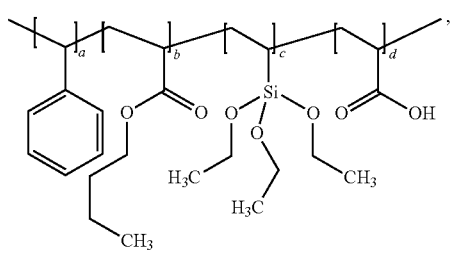

POLY-001 with a, b, c and d being 48 wt %, 48 wt %, 3 wt % and 1 wt %, respectively, based on the total weight of the copolymer.

The glass transition temperature, particle size, and polydispersity of POLY-001 were measured to be 20° C., 92.0 nm and 0.020, respectively.

Figure 2:
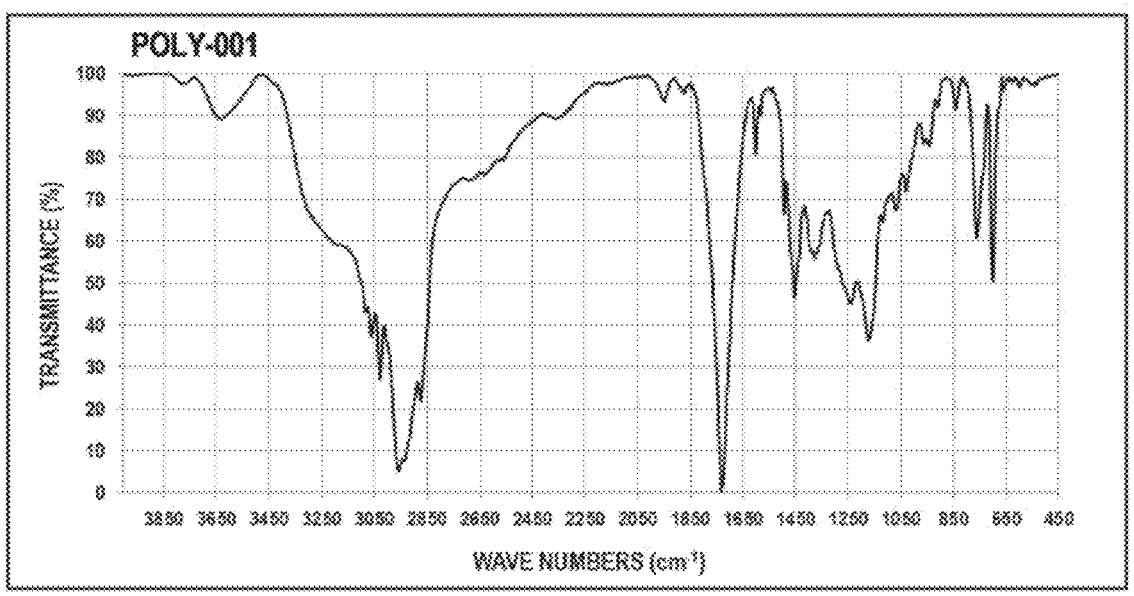
FIG. 2 shows the FTIR spectrum of copolymeric nanoparticles POLY-001 in a KBr pellet.

FIG. 2 shows the FTIR spectrum of copolymeric nanoparticles POLY-001 in a KBr pellet.

Example 2—Water-Insoluble Copolymeric Nanoparticles POLY-004

The synthesis of copolymeric nanoparticles POLY-004 (as an aqueous suspension) was done by mixing a prepolymer solution, which comprised 236 Kg of deionized water, 50.0 Kg of styrene, 50.0 Kg of butyl methacrylate, 0.82 Kg of ammonium bicarbonate and 0.82 Kg n-octanol in a 1,000-liter stainless steel tank with a high shear mixer. In a separate smaller tank, a solution of ammonium persulfate free radical initiator was prepared by dissolving 0.42 Kg of ammonium persulfate into 10 Kg deionized water.

One hundred and sixty kilograms of the prepolymer solution were loaded in the reactor. The temperature was slowly raised to 80° C. and the remaining prepolymer solution was added to the reactor using a dosing pump at a rate 32.0 Kg per hour. Simultaneously, the ammonium persulfate solution was also added to the reactor using a dosing pump at a rate of 2.00 Kg per hour.

After both solutions were completely added into the reactor, the polymerization was continued at 80° C. under nitrogen atmosphere and constant stirring for additional 15 hours. Reaction samples were removed from the reactor after 16, 20 and 24 hours to measure the solid weight for monitoring the completeness of the polymerization. After the polymerization was completed, deionized water was added to the reactor to adjust the solid weight to 25%, thus producing a suspension that could directly be used (with optional further dilution as desired) to produce smart N-Fertilizers.

Copolymer POLY-001 was:

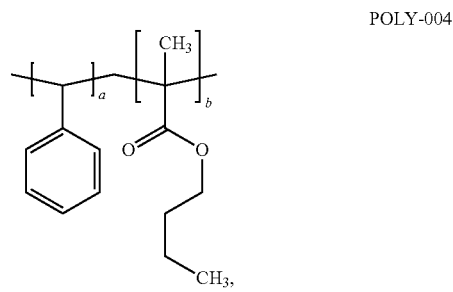

POLY-004 with a and b both being 50 wt %, based on the total weight of the copolymer.

The particle size and polydispersity of POLY-004 were measured to be 79 nm and 0.023, respectively.

Figure 3:
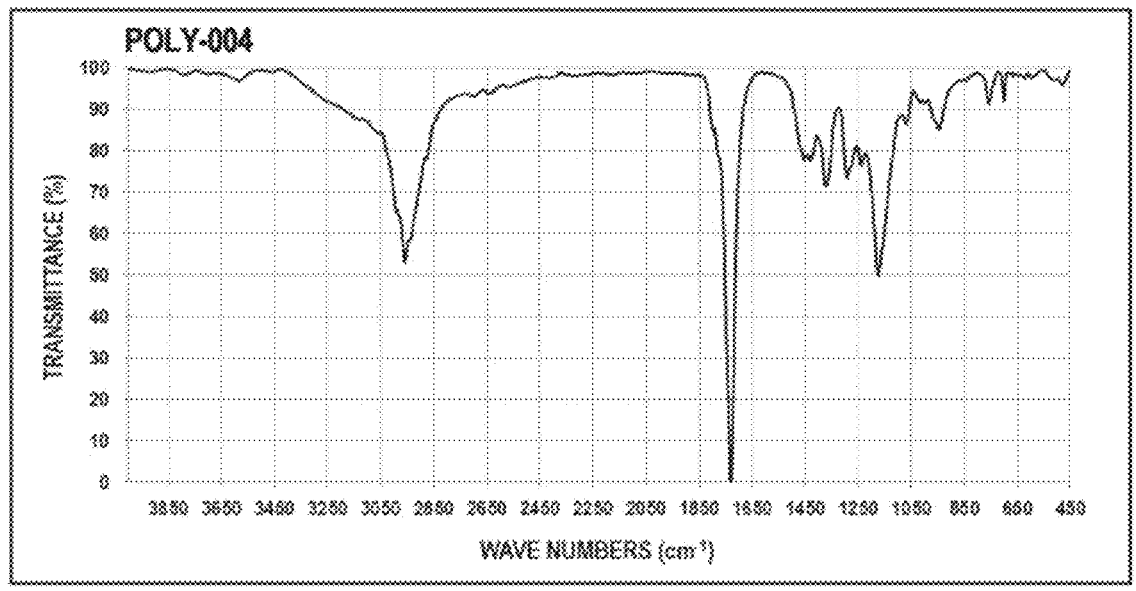
FIG. 3 shows the FTIR spectrum of copolymeric nanoparticles POLY-004 in a KBr pellet.

FIG. 3 shows the FTIR spectrum of copolymeric nanoparticles POLY-004 in a KBr pellet.

Example 3—Water-Insoluble Copolymeric Nanoparticles POLY-005

The synthesis of copolymeric nanoparticles POLY-005 (as an aqueous suspension) was done by mixing a prepolymer solution, which comprised 236 Kg of deionized water, 47.0 Kg of styrene, 50.0 Kg of butyl methacrylate, 3.00 Kg of N,N-dimethylamino ethylmethacrylate, 0.82 Kg of ammonium bicarbonate and 0.82 Kg n-octanol in a 1,000-liter stainless steel tank with a high shear mixer. In a separate smaller tank, a solution of ammonium persulfate free radical initiator was prepared by dissolving 0.42 Kg of ammonium persulfate into 10 Kg deionized water.

One hundred and sixty kilograms of the prepolymer solution were loaded in the reactor. The temperature was slowly raised to 80° C. and the remaining prepolymer solution was added to the reactor using a dosing pump at a rate 32.0 Kg per hour. Simultaneously, the ammonium persulfate solution was also added to the reactor using a dosing pump at a rate of 2.00 Kg per hour.

After both solutions were completely added to the reactor, the polymerization was continued at 80° C. under nitrogen atmosphere and constant stirring for additional 15 hours. Reaction samples were removed from the reactor after 16, 20 and 24 hours to measure the solid weight for monitoring the completeness of the polymerization.

The particle size of the copolymeric nanoparticles was measured to be 1,250 nm with a polydispersity of 0.120.

Then, 6.60 Kg of gibberellic acid were slowly added to the reactor and the stirring continued in the same conditions for an additional 3 hours.

Copolymer POLY-005 was:

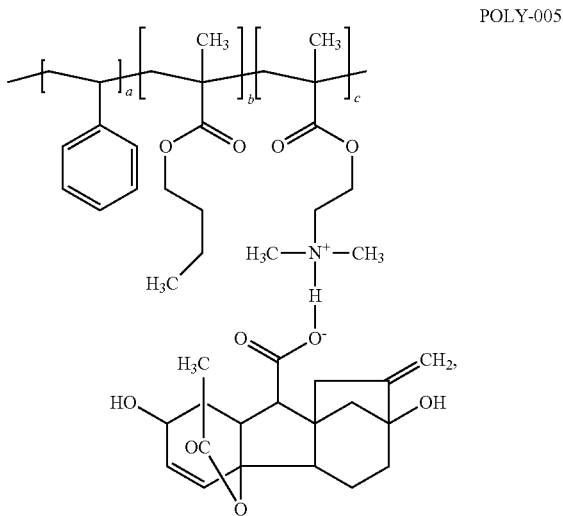

POLY-005 with a being 44 wt %, b being 47 wt %, and c being 9 wt %, based on the total weight of the copolymer.

The particle size and polydispersity were measured to be 109 nm and 0.078, respectively.

Deionized water was added to the reactor to adjust the solid weight to 25%, thus producing a suspension that could directly be used (with optional further dilution as desired) to produce smart N-Fertilizers.

Figure 4:
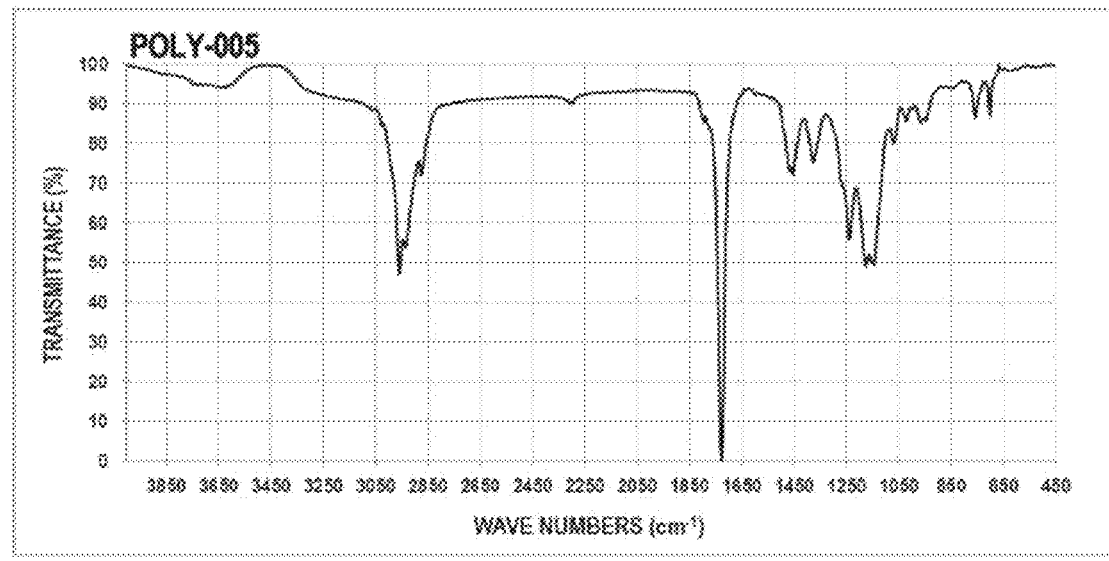
FIG. 4 shows the FTIR spectrum of copolymeric nanoparticles POLY-005 in a KBr pellet.

FIG. 4 shows the FTIR spectrum of copolymeric nanoparticles POLY-005 in a KBr pellet.

Example 4—Water-Insoluble Copolymeric Nanoparticles POLY-007

The synthesis of copolymeric nanoparticles POLY-007 (as an aqueous suspension) was performed in the same manner as in Example 3 with the exception that the monomers were 47.0 Kg of styrene, 50.0 Kg of butyl methacrylate and 3.00 Kg of 2-(dimethylamino)ethyl methacrylate. After 24 hours of polymerization, 3.55 Kg of 1-naphthalene acetic acid were slowly added to the reactor. The reaction was continued, stirring, in the same conditions, for an additional 3 hours. Then, the reactor was cooled to room temperature and deionized water was added to dilute to 25% solid weight, thus producing a suspension that could directly be used (with optional further dilution as desired) to produce smart N-Fertilizers.

Copolymer POLY-007 was:

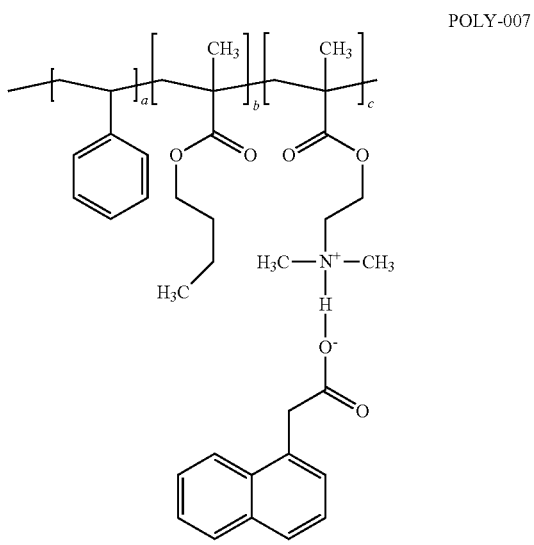

POLY-007 with a being 46 wt %, b being 48 wt %, and c being 6 wt %, based on the total weight of the copolymer, The particle size and polydispersity of POLY-007 were measured to be 76 nm and 0.03, respectively.

Figure 5:
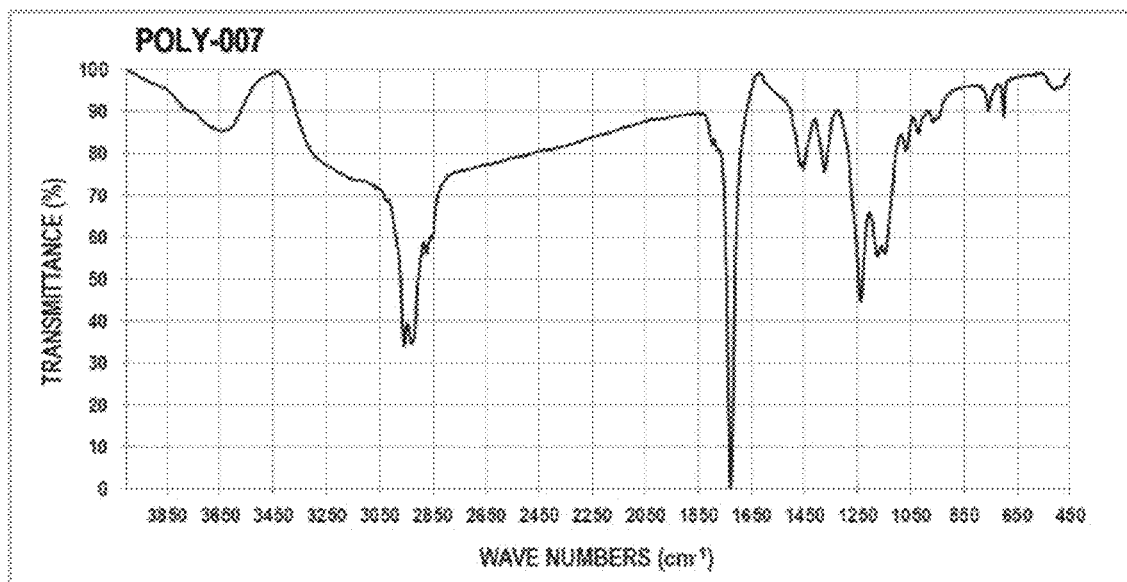
FIG. 5 shows the FTIR spectrum of copolymeric nanoparticles POLY-007 in a KBr pellet.

FIG. 5 shows the FTIR spectrum of copolymeric nanoparticles POLY-007 in a KBr pellet.

Synthesis and Characterization of Tannin Molecules

Example 5—Tannin Molecule Substituted with 5 Acetate Potassium Salt Groups (TAAA)

The synthesis of TAAA (formula provided above in the section entitled "Enzyme Inhibitors") was performed by slowly adding 170 grams of tannic acid in 300 ml of de-ionized water containing 40 grams of potassium hydroxide under nitrogen atmosphere and constant stirring at 80° C. After 1.5 hours, a solution of 170 grams of chloroacetic acid (28%) was slowly dropped into the reaction mixture. The reaction allowed to continue in the same conditions for an additional 5 hours. The obtained solution was ready for production of smart N-Fertilizers.

Figure 6:
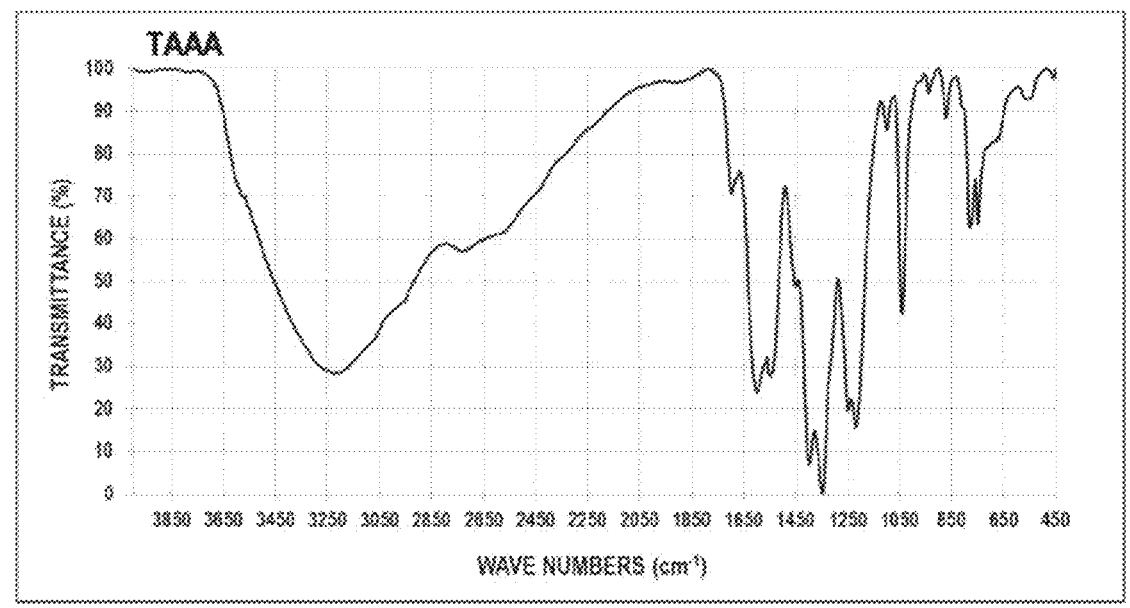
FIG. 6 shows the FTIR spectrum of substituted tannin molecule TAAA of Example 5 in a KBr pellet.

FIG. 6 shows the FTIR spectrum of tannin molecule TAAA of Example 5 in a KBr pellet.

Example 6—Tannin Molecule Substituted with 5 Butane Sulfonic Acid Potassium Salt Groups (TABS)

The synthesis of TABS (formula provided above in the section entitled "Enzyme Inhibitors") was performed by slowly adding 170 grams of tannic acid in 300 ml of de-ionized water containing 40 grams of potassium hydroxide under nitrogen atmosphere and constant stirring at 80° C. After 1.5 hours, a solution of 68.1 grams of 1,4-butane sultone was slowly dropped into the reaction mixture. The reaction allowed to continue in the same conditions for an additional 5 hours. The obtained solution was ready for production of smart N-Fertilizers.

Figure 7:
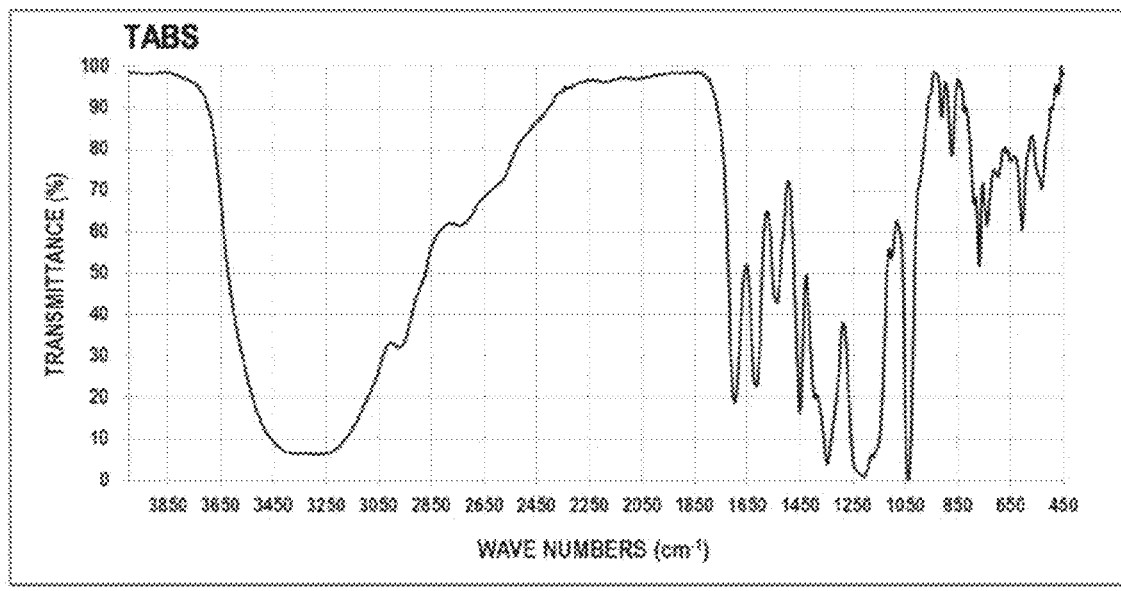
FIG. 7 shows the FTIR spectrum of substituted tannin molecule TABS of Example 6 in a KBr pellet.

FIG. 7 shows the FTIR spectrum of tannin molecule TABS in a KBr pellet.

Example 7—Tannin Molecule Substituted with 5 Ethyl Ammonium 1-Naphthalene Acetic Acid Salt Groups (TANAA)

The synthesis of TANAA (formula provided above in the section entitled "Enzyme Inhibitors") was performed by slowly adding 170 grams of tannic acid in 300 ml of de-ionized water containing 40 grams of potassium hydroxide under nitrogen atmosphere and constant stirring at 80° C. After 1.5 hours, a solution of 58.0 grams of 2-chloroethylamine hydrochloride in 150 ml of water was slowly dropped into the reaction mixture. The reaction was allowed to continue in the same conditions for an additional 5 hours. Then, a solution containing 93.1 grams of 1-naphthalene acetic acid in 300 ml ethanol was slowly added to the reaction mixture. The reaction was allowed to continue, stirring, in the same conditions for an additional 5 hours. The obtained solution was ready for production of smart N-Fertilizers.

Figure 8:
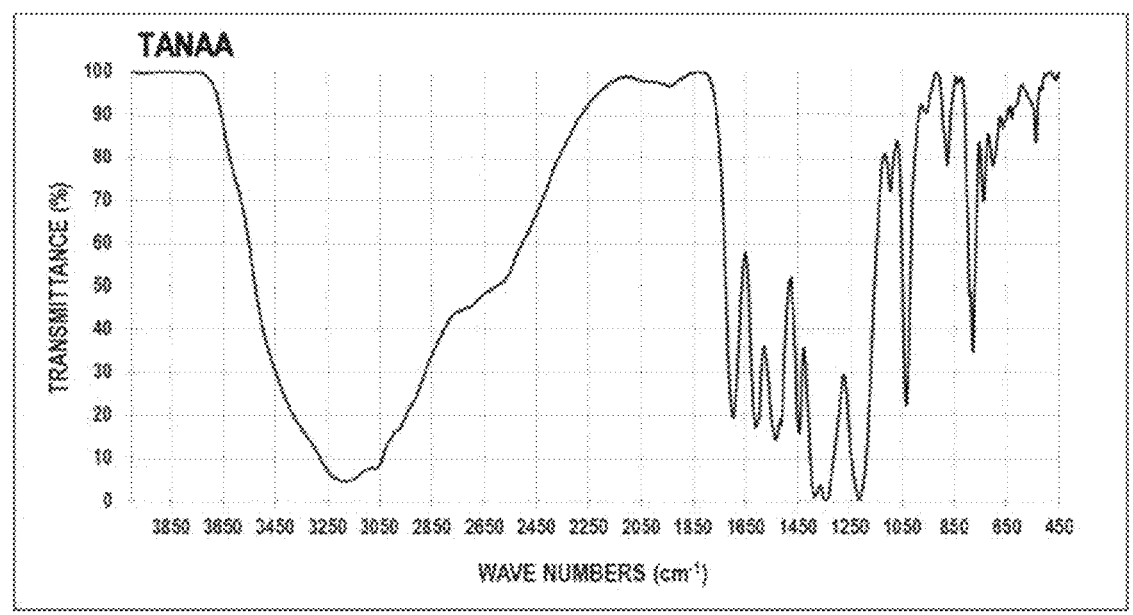
FIG. 8 shows the FTIR spectrum of substituted tannin molecule TANAA of Example 7 in a KBr pellet.

FIG. 8 shows the FTIR spectrum of tannin molecule TANAA in a KBr pellet.

Example 8—Tannin Molecule Substituted with 5 Ethyl Ammonium Gibberelate Salt Groups (TAGA)

The synthesis of TAGA (formula provided above in the section entitled "Enzyme Inhibitors") was performed by slowly adding 170 grams of tannic acid in 300 ml of de-ionized water containing 40 grams of potassium hydroxide under nitrogen atmosphere and constant stirring at 80° C. After 1.5 hours, a solution of 58.0 grams of 2-chloroethylamine hydrochloride in 150 ml of water was slowly dropped into the reaction mixture. The reaction was allowed to continue in the same conditions for an additional 5 hours. Then, a solution containing 173 grams of gibberellic acid in 500 ml ethanol was slowly added to the reaction mixture. The reaction was allowed to continue, stirring, in the same conditions for an additional 5 hours. The obtained solution was ready for production of smart N-Fertilizers.

Figure 9:
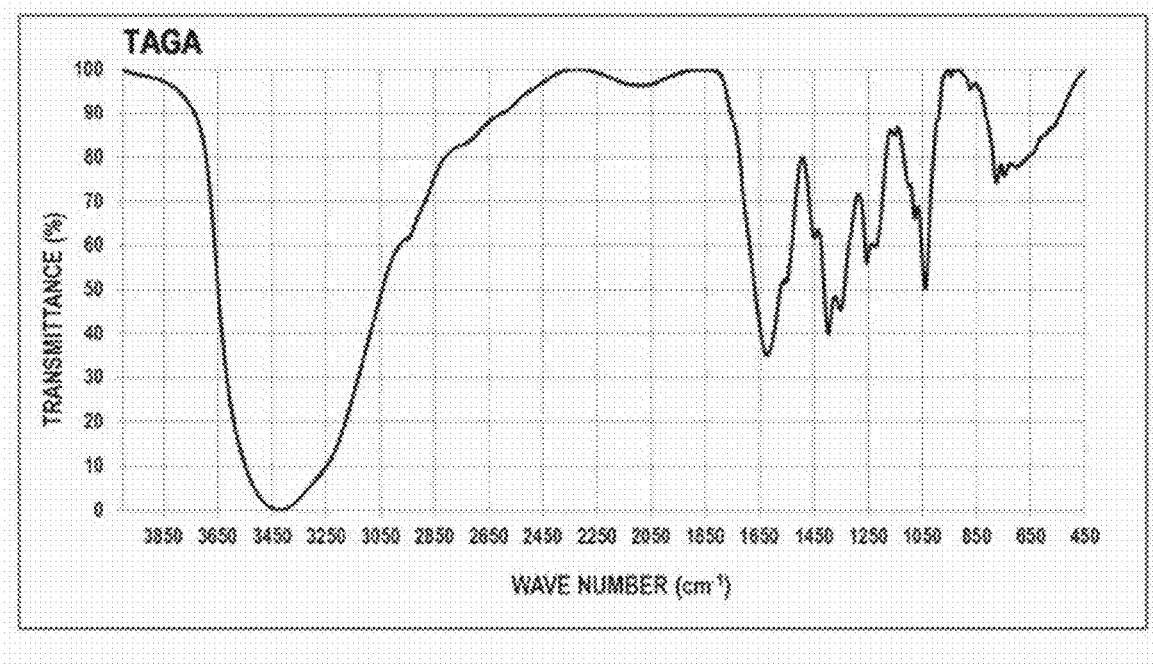
FIG. 9 shows the FTIR spectrum of substituted tannin molecule TAGA of Example 8 in a KBr pellet.

FIG. 9 shows the FTIR spectrum of tannin molecule TAGA in a KBr pellet.

Example 9—Tannin Molecule Substituted with 5 Ethyl Ammonium 4-Nitrobenzoic Acid Salt Groups (TABA, also called TANB)

The synthesis of TABA (formula provided above in the section entitled "Enzyme Inhibitors") was performed by slowly adding 170 grams of tannic acid in 300 ml of de-ionized water containing 40 grams of potassium hydroxide under nitrogen atmosphere and constant stirring at 80° C. After 1.5 hours, a solution of 58.0 grams of 2-chloroethylamine hydrochloride in 150 ml of water was slowly dropped into the reaction mixture. The reaction was allowed to continue in the same conditions for an additional 5 hours. Then, a solution containing 83.6 grams of 4-nitrobenzoic acid in 500 ml ethanol slowly was added to the reaction mixture. The reaction was allowed to continue, stirring, in the same conditions for an additional 5 hours. The obtained solution was ready for production of smart N-Fertilizers.

Figure 10:
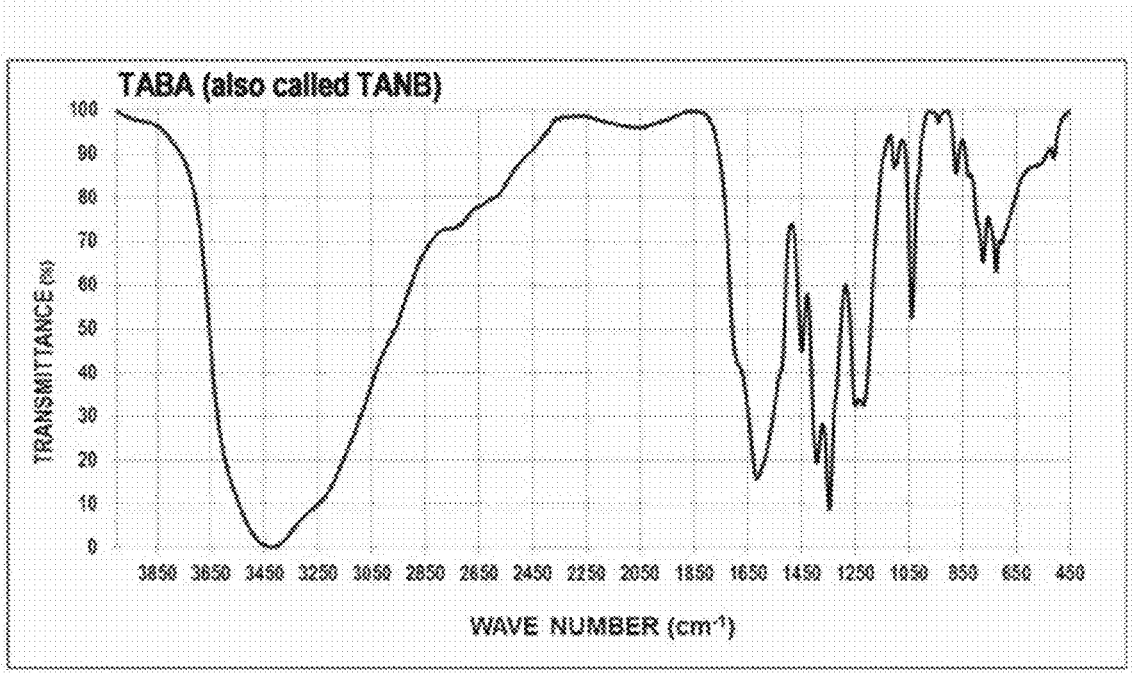
FIG. 10 shows the FTIR spectrum of substituted tannin molecule TABA of Example 9 a KBr pellet.

FIG. 10 shows the FTIR spectrum of tannin molecule TABA in a KBr pellet.

Production and Characterization of Smart N-Fertilizers

Nitrogen containing fertilizer granules were sieved to remove granules (N-Fertilizer) with the size less than 1.5 mm. Then, sieved N-Fertilizer granules (10 Kg) were loaded into a home-built Wurster fluidized bed. The bed temperature was set at 32±2° C. and 20% relative humidity with a hot air stream at a speed of 300 to 400 m³ per hour for 5 minutes to dry the nitrogen containing granules.

Coating of the Organic Functional Layer [104]

Then, an aqueous solution containing 25 wt % of water-swellable copolymeric nanoparticles together with one or more functional organic compound was sprayed from the bottom of the fluidized bed at a rate of 60 grams per minute. The mist was carried by the hot air stream and deposited the copolymeric nanoparticles and functional organic compound(s) onto the surface of the granules (which were floating in the hot air stream). The process was continued until the desired thickness for the organic functional layer [104] was reached.

Then, the spraying was stopped, while the granules remained floating in the hot air stream for an additional 10 minutes in the same conditions before coating the next layer.

Coating of the Controlled Release Layer [106]

The coating of the controlled release layer onto the surface of the nitrogen containing granules covered with the organic functional release layer was done in the same manner as coating the organic functional layer with the exception that the aqueous solution contained water-swellable copolymeric nanoparticles (25 wt %) only (i.e. no functional organic compound was present).

Then, the spraying was stopped, while the granules remained floating in the hot air stream for an additional 10 minutes in the same conditions before coating the next layer.

Coating of the Anticaking Layer [108]

The coating of the anticaking layer onto the surface of the controlled release layer was done in the same manner as coating the controlled release layer with the exception that the aqueous solution contained only water-insoluble copolymeric nanoparticles (25 wt %) and that temperature of the fluid bed was increased to 45° C.

Then, the spraying was stopped, while the granules remained floating in the hot air stream for an additional 20 minutes in the same conditions to remove water.

Determination of Urea Release

For measuring urea release, 4 g of Smart N-Fertilizer were immersed in 400 mL water in a glass bottle and stored in an oven at 30° C. At specific times, 5 mL sample solution was collected for high performance liquid chromatography (HPLC) analysis. The HPLC apparatus was equipped with a Waters 2414 Refractive Index Detector and a XSelect column with water eluent. The sample solution was filtered through a 0.2 µm filter and injected into the HPLC system. By comparing the urea peak with calibration curves, the urea concentration of the sample solution could be determined.

To prepare the calibration curves, standard urea was dissolved in water to obtain two stock solutions with concentrations of 1000 ppm and 10,000 ppm. Two sets of standard urea solutions were prepared for plotting the calibration curves as described.

The percentage of urea release is calculated using the equation:

$$\% \text{ Cumulative Release of Urea} = M_{release}/M_{total\ release} \times 100$$

wherein $M_{release}$ is the weight of urea released in the aqueous solution at a specific time and $M_{total\ release}$ is the maximum weight of urea released in the aqueous solution.

To determine the $M_{total\ release}$ value, coated fertilizer granules were ground to a fine powder, which was then dissolved in water. The concentration of urea in the obtained solution was determined using the HPLC system.

Determination of the Organic Compound Cumulative Release 24 g Smart N-Fertilizers were immersed in 200 mL water in a glass bottle that was stored in an oven at 30° C. After specific periods of time, 5 mL sample solution was collected for UV-VIS spectroscopy analysis using a Jasco V-670 absorption spectrometer. The absorption intensity at a particular wavelength was compared with a calibration curve to calculate the concentration of organic compound released in the initial solution.

The percentage of organic compound release was calculated using the equation:

% Cumulative Release of Organic Compound=$M$release/$M$total release×100 wherein Mrelease is the weight of analyte released in the aqueous solution at a specific times and Mtotal release is the maximum weight of analyte released in the aqueous solution.

Coated granules were ground to a fine powder and then dissolved in water for determining the maximum weight of water-soluble analytes (Mtotal release) using UV-VIS absorption spectroscopy.

Examples 10 to 39—Smart N-Fertilizers with Different Organic Functional Layers and Anticaking Layers The following Smart N-Fertilizers were produced.

| Example | Name of fertilizer | Core 102 | Layer 104 | Layer 106 | Layer 108 |
|---|---|---|---|---|---|
| 10 | N0503 | UREA | NONE | POLY-001 (5%) | POLY-004 (3%) |
| 11 | N0703 | UREA | NONE | POLY-001 (7%) | POLY-004 (3%) |
| 12 | N1003 | UREA | NONE | POLY-001 (10%) | POLY-004 (3%) |
| 13 | DAP0503 | DAP | NONE | POLY-001 (5%) | POLY-004 (3%) |
| 14 | NH0503 | UREA | HUMUS (7%) | POLY-001 (5%) | POLY-004 (3%) |
| 15 | NH0703 | UREA | HUMUS (7%) | POLY-001 (7%) | POLY-004 (3%) |
| 16 | NH1003 | UREA | HUMUS (7%) | POLY-001 (10%) | POLY-004 (3%) |
| 17 | NH0703GA | UREA | HUMUS (7%) | POLY-001 (7%) | POLY-005 (3%) |
| 18 | NH0703NAA | UREA | HUMUS (7%) | POLY-001 (7%) | POLY-007 (3%) |
| 19 | NC0503 | UREA | CHITOSAN (3%) | POLY-001 (5%) | POLY-004 (3%) |
| 20 | NC0703 | UREA | CHITOSAN (3%) | POLY-001 (7%) | POLY-004 (3%) |
| 21 | NBD0503 | UREA | NBTPT (230 ppm) DCD (950 ppm) | POLY-001 (5%) | POLY-004 (3%) |
| 22 | NBD0703 | UREA | NBTPT (230 ppm) DCD (950 ppm) | POLY-001 (7%) | POLY-004 (3%) |
| 23 | NBD0503GA | UREA | NBTPT (230 ppm) DCD (950 ppm) | POLY-001 (5%) | POLY-005 (3%) |
| 24 | NBD0503NAA | UREA | NBTPT (230 ppm) DCD (950 ppm) | POLY-001 (5%) | POLY-007 (3%) |
| 25 | NTA0503 | UREA | TA (1%) | POLY-001 (5%) | POLY-004 (3%) |
| 26 | NTA0703 | UREA | TA (1%) | POLY-001 (7%) | POLY-004 (3%) |
| 27 | NTANAA0503 | UREA | TANAA (1%) | POLY-001 (5%) | POLY-004 (3%) |
| 28 | NTAGA0503 | UREA | TAGA (1%) | POLY-001 (5%) | POLY-004 (3%) |
| 29 | NTABS0503 | UREA | TABS (1%) | POLY-001 (5%) | POLY-004 (3%) |
| 30 | NTABA0503 | UREA | TABA (1%) | POLY-001 (5%) | POLY-004 (3%) |
| 31 | NTAAA0503 | UREA | TAAA (1% | POLY-001 (5%) | POLY-004 (3%) |
| 32 | DAPSDS0503 | DAP | SDS (3%) POLY-001 (3%) | POLY-001 (5%) | POLY-004 (3%) |
| 33 | DAPTA0503 | DAP | TA (3%) POLY-001 (3%) | POLY-001 (5%) | POLY-004 (3%) |
| 34 | DAPTAAA0503 | DAP | TAAA (3%) POLY-001 (1%) | POLY-001 (5%) | POLY-004 (3%) |
| 35 | DAPTABS0503 | DAP | TABS (3%) POLY-001 (1%) | POLY-001 (5%) | POLY-004 (3%) |
| 36 | DAPTANAA0503 | DAP | TANAA (3%) POLY-001 (1%) | POLY-001 (5%) | POLY-004 (3%) |
| 37 | DAPTAGA0503 | DAP | TAGA (3%) POLY-001 (1%) | POLY-001 (5%) | POLY-004 (3%) |
| 38 | DAPTABA0503 | DAP | TABA (3%) POLY-001 (1%) | POLY-001 (5%) | POLY-004 (3%) |
| 39 | DAPTAAA0503GA | DAP | TAAA (3%) POLY-001 (1%) | POLY-001 (5%) | POLY-005 (3%) |
| 40 | DAPTAAA0503NAA | DAP | TAAA (3%) POLY-001 (1%) | POLY-001 (5%) | POLY-007 (3%) |

N.B. The values in parentheses in the above table are the thicknesses (i.e. coating weight) of the various layers. When there are two values given for a given layer (e.g. layer 104 of Ex. 32 to 40), each value represents the thickness of the coating that would be obtained if only the component accompanied by the value was present. For example, in Ex. 40, the entry "TAAA (3%) POLY-001 (1%)" under Layer 104 means that layer 104 has a total thickness of 4%, 75% of which is constituted of TAAA (thus equivalent to a TAAA layer with a 3% thickness) and 25% of which is constituted of POLY-001 (thus equivalent to a POLY-001 layer with a 1% thickness).

Figure 11:
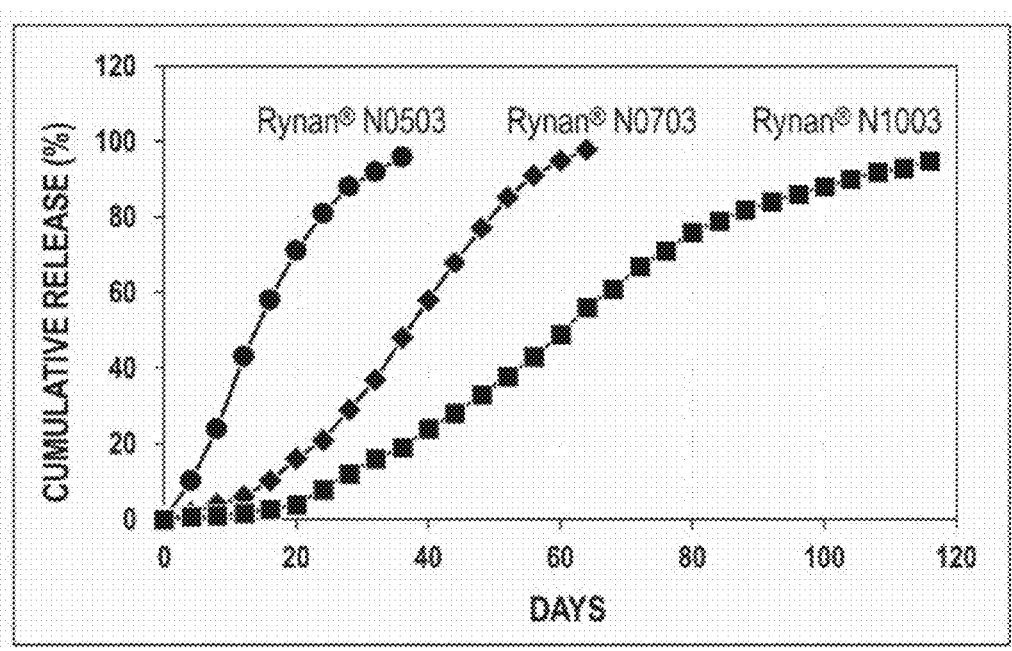
FIG. 11 shows the cumulative urea release from the fertilizers of Examples 10, 11 and 12.

FIG. 11 shows the cumulative urea release from the fertilizers of Examples 10, 11 and 12. It can be seen that increasing the thickness of the controlled release layer 106 (5, 7, and 10% in Examples 10, 11 and 12, respectively) reduces the urea release rate.

Figure 12:
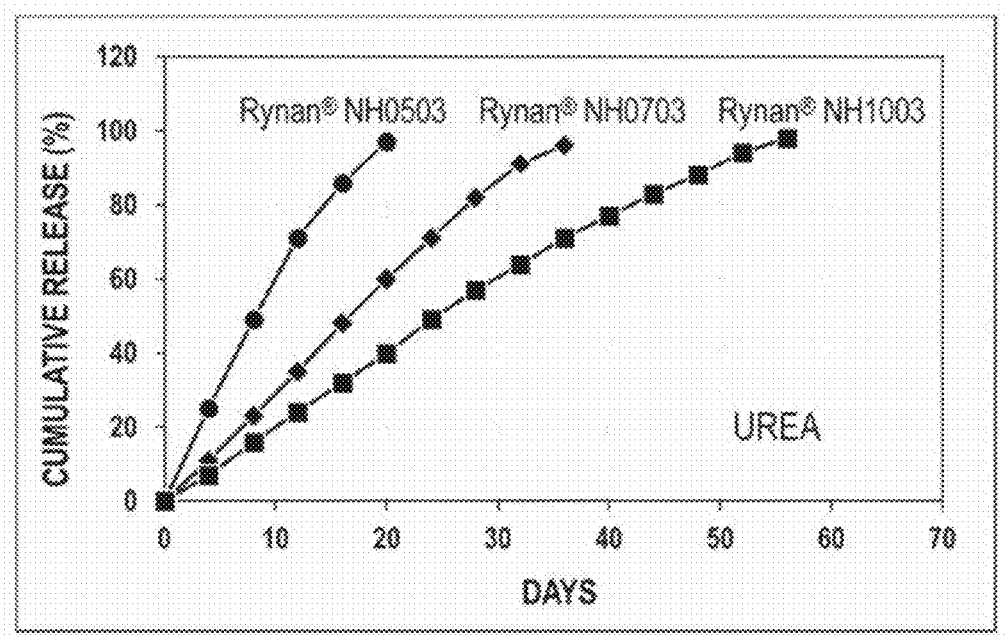
FIG. 12 shows the cumulative urea release from the fertilizers of Examples 14, 15 and 16.

FIG. 12 shows the cumulative urea release from the fertilizers of Examples 14, 15 and 16. Again, it can be seen that increasing the thickness of the controlled release layer 106 (5, 7, and 10% in Examples 14, 15 and 16, respectively) reduces the urea release rate. Comparing FIGS. 11 and 12, it can be seen that the presence of a humus layer (layer 104) significantly increased (in fact almost doubled) the urea release rate.

Figure 13:
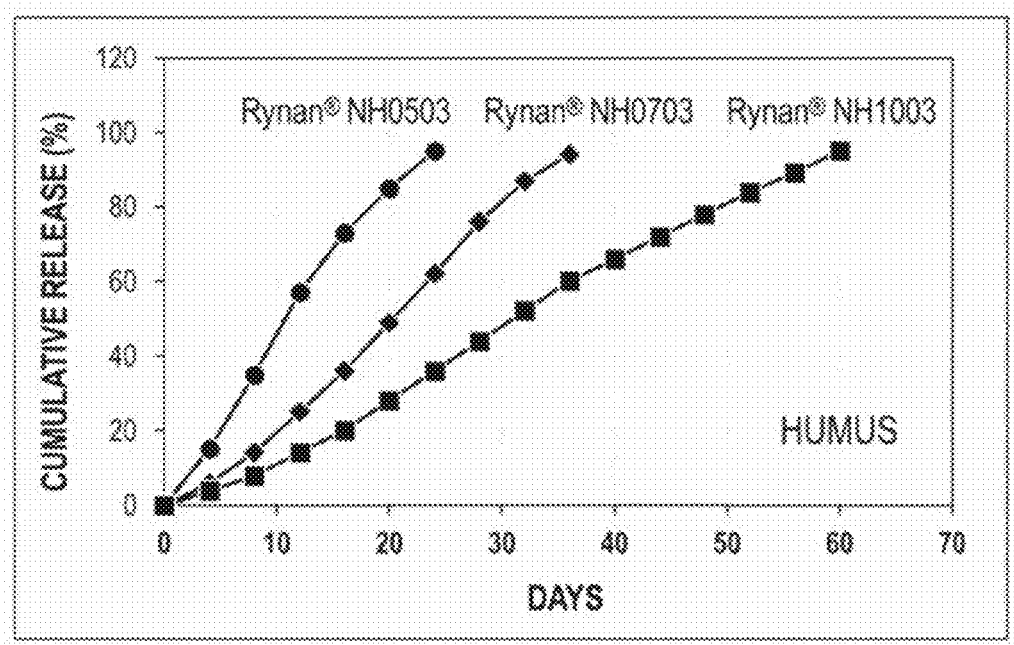
FIG. 13 shows the cumulative humus release from the fertilizers of Examples 14, 15 and 16.

FIG. 13 shows the cumulative humus release from the fertilizers of Examples 14, 15 and 16. Again, increasing the thickness of the controlled release layer reduces the humus release rate.

Figure 14:
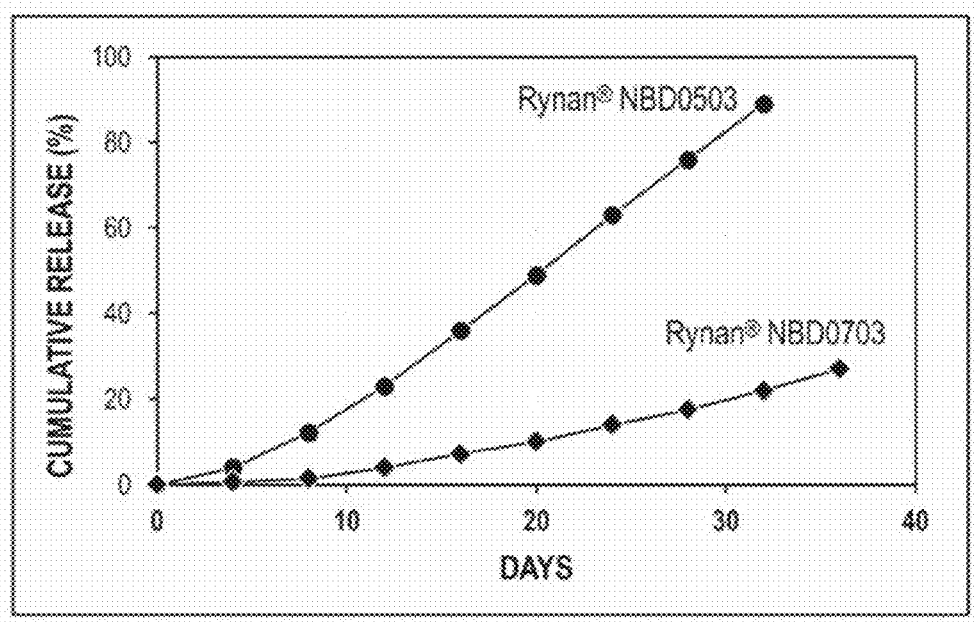
FIG. 14 shows the cumulative urea release from the fertilizers of Examples 21 and 22.

FIG. 14 shows the cumulative urea release from the fertilizers of Examples 21 and 22. Again, it can be seen that increasing the thickness of the controlled release layer 106 (5 and 7% in Examples 21 and 22, respectively) reduces the urea release rate. Comparing FIGS. 11 and 14, it can be seen that the presence of a NBTPT/DCD layer (layer 104) does not significantly change the urea release rate.

Examples 41 to 48—Growing *Brassica integrifolia*

Fertilizers comprising different functional layers were used for growing *Brassica integrifolia*. The experiments were done in plastic planting pots containing 5 Kg of a growth media comprising 50% coconut fibers and 50% topsoil. The N, $P_2O_5$ and $K_2O$ contents in 100 g of the growth media were 7.7 mg, 32 mg and 34 mg, respectively. Ten grams of urea were buried in the growth media at around 3 cm depth as a comparative example (Example 41). Alternatively, 10 grams of various smart N-fertilizers comprising different organic functional layer 104 were buried into the growth media at around 3 cm depth (Examples 42 and following). Then, ten seeds of *Brassica integrifolia* (also called English spinach) were placed in each planting pot. The planting pots were placed outdoor and wetted with 200 ml water every day.

Figure 15:
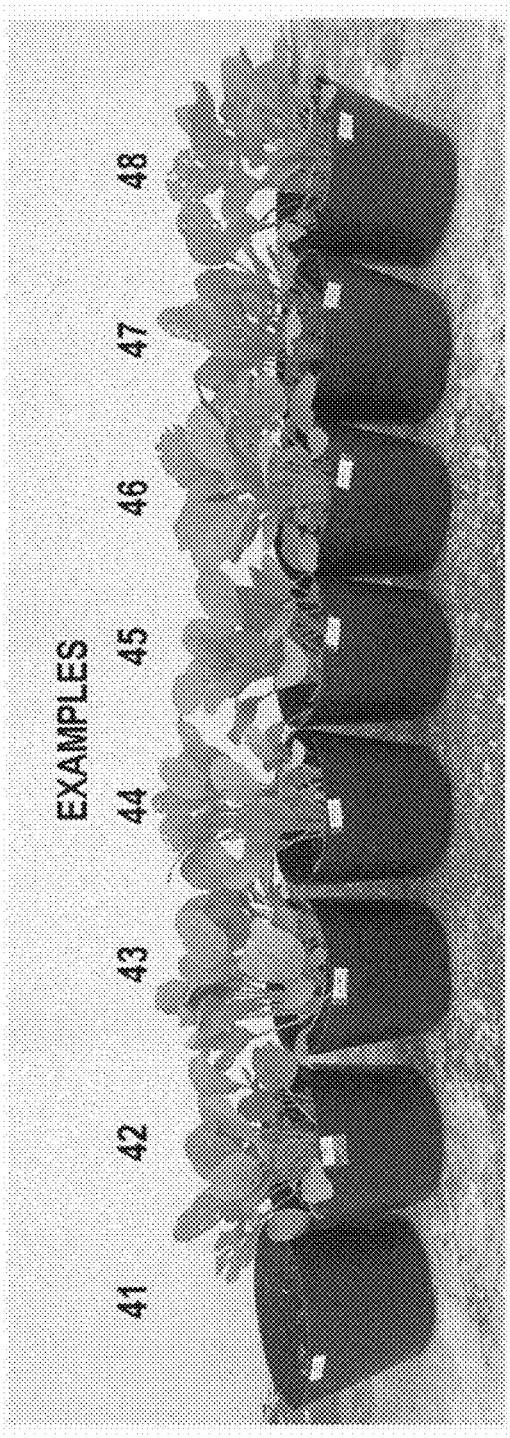
FIG. 15 shows the *Brassica integrifolia* plants grown in Examples 41 to 48, 31 days after planting.

The table below shows the height, leaf length, leaf width, weight of 6 plants per pot and the total yield of *Brassica integrifolia* on day 31 after planting. FIG. 15 shows the *Brassica integrifolia* plants grown in Examples 41 to 48, 31 days after planting.

| Examples | Fertilizers | Height (cm) | Leaf length (cm) | Leaf width (cm) | Weight of 6 plants (gram) | Total yield (gram) |
| --- | --- | --- | --- | --- | --- | --- |
| 41 (comparative) | Urea | 4.90 | 2.00 | 1.00 | 5 | 5 |
| 42 | N0503 from Example 10 | 26.9 | 12.1 | 8.00 | 140 | 301 |
| 43 | NH0503 from Example 14 | 30.1 | 15.4 | 9.60 | 279 | 430 |
| 44 | NH0703GA from Example 17 | 27.3 | 13.6 | 8.30 | 195 | 326 |
| 45 | NH0703NAA from Example 18 | 29.0 | 14.2 | 8.70 | 241 | 350 |
| 46 | NBD0503 from Example 21 | 27.0 | 13.0 | 8.50 | 202 | 358 |
| 47 | NBD0503GA from Example 23 | 28.3 | 12.6 | 8.40 | 208 | 413 |
| 48 | NBD0503NAA from Example 24 | 26.2 | 11.4 | 7.70 | 173 | 273 |

The fertilizers of the invention produced significantly larger plants in a much higher yield than the plain urea fertilizer.

Examples 57 to 61—Growing *Brassica integrifolia*

Smart N-Fertilizers with different organic functional layer comprising tannic acid and its modifiers were used for growing *Brassica integrifolia*. These experiments were carried out as described above for Examples 42 to 48.

Figure 16:
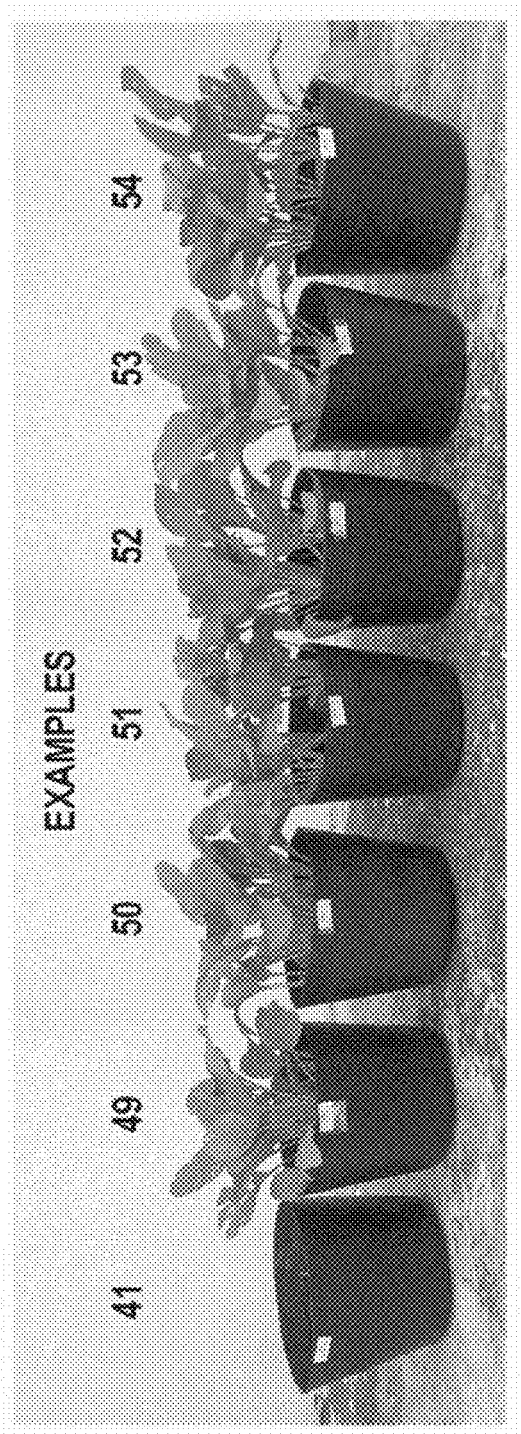
FIG. 16 shows the *Brassica integrifolia* plants grown in Examples 41 and 49-54, 31 days after planting.

The table below shows the height, leaf length, leaf width, weight of 6 plants, and total yield of *Brassica integrifolia* on day 31 after planting. FIG. 16 shows the *Brassica integrifolia* plants grown in Examples 41 (comparative) and Examples 49-54, 31 days after planting.

| Examples | Fertilizers | Height (cm) | Leaf length (cm) | Leaf width (cm) | Weight of 6 plants (gram) | Total yield (gram) |
| --- | --- | --- | --- | --- | --- | --- |
| 41 (comparative) | Urea | 4.90 | 2.00 | 1.00 | 5 | 5 |

| Examples | Fertilizers | Height (cm) | Leaf length (cm) | Leaf width (cm) | Weight of 6 plants (gram) | Total yield (gram) |
|---|---|---|---|---|---|---|
| 49 | N0503 from Example 10 | 29.2 | 14.8 | 9.50 | 140 | 301 |
| 50 | NTA0503 from Example 25 | 33.0 | 15.4 | 10.0 | 286 | 559 |
| 51 | NTANAA0503 from Example 27 | 28.2 | 13.0 | 8.50 | 217 | 398 |
| 52 | NTABS0503 from Example 29 | 31.1 | 14.6 | 9.10 | 233 | 433 |
| 53 | NTABA0503 from Example 30 | 31.1 | 15.8 | 10.5 | 293 | 546 |
| 54 | NTAAA0503 from Example 31 | 32.6 | 14.4 | 9.30 | 273 | 474 |

The fertilizers of the invention produced significantly larger plants in a much higher yield than the plain urea fertilizer.

Examples 55 to 64—Growing *Brassica INTEGRIFOLIA*

Smart N-Fertilizers with different organic functional layer were used for growing *Brassica integrifolia*. These experiments were carried out as described above for Examples 42 to 48, with the exception of Example 55 (comparative), in which ten grams of DAP were buried in the growth media at around 3 cm depth as a comparative example.

Figure 17:
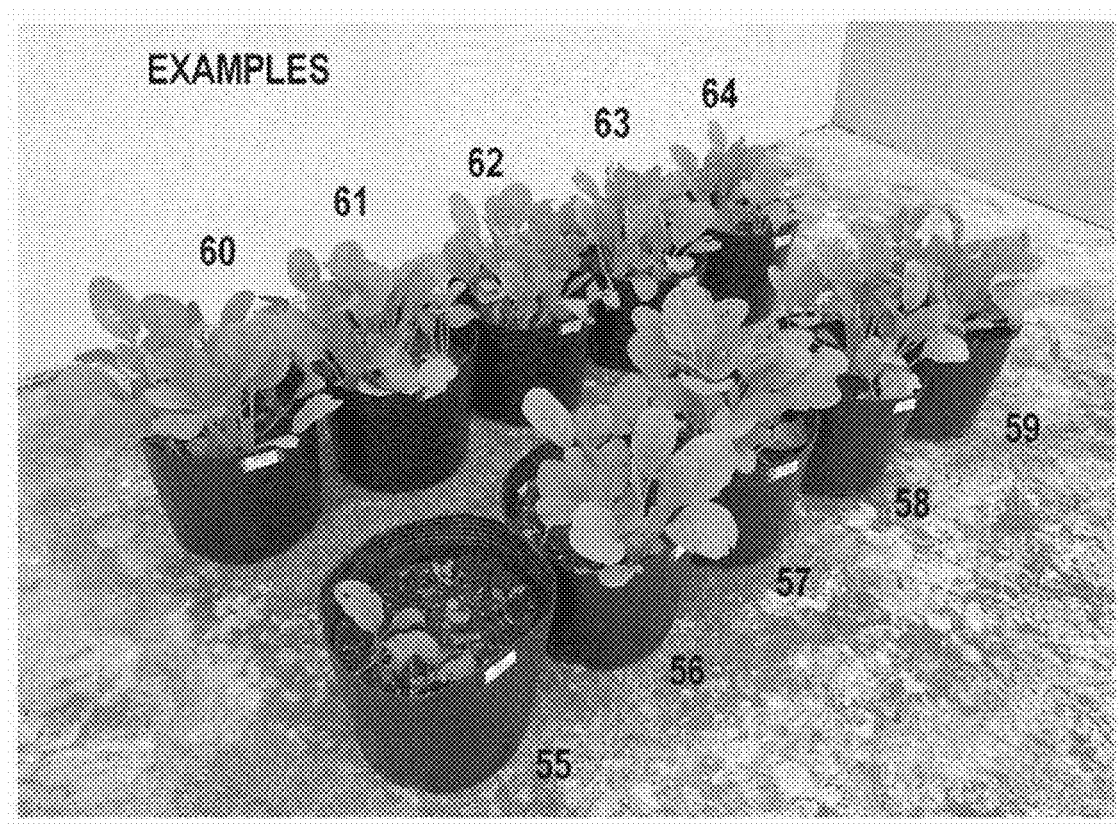
FIG. 17 shows the *Brassica integrifolia* plants grown in Examples 55 to 64 days after planting.

The table below shows the height, leaf length, leaf width, weight of 6 plants, and total yield of *Brassica integrifolia* on day 31 after planting. FIG. 17 shows the *Brassica integrifolia* plants grown in Examples 55 to 64 days after planting.

| Example | Fertilizers | Height (cm) | Leaf length (cm) | Leaf width (cm) | Weight of 6 plants (gram) | Total yield (gram) |
|---|---|---|---|---|---|---|
| 55 (comparative) | DAP | 7.60 | 4.20 | 2.40 | 9 | 15 |
| 56 | DAP0503 from Example 13 | 25.1 | 11.8 | 7.80 | 161 | 213 |
| 57 | DAPTA0503 from Example 33 | 24.9 | 12.2 | 8.00 | 159 | 302 |
| 58 | DAPTABS0503 from Example 35 | 24.3 | 11.6 | 7.20 | 121 | 271 |
| 59 | DAPTANAA0503 from Example 36 | 25.8 | 12.6 | 8.00 | 173 | 380 |
| 60 | DAPTAGA0503 from Example 37 | 25.9 | 12.4 | 7.80 | 146 | 343 |
| 61 | DAPTABA0503 from Example 38 | 24.3 | 11.2 | 7.10 | 119 | 289 |
| 62 | DAPTAAA0503 from Example 34 | 23.5 | 11.5 | 6.90 | 112 | 256 |
| 63 | DAPTAAA0503GA from Example 39 | 19.2 | 10.5 | 6.50 | 114 | 240 |
| 64 | DAPTAAA0503NAA from Example 40 | 21.6 | 11.9 | 7.30 | 109 | 200 |

The fertilizers of the invention produced significantly larger plants in a much higher yield than the plain DAP fertilizer.

Examples 65 to 73—Rice Farming

Smart N-Fertilizers of this invention were used for rice farming in Longduc Commue, Travinh City, Vietnam between August and October 2017. For each example, an experiment was done on a 1,000 m² rice paddy field using DaiThom 8 certified rice seed, which is a 100-day rice variety available from Southern Seed Joint Stock Company, Ho Chi Minh City, Vietnam. The 14-day old rice plants were transplanted to the tilled soil using a Yanmar Rice Transplanter (Model YR60D), which was equipped with an automatic fertilizer applicating system. The fertilizers were buried at a depth around 5 cm in the soil and 5 cm away from to the rice plants. The space between the rice plants was 30 cm by 15 cm. All the rice paddy fields were flooded with water up to about 2-5 cm above the soil surface from day 5 to day 25. During the period between day 26 and 36, water was gradually drained down to −15 cm below the soil surface. On day 37, water was slowly pumped into the rice paddy field up to 5 cm above the soil surface. During the period between day 38 and 49, water was gradually drained down to −15 cm below the soil surface. On day 50, water was slowly pumped into the rice paddy filed to around 5 cm above the soil surface and kept at this level until day 85. Water was then let to evaporate naturally to dryness in view of harvesting on day 102.

|  | EXAMPLES | | | | | | | | |
|Description|65 (comp.)|66 (comp.)|67 (comp.)|68|69|70|71|72|73|
|---|---|---|---|---|---|---|---|---|---|
|Urea|22 Kg|—|—|—|—|—|—|—|—|
|Urea N-Humus|—|22 Kg|—|—|—|—|—|—|—|
|Urea N-46-Plus|—|—|22 Kg|—|—|—|—|—|—|
|N0503 from Example 10|—|—|—|5 Kg|—|—|—|—|—|
|N0703 from Example 11|—|—|—|6 Kg|—|—|—|—|—|
|NH0703 from Example 15|—|—|—|—|5 Kg|5 Kg|—|—|—|
|NH1003 from Example 16|—|—|—|—|6 Kg|—|—|—|—|
|NH0703NAA from Example 18|—|—|—|—|—|6 Kg|—|—|—|
|NC0503 from Example 19|—|—|—|—|—|—|5 Kg|—|—|
|NC0703 from Example 20|—|—|—|—|—|—|6 Kg|—|—|
|NBD0503 from Example 21|—|—|—|—|—|—|—|5 Kg|—|
|NBD0703 from Example 22|—|—|—|—|—|—|—|6 Kg|—|
|NBD0503NAA from Example 23|—|—|—|—|—|—|—|—|6 Kg|
|NBD0703NAA from Example 24|—|—|—|—|—|—|—|—|5 Kg|
|DAP (Kg)|8|8|8|8|8|8|8|8|8|
|Potash (Kg)|11|11|11|11|11|11|11|11|11|
|Yields (Kg) per 1,000 m²|483|540|543|620|702|718|663|660|694|
|Rice (Kg)/Fertilizer (Kg)|11.8|13.2|13.2|20.7|23.4|23.9|22.1|22.0|23.1|

The fertilizers of the invention produced rice in a much higher yield compared to the three comparative fertilizers used, despite the fact that much less fertilizer was used. The rice/fertilizer weight ratio was almost double for the fertilizers of the invention.

Examples 101-114—Other Copolymeric Nanoparticles

We show below the synthesis, characterization, and use of other copolymeric nanoparticles and compare their performances to those of nanoparticles of POLY-001, POLY-005, and POLY-007. The result reported below concerned potash fertilizers, rather than the nitrogen fertilizers of the invention. Nevertheless, these results show that these other copolymeric nanoparticles can be successfully used in the nitrogen fertilizers of the invention because the copolymeric nanoparticles in the potash fertilizers are used in the same manner for the same purpose as in the nitrogen fertilizers of the invention.

Example 101—Water-Swellable Copolymeric Nanoparticles POLY-002

The synthesis of copolymeric nanoparticles POLY-002 (as an aqueous suspension) was done similarly to the synthesis of POLY-001 with the exception that 0.82 Kg of vinylphosphonic acid was used instead of acrylic acid.

Copolymer POLY-002 was:

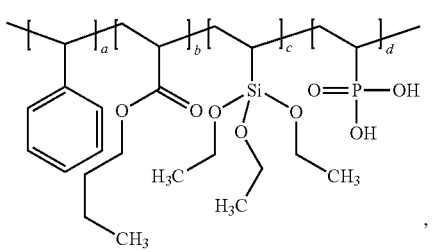

with a, b, c and d being 48 wt %, 48 wt %, 3 wt % and 1 wt %, respectively.

The glass transition temperature, particle size, and polydispersity of POLY-001 were measured to be 20° C., 91.3 nm and 0.005, respectively.

Figure 18:
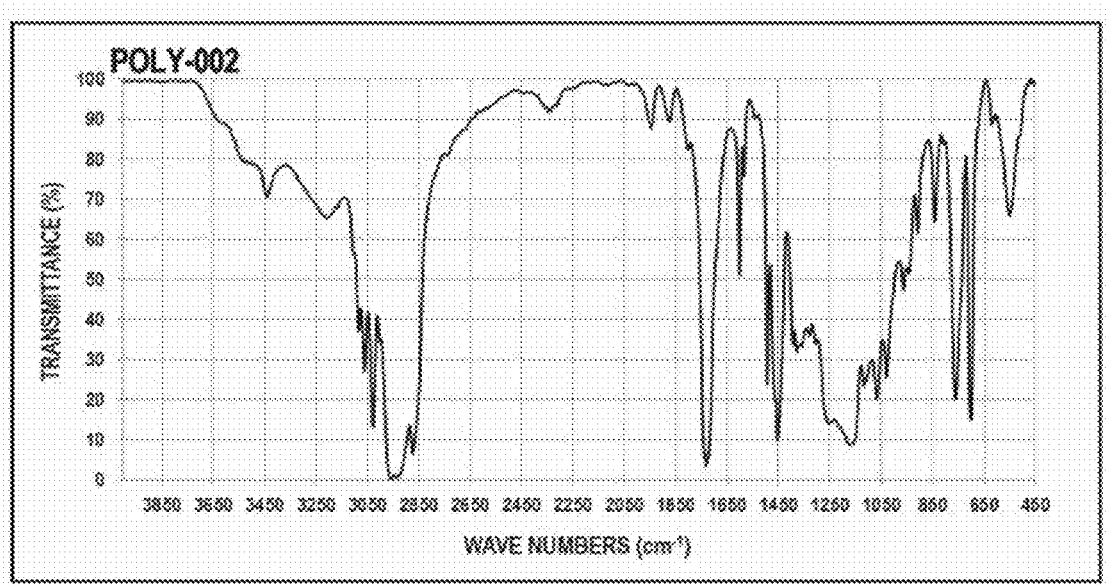
FIG. 18 shows the FTIR spectrum of copolymeric nanoparticles POLY-002 in a KBr pellet.

FIG. 18 shows the FTIR spectrum of copolymeric nanoparticles POLY-002 in a KBr pellet.

Example 102—Water-Swellable Copolymeric Nanoparticles POLY-003

The synthesis of copolymeric nanoparticles POLY-003 (as an aqueous suspension) was done similarly to the synthesis of POLY-001 with the exception that 0.82 Kg of acrylamide was used instead of acrylic acid.

Copolymer POLY-003 was:

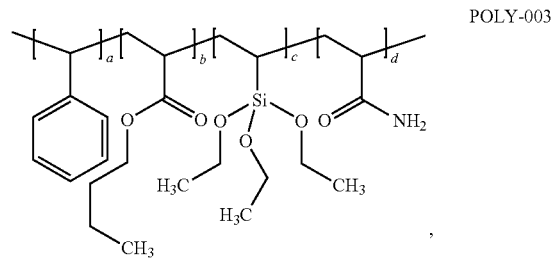

with a, b, c and d being 48 wt %, 48 wt %, 3 wt % and 1 wt %, respectively.

The glass transition temperature, molecular weight, particle size, and polydispersity of POLY-001 were measured to be 21° C., 112 kDa, 67.0 nm, and 0.003, respectively.

Figure 19:
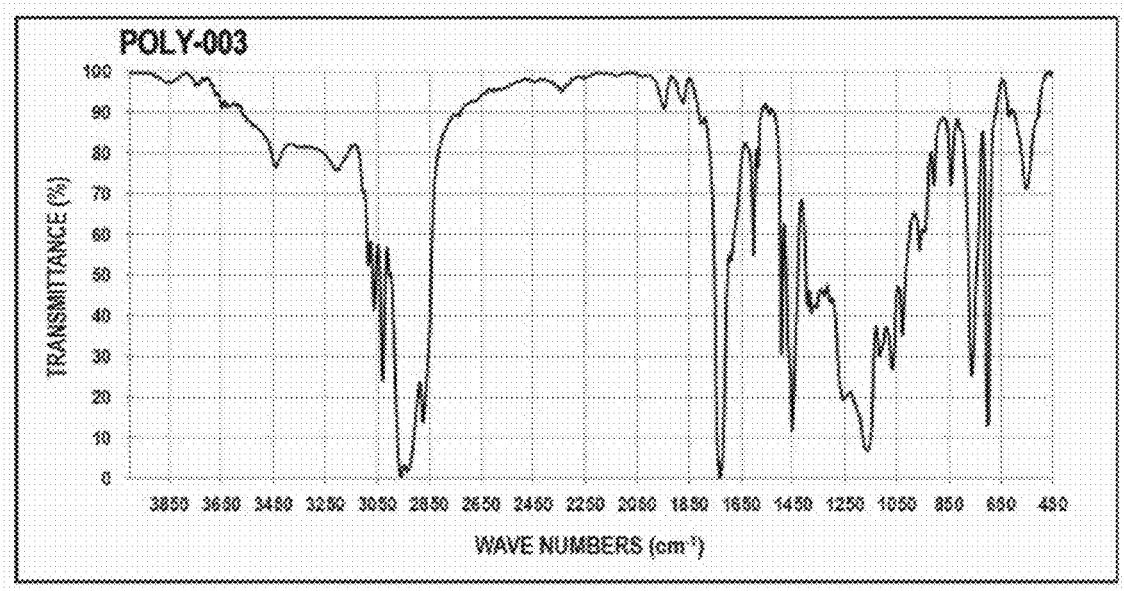
FIG. 19 shows the FTIR spectrum of copolymeric nanoparticles POLY-003 in a KBr pellet.

FIG. 19 shows the FTIR spectrum of copolymeric nanoparticles POLY-003 in a KBr pellet.

Example 103—Water-Insoluble Copolymeric Nanoparticles POLY-005

The synthesis of copolymeric nanoparticles POLY-005 (as an aqueous suspension) was done by mixing a prepolymer solution, which comprised 236 Kg of deionized water, 47.0

Kg of styrene, 50.0 Kg of butyl methacrylate, 3.00 Kg of N,N-dimethylamino ethylmethacrylate, 0.82 Kg of ammonium bicarbonate and 0.82 Kg n-octanol in a 1,000-liter stainless steel tank with a high shear mixer. In a separate smaller tank, a solution of ammonium persulfate free radical initiator was prepared by dissolving 0.42 Kg of ammonium persulfate into 10 Kg deionized water.

One hundred and sixty kilograms of the prepolymer solution were loaded in the reactor. The temperature was slowly raised to 80° C. and the remaining prepolymer solution was added to the reactor using a dosing pump at a rate 32.0 Kg per hour. Simultaneously, the ammonium persulfate solution was also added to the reactor using a dosing pump at a rate of 2.00 Kg per hour.

After both solutions were completely added to the reactor, the polymerization was continued at 80° C. under nitrogen atmosphere and constant stirring for additional 15 hours. Reaction samples were removed from the reactor after 16, 20 and 24 hours to measure the solid weight for monitoring the completeness of the polymerization.

The particle size of the copolymeric nanoparticles was measured to be 1,250 nm with a polydispersity of 0.120.

Then, 6.60 Kg of gibberellic acid were slowly added to the reactor and the stirring continued in the same conditions for an additional 3 hours.

Copolymer POLY-005 was:

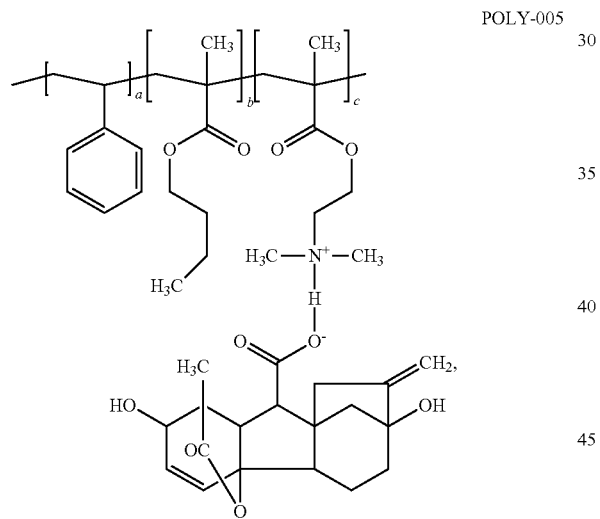

POLY-005 with a being 44 wt %, b being 47 wt % and c being 9 wt %.

The particle size and polydispersity were measured to be 109 nm and 0.078, respectively.

Deionized water was added to the reactor to adjust the solid weight to 25%, thus producing a suspension that could directly be used (with optional further dilution as desired) to produce smart release potash fertilizers.

Figure 20:
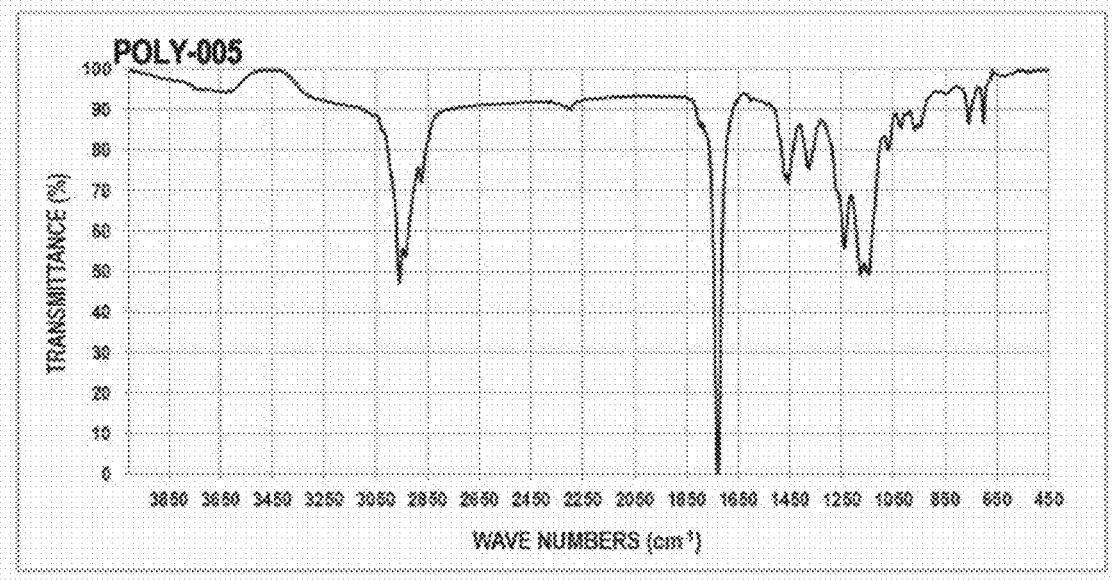
FIG. 20 shows the FTIR spectrum of copolymeric nanoparticles POLY-005 in in a KBr pellet.

FIG. 20 shows the FTIR spectrum of copolymeric nanoparticles POLY-005 in a KBr pellet.

Example 104—Water-Insoluble Copolymeric Nanoparticles POLY-007

The synthesis of copolymeric nanoparticles POLY-007 (as an aqueous suspension) was performed in the same manner as in Example 103 with the exception that the monomers were 47.0 Kg of styrene, 50.0 Kg of butyl methacrylate and 3.00 Kg of 2-(dimethylamino)ethyl methacrylate. After 24 hours of polymerization, 3.55 Kg of 1-naphthalene acetic acid were slowly added to the reactor. The reaction was continued, stirring, in the same conditions, for an additional 3 hours. Then, the reactor was cooled to room temperature and deionized water was added to dilute to 25% solid weight, thus producing a suspension that could directly be used (with optional further dilution as desired) to produce smart release potash fertilizers.

Copolymer POLY-007 was:

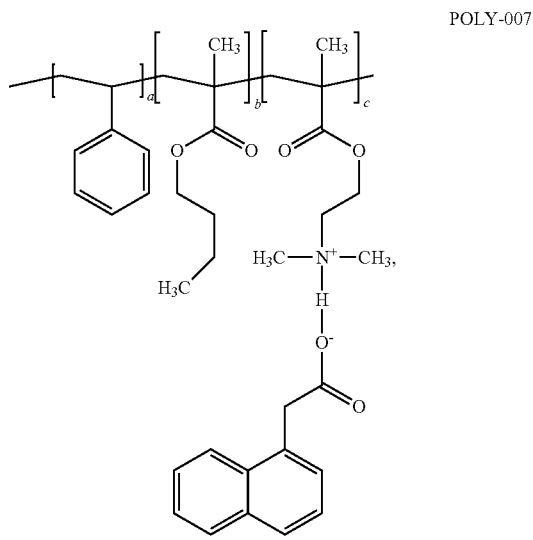

POLY-007 with a being 46 wt %, b being 48 wt % and c being 6 wt %.

The particle size and polydispersity of POLY-007 were measured to be 76 nm and 0.03, respectively.

Figure 21:
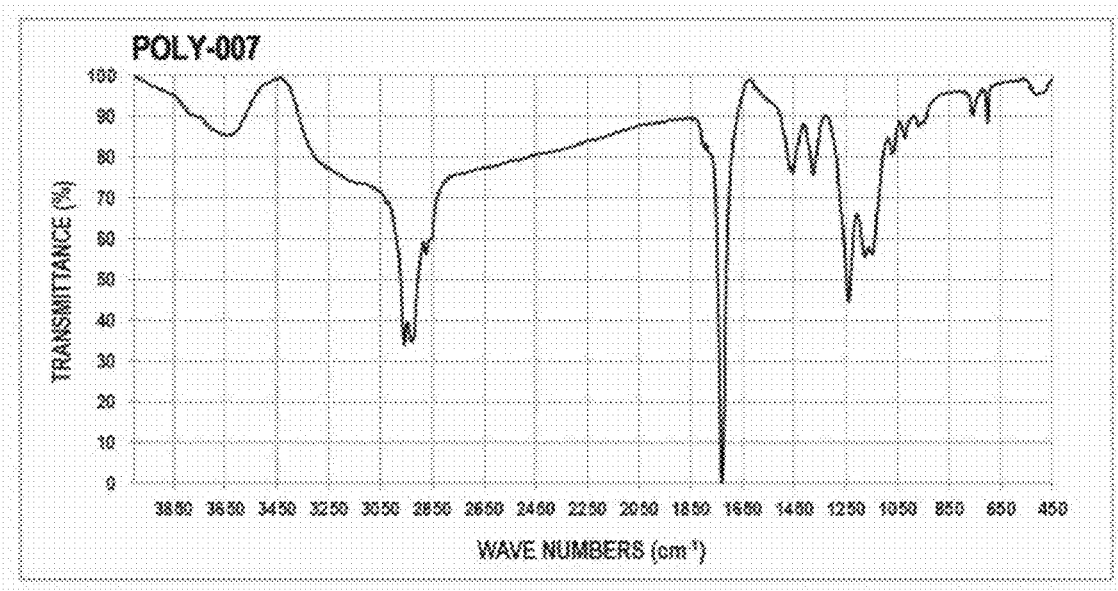
FIG. 21 shows the FTIR spectrum of copolymeric nanoparticles POLY-007 in in a KBr pellet.

FIG. 21 shows the FTIR spectrum of POLY-007 in a KBr pellet.

Example 105—Water-Insoluble Copolymeric Nanoparticles POLY-009

The synthesis of copolymeric nanoparticles POLY-009 was performed in the same manner as in Example 103 with the exception that the monomers were 47.0 Kg of styrene, 50.0 Kg of butyl methacrylate and 3.00 Kg of 2-(dimethylamino)ethyl methacrylate. After 24 hours of polymerization, 3.20 Kg of 4-nitrobenzoic acid were slowly added into the reactor. The reaction was continued, stirring, in the same conditions, for an additional 3 hours. Then, the reactor was cooled to room temperature and deionized water was added to dilute to 25% solid weight, thus producing a suspension that could directly be used (with optional further dilution as desired) to produce smart release potash fertilizers.

Copolymer POLY-009 was:

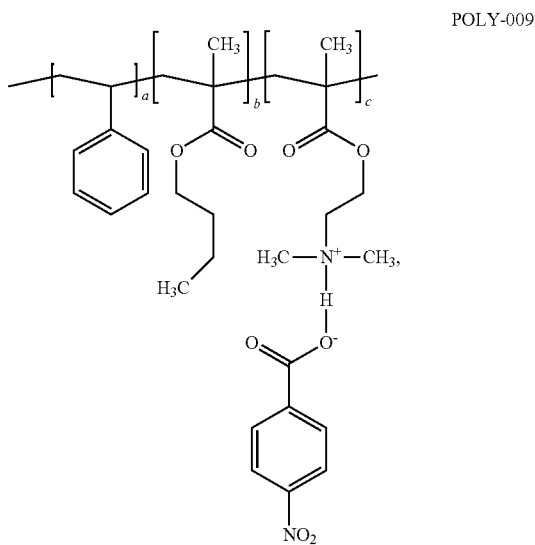

POLY-009

Copolymer POLY-011 was:

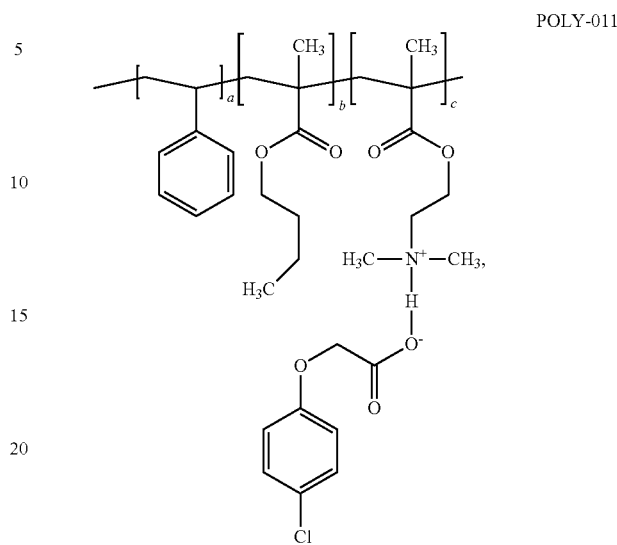

POLY-011 with a being 46 wt %, b being 48 wt % and c being 6 wt %.

The particle size and polydispersity were measured to be 91 nm and 0.035, respectively.

Figure 23:
FIG. 23 shows the FTIR spectrum of copolymeric nanoparticles POLY-011 in a KBr pellet.

FIG. 23 shows the FTIR spectrum of POLY-011 in a KBr pellet.

Production of Smart Release Potash Fertilizers

The smart release potash fertilizer granule comprised:
a potash core;
an extended release layer covering the potash core, wherein the extended release layer comprises water-swellable copolymeric nanoparticles and at least one water-soluble organic acid or water-soluble organic carboxylate salt;
a controlled release layer covering the extended release layer, wherein the controlled release layer comprises water-swellable copolymeric nanoparticles; and
an anticaking layer covering the controlled release layer, wherein the anticaking layer comprises water-insoluble copolymeric nanoparticles.

Irregularly shaped potash granules (potassium chloride 00:00:61, available from Phu My Fertilizers, Vietnam) were sieved to remove granules less than 2.0 mm in size. Then, the sieved potash granules (10 Kg) were loaded into a home-built Wurster fluidized bed. The bed temperature was set at 32±2° C. with 20% relative humidity using a hot air stream at a speed of 300 to 400 m³ per hour. The potash granules were agitated using this hot air stream. First, the granules were agitated for 5 minutes to dry them.

Coating the Granules with an Extended Release Layer

An aqueous solution containing 5% solid weight of water-swellable copolymeric nanoparticles together with an organic acid was sprayed from the bottom of the fluidized bed at the rate of 60 grams per minute. The mists were carried by the hot air stream and deposited the copolymeric nanoparticles and organic acid onto the surface of the potash granules (which were floating in the hot air stream of the fluidized bed). This process was continued until the desired coating thickness was reached.

Then, the spraying was stopped, and the granules were agitated by the hot air stream of the fluidized bed in the same conditions for an additional 10 minutes to dry the granules before the next layer (controlled release layer) was applied.

with a being 46 wt %, b being 48 wt % and c being 6 wt %.

The particle size and polydispersity of POLY-009 were measured to be 109 nm and 0.021, respectively.

Figure 22:
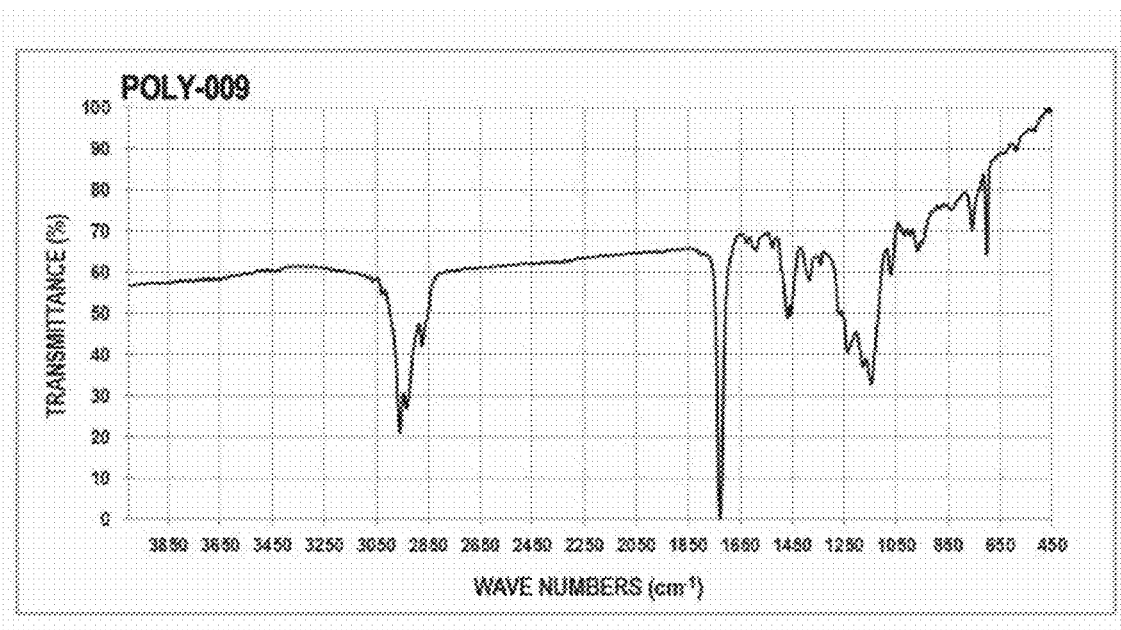
FIG. 22 shows the FTIR spectrum of copolymeric nanoparticles POLY-009 in a KBr pellet.

FIG. 22 shows the FTIR spectrum of POLY-009 in a KBr pellet.

Example 106—Water-Insoluble Copolymeric Nanoparticles POLY-011

The synthesis of POLY-011 (as an aqueous suspension) was performed in the same manner as in Example 103 with the exception that the monomers were 47.0 Kg of styrene, 50.0 Kg of butyl methacrylate and 3.00 Kg of 2-(dimethylamino)ethyl methacrylate. After 24 hours of polymerization, 3.56 Kg of 4-chlorophenyloxy acetic acid were slowly added to the reactor. The reaction was continued, stirring, in the same conditions for an additional 3 hours. Then, the reactor was cooled to room temperature and deionized water was added to dilute to 25% solid weight, thus producing a suspension that could directly be used (with optional further dilution as desired) to produce smart release potash fertilizers.

Coating the Granule with a Controlled Release Layer

The coating of the controlled release layer on top of the extended release layer was done in the same manner with the exception that an aqueous solution contained only copolymeric nanoparticles (25% solid weight) was sprayed. This process was continued until the desired coating thickness was reached.

Then, the spraying was stopped and the granules were agitated by the hot air stream of the fluidized bed in the same conditions for an additional 10 minutes to dry the granules before the next layer (anticaking layer) was applied.

Coating the Anticaking Layer

The coating of the anticaking layer on top of the controlled release layer was done in the same manner with the exception that water-insoluble copolymeric nanoparticles were used and the temperature of the fluid bed was raised to 45° C.

After the desired thickness was reached, the spraying was stopped, and the granules were agitated by the hot air stream of the fluidized bed in the same conditions for an additional 20 minutes to completely remove the water.

For comparison purpose, the total weight of the copolymers in the extended release layer and controlled release layer was kept at 10 wt % based on the weight of the potash core.

Characterization of the Smart Release Potash Fertilizers

Determination the Cumulative Potassium Release

To measure the potassium release in water, 4 g of coated smart release potash fertilizer granules were immersed in 400 mL water in a glass bottle. The glass bottle was placed in an oven at 30° C. At specific times, 5 mL of solution were collected for the determination of potassium concentration. The sample solution was pumped into an atomic absorption spectrometer (Perkin Elmer® AAnalyst 200) to record the potassium atomic absorption.

A set of five standard KCl solutions with known concentrations were prepared and their potassium atomic absorption were measured. A calibration curve of the potassium atomic absorption vs the potassium concentration was plotted. To determine an unknown potassium concentration in an aqueous sample, the potassium absorption of the sample was compared with the calibration curve, which allowed to determine its potassium concentration. If the potassium absorption was not in the working range of the calibration curve, the sample solution was diluted in HCl 1% before AAS analysis.

The cumulative potassium release (%) was calculated using the following equation:

% Cumulative release of potassium=$M_{release}$/$M_{total\ release}$×100 wherein $M_{release}$ is the weight of potassium released in the aqueous solution at a specific time and $M_{total\ release}$ is the maximum weight of potassium released in the aqueous solution by the fertilizer. To obtain the $M_{total\ release}$ value, the coated fertilizer granules were ground to a fine powder, which was dissolved in water, and the potassium concentration of the resulting solution was determined as described above.

Determination of the Organic Acid Cumulative Release 24 g coated fertilizer granules were immersed in 200 mL water in a glass bottle that was stored in an oven at 30° C. After specific periods of time, a 5 mL sample solution was collected for UV-vis spectroscopy analysis using a Jasco® V-670 absorption spectrometer. The absorption intensity at a particular wavelength was compared with a calibration curve to calculated the organic acid concentration released. The percentage of organic acid release was calculated using the following equation:

% Cumulative Release of Organic Acid=$M_{release}$/$M_{total\ release}$×100 wherein $M_{release}$ is the weight of analyte released in the aqueous solution at a specific time and $M_{total\ release}$ is the maximum weight of analyte released in the aqueous solution. To determine $M_{total\ release}$, the fertilizer granules were ground into a fine powder and then dissolved in water, which allowed obtaining the maximum amount of water-soluble analytes ($m_{absolute-release}$) using the UV-vis absorption spectroscopy method described above.

Gibberellic Acid (GA3) Concentration Measurements A solution of 4,000 ppm GA3 was prepared by dissolving 0.04 g of GA3 in 100 mL ethanol. For UV-Vis absorption analysis, the GA3 solution 4000 ppm was diluted with ethanol and a HCl solution 3.75M in a 25 mL volume flask to obtain standard GA3 solutions with specific concentrations (see the following table). Composition of standard GA3 solutions for UV-vis spectroscopy calibration

| Standard GA3 concentration (ppm) | 200 | 400 | 600 | 800 | 1000 |
|---|---|---|---|---|---|
| Volume of GA3 solution 4,000 ppm (mL) | 1.25 | 2.5 | 3.75 | 5 | 6.25 |
| Volume of ethanol (mL) | 1 | 1 | 1 | 1 | 1 |
| Volume of HCl solution 3.75M (mL) | 22.75 | 21.5 | 20.25 | 19 | 17.75 |

Indole-3-acetic Acid, 4-Chlorophenoxyacetic Acid and 1-Naphthalene Acetic Acid Concentration Measurements Calibration curves of these organic acids were prepared by analyzing the UV-vis absorption spectra of solutions of known concentrations of the organic acids in ethanol. To determine the organic acid concentration in an aqueous sample, a 5 mL aqueous solution sample was diluted in ethanol two-fold for UV-vis spectroscopy. The absorption intensities at particular wavelengths were used to calculate the organic acid concentrations using the calibration curves.

For sample analysis, a 5 mL aqueous solution was mixed with 1 mL ethanol and 19 mL of a HCl solution 3.75M in a 25 mL volume flask. The resulting solution was analyzed with UV-vis spectroscopy. The absorption intensity at 254 nm was compared with the calibration curve to determine the organic acid concentration.

Salicylic Acid (SA) Concentration Measurements 0.1 g of SA was dissolved in 5 mL NaOH solution 1M, which was then diluted in water to obtain 100 mL SA solution 1000 ppm. The SA solution 1000 ppm was mixed with a $FeCl_3$ solution 0.02M in a 25 mL volume flask to produce standard SA solutions for the calibration curve (see the following table). Composition of standard SA solutions for UV-vis spectroscopy calibration are shown in the table below.

| Standard SA concentration (ppm) | 0 | 20 | 40 | 60 | 80 |
|---|---|---|---|---|---|
| Volume of SA solution 1000 ppm (mL) | 0 | 0.5 | 1 | 1.5 | 2 |
| Volume of $FeCl_3$ solution 0.02M (mL) | 25 | 24.5 | 24 | 23.5 | 23 |

In the concentration measurement, a 5 mL sample solution was diluted in 20 Ml of a $FeCl_3$ solution 0.02M to obtain a violet solution. The absorption intensity at 529 nm was compared to the calibration curve to determine the SA concentration in the sample solution.

Examples 107-109—Cumulative Potassium Release from Fertilizers with Various Copolymeric Nanoparticles Smart release potash fertilizers were produced by coating potash granules:

- with an aqueous suspension comprising 2.5% solid weight of gluconic acid and 2.5% solid weight of different copolymeric nanoparticles POLY-001 (Example 107), POLY-002 (Example 108), or POLY-003 (Example 109) to form an extended release layer with a coating weight of 2 wt %, based on the weight of the potash core,
- then, with an aqueous suspension comprising copolymeric nanoparticles POLY-001 to form a controlled release layer with a coating weight of 8 wt %, based on the weight of the potash core, and
- finally, with an aqueous suspension comprising copolymeric nanoparticles POLY-007 to form an anti-caking layer with a coating weight of 3 wt %, based on the weight of the potash core.

The following table reports the cumulative potassium release from these smart release potash fertilizers after 10, 20 and 40 days. The smart release potash fertilizer with copolymeric nanoparticle POLY-002 provided the slowest cumulative potassium release of in water compared to POLY-001 and POLY-003.

Cumulative Potassium Release after 10, 20 and 40 Days

|          |           | Cumulative Release of Potassium (%) | | |
|----------|-----------|---------|---------|---------|
| Examples | Copolymers | 10 Days | 20 Days | 40 Days |
| 107 | POLY-001 | 9.40 | 15.0 | 22.4 |
| 108 | POLY-002 | 9.20 | 12.5 | 17.4 |
| 109 | POLY-003 | 10.0 | 13.8 | 24.8 |

Examples 110-114—Acid Release from Fertilizers with Various Copolymeric Nanoparticles Smart release potash fertilizers were produced by coating potash granules:

- with an aqueous suspension comprising 2.5% solid weight of gluconic acid and 2.5% solid weight of POLY-001 to form an extended release layer with a coating weight of 2 wt %, based on the weight of the potash core,
- then, with an aqueous suspension comprising copolymeric nanoparticles POLY-001 to form a controlled release layer with a coating weight of 8 wt %, based on the weight of the potash core, and
- finally, with an aqueous suspension comprising copolymeric nanoparticles comprising POLY-005 (Example 110), POLY-007 (Example 111), POLY-009 (Example 112), POLY-010 (Example 113), or POLY-011 (Example 114) to form an anti-caking layer with a coating weight of 3 wt %, based on the weight of the potash core.

The following table reports the number of days required for the cumulative anion (acid) release to reach 100%. The cumulative the release was strongly dependent on the pKa of the associated acids. The stronger the acids, the longer slower the anion release.

Number of Days Required to Reach 100% Cumulative Anion Release

| Example | Copolymers | Anion Pendant Group | pKa* | Days required |
|---------|-----------|---------------------|------|---------------|
| 110 | POLY-005 | Gibberelloate | 4.00 | 10 days |
| 111 | POLY-007 | 1-Naphthalene acetoate | 4.23 | 12 days |
| 112 | POLY-009 | 4-Nitrobenzoate | 3.44 | 20 days |
| 113 | POLY-010 | Salicyloate | 2.60 | 36 days |
| 114 | POLY-011 | 4-Chlorophenyloxy acetoate | 3.58 | 15 days |

*of associated acids

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

L. Dong, A. L. Córdova-Kreylosb, J. Yanga, H. Yuana, and K. M. Scow, Humic acids buffer the effects of urea on soil ammonia oxidizers and potential nitrification, Soil Biol Biochem. 2009 August; 41(8): 1612-1621;

U.S. Pat. No. 4,019,890;
U.S. Pat. No. 4,657,576;
U.S. Pat. No. 4,851,027;
U.S. Pat. No. 4,880,455;
U.S. Pat. No. 6,187,074;
Chinese patent CN104355874; and
Chinese patent CN101875584.

The invention claimed is:

1. A nitrogen-containing fertilizer granule comprising:
    a nitrogen-containing fertilizer core;
    an organic functional layer covering the core, wherein the organic functional layer comprises at least one functional organic compound that is an enzyme inhibitor, a microbial suppressor, a phosphorus solubilizer, and/or a plant hormone;
    a controlled release layer covering the organic functional layer, wherein the controlled release layer comprises water-swellable copolymeric nanoparticles; and
    an anticaking layer covering the controlled release layer, wherein the anticaking layer comprises water-insoluble copolymeric nanoparticles, wherein the copolymer making the water-insoluble copolymeric nanoparticles comprises repeat units having a plant hormone or a phosphorus solubilizer covalently or ionically attached as a pendant group.

2. The fertilizer granule of claim 1, wherein the enzyme inhibitor is an urease inhibitor, which is
    chitosan,
    humic acids, for example provided in the form of humus,
    fulvic acids,
    a polyphenol, unsubstituted or substituted,
    saponin,
    N-(n-butyl)thiophosphoric triamide,
    phenylphosphorodiamidate,
    acetohydroxamic acid,
    alkyl hydroxamic acid,
    trans-cinnamoyl hydroxamic acid, benzohydroxamic acid, or hydroxamic acid, or a combination thereof.

3. The fertilizer granule of claim 2, wherein the polyphenol is substituted tannic acid bearing one or more substituents, wherein said substituents comprise a functional group bearing negative or positive charge and an oppositely charged counterion, and wherein the oppositely charged counterion is a metal cation or a carboxylate or sulfonate anion of an organic acid that is a microbial suppressor, a phosphorus solubilizer, and/or a plant hormone.

4. The fertilizer granule of claim 3, wherein said substituent is:

acetic acid potassium salt, butyl sulfonic acid potassium salt, ethyl ammonium gibberellic acid salt, ethyl ammonium 1-napthanlene acetic acid salt, or ethyl ammonium 4-nitrobenzoic acid salt.

5. The fertilizer granule of claim 4, wherein the substituted tannic acid has the following ideal chemical structure:

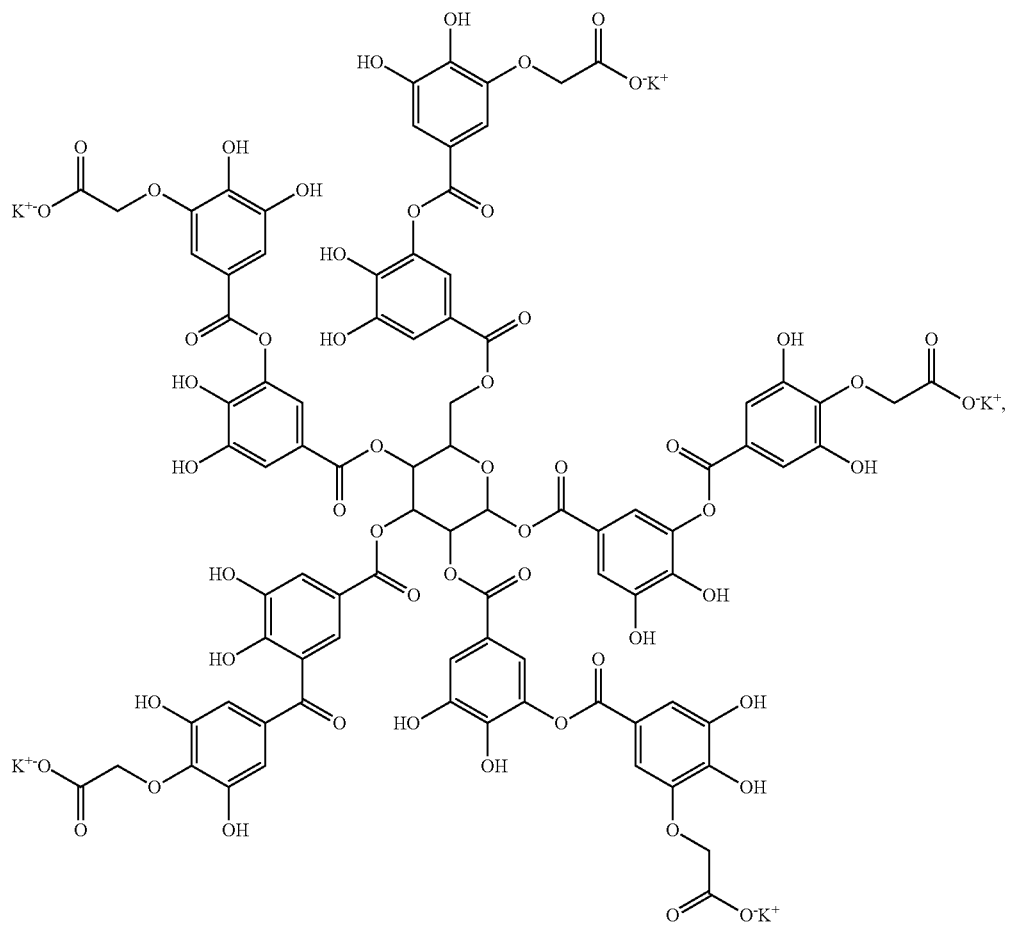

Tannic acid substituted with acetic acid potassium salt (TAAA)

-continued
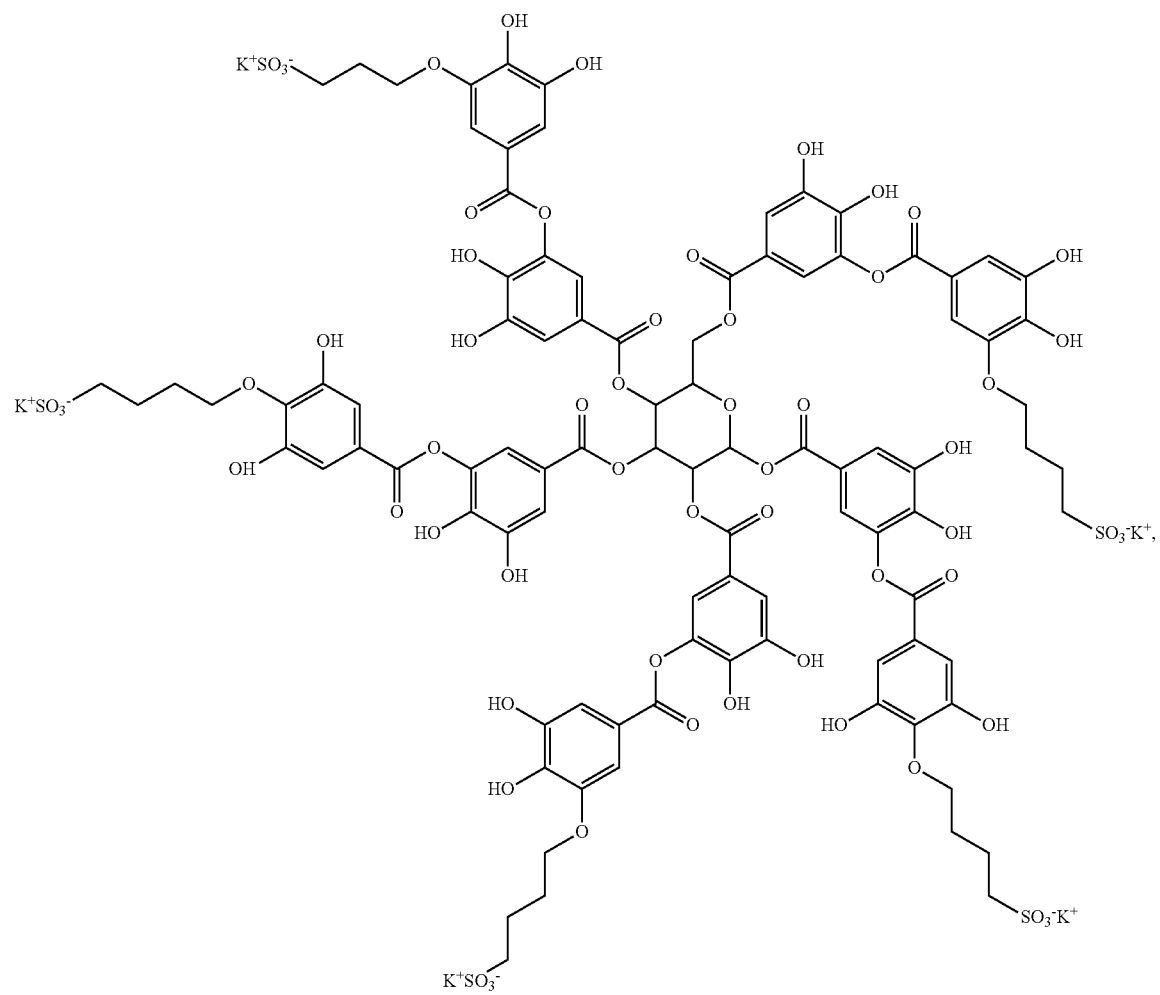
Tannic acid substituted with butyl sulfonic acid potassium salt (TABS)

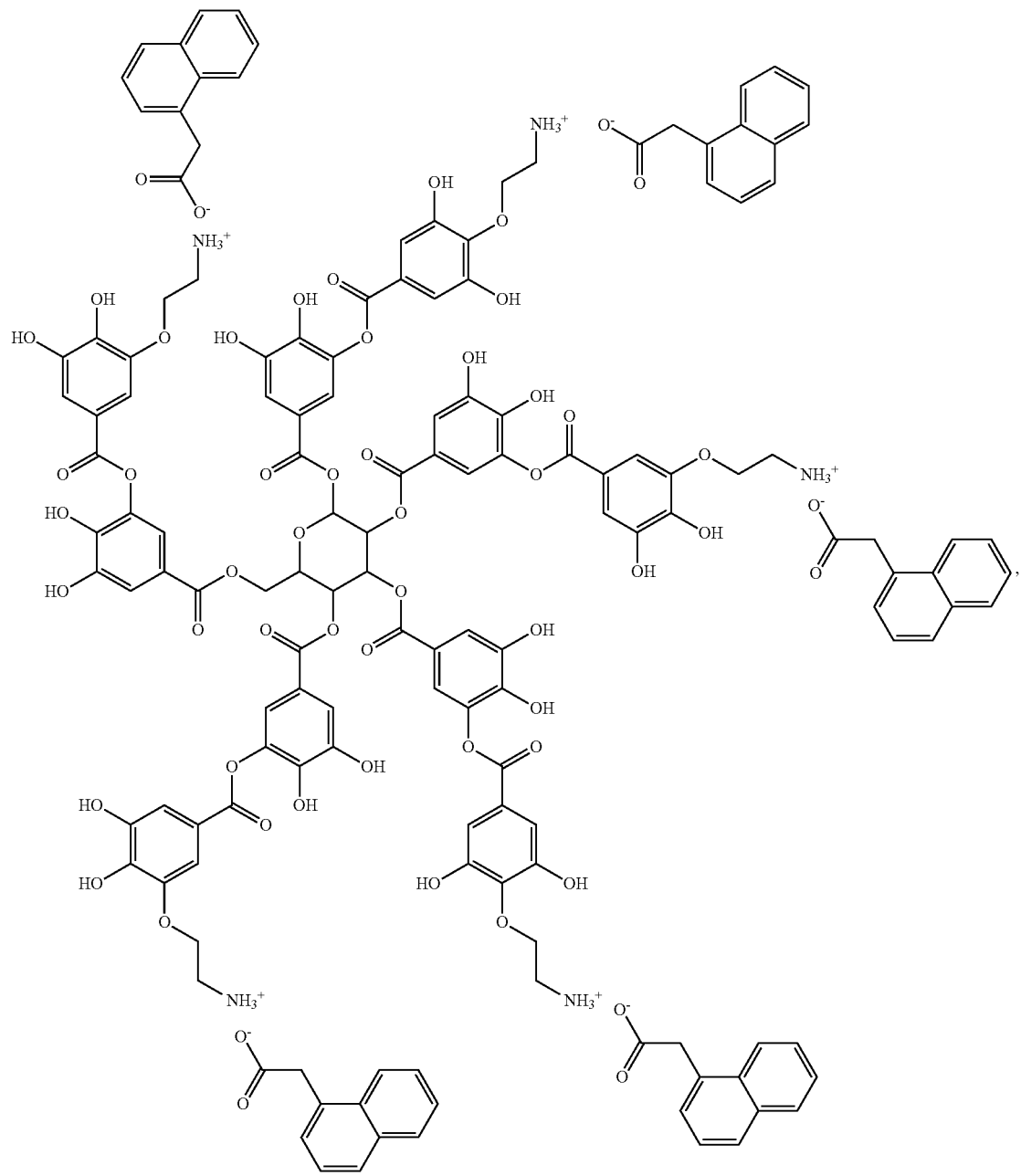
Tannic acid substituted with ethyl ammonium 1-napthanlene acetic acid salt (TANAA)

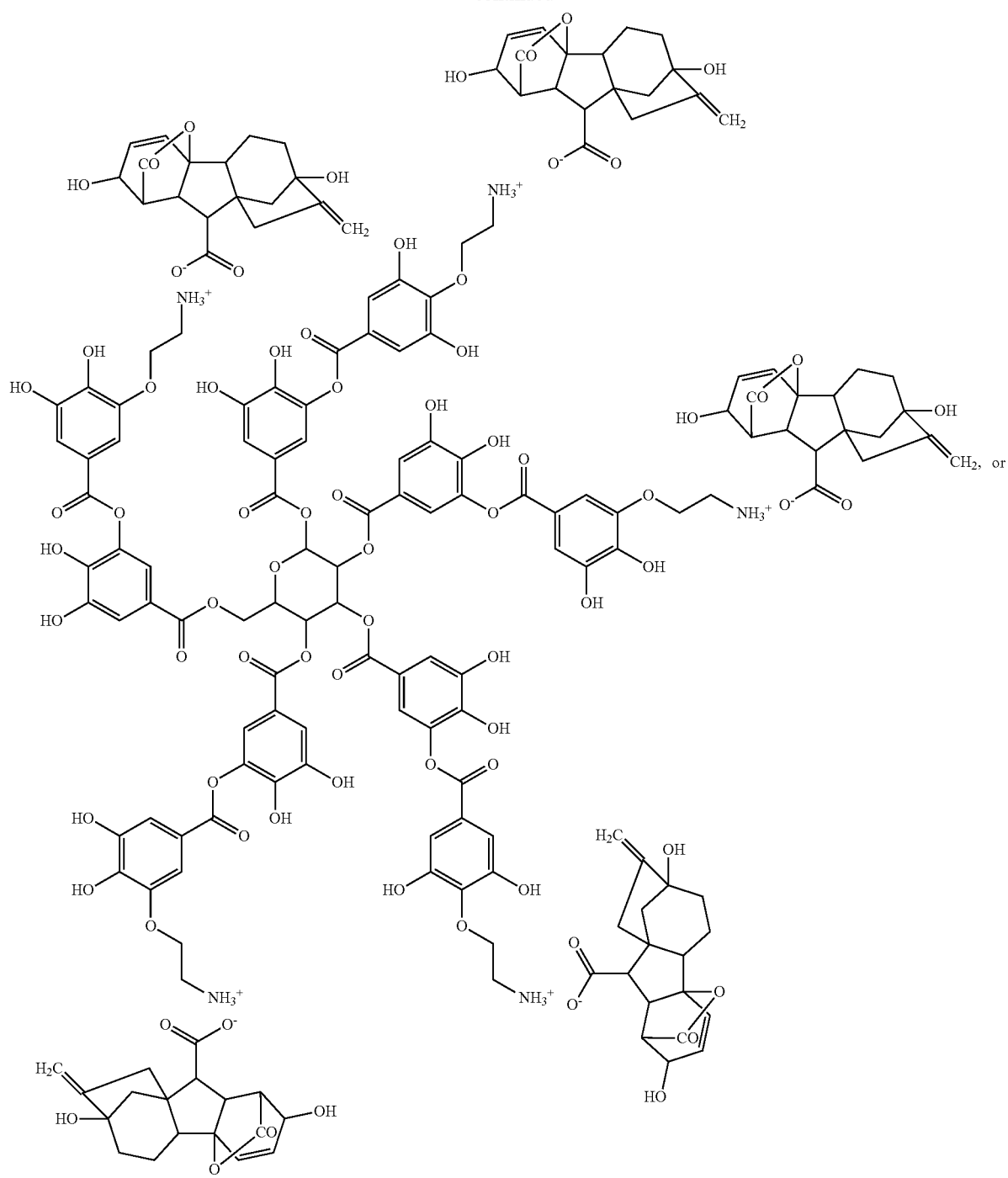
Tannic acid substituted with ethyl ammonium gibberellic acid salt (TAGA)

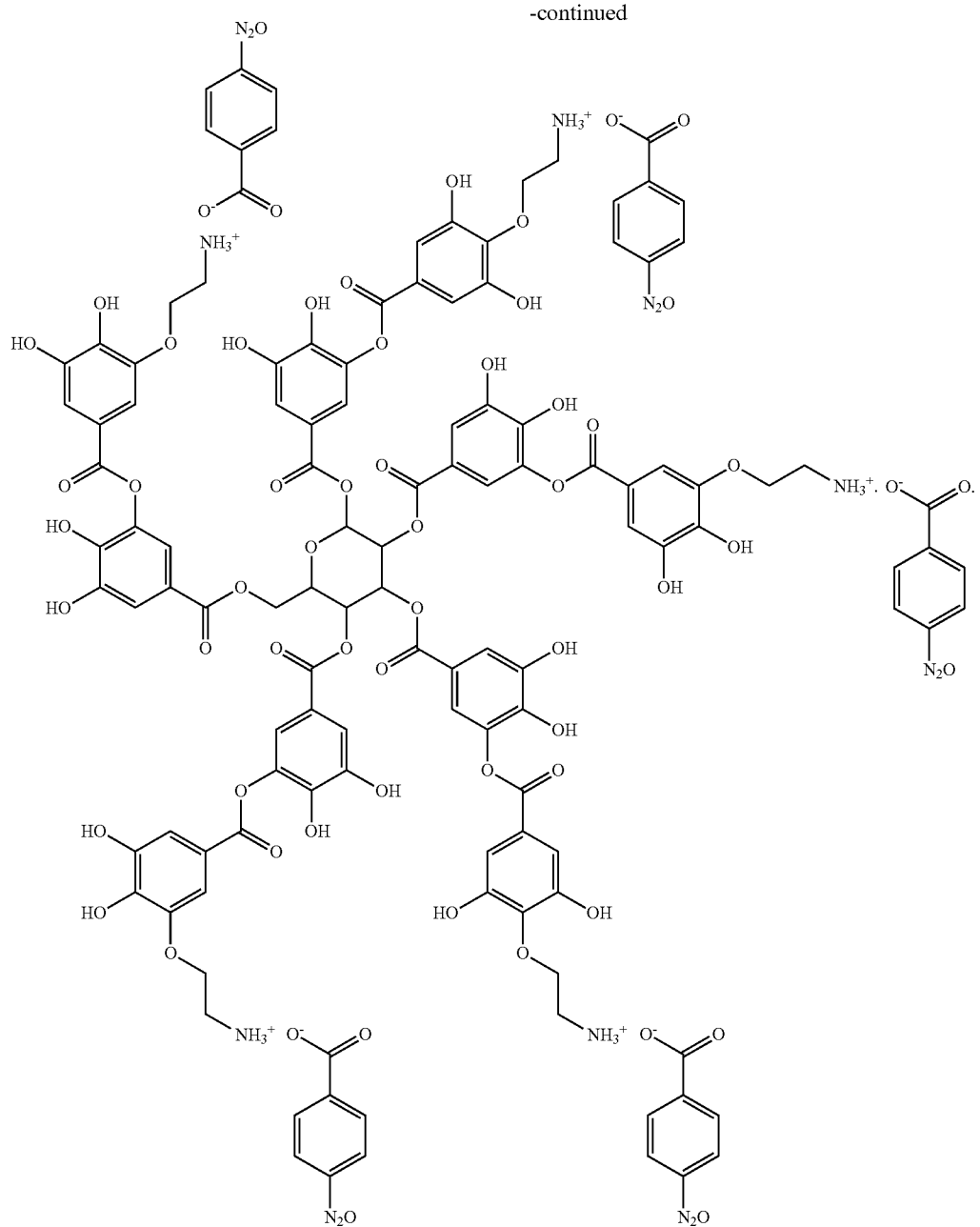

Tannic acid substituted with ethyl ammonium 4-nitrobenzoic acid salt (TABA)

6. The fertilizer granule of claim 3, wherein the polyphenol is substituted tannic acid bearing two or more substituents.

7. The fertilizer granule of claim 3, wherein the polyphenol is substituted tannic acid bearing five substituents.

8. The fertilizer granule of claim 1, wherein the copolymer making the water-insoluble copolymeric nanoparticles is of formula (II):

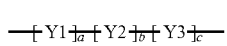
(II)

wherein:
- Y1 represents styrene repeat units;
- Y2 represents alkyl acrylate or alkyl methacrylate repeat units;
- Y3 represents repeat units comprising, as a pendant group, an ionically or covalently attached said plant hormone or said phosphorus solubilizer;
- a and b represents the weight percent of repeat units Y1 and Y2, respectively, based on the total weight of the copolymer, and vary between about 10 wt % to about 95 wt %; and
- c represents the weight percent of repeat units Y3, based on the total weight of the copolymer, and vary between 0 wt % to about 30 wt %.

9. The fertilizer granule of claim 8, wherein Y3 represents repeat units of formula (III):

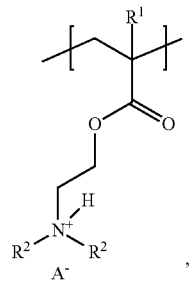

(III)

wherein:

$R^1$ is a hydrogen atom or methyl;

$R^2$ is the same or different $C_{1-6}$ alkyl; and $A^-$ is a carboxylate anion of an organic acid that is a plant hormone or a phosphorus solubilizer.

10. The fertilizer granule of claim 9, wherein the copolymers of formula (II) has the following ideal chemical structure:

POLY-004

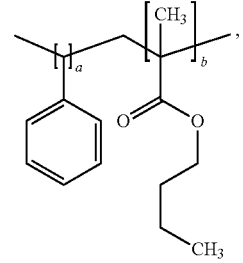

wherein a is about 50 wt % and b is about 50 wt %,

POLY-005/POLY-006

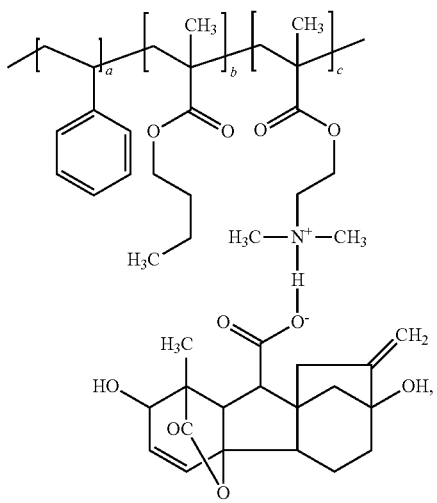

wherein a is about 44 wt %, b is about 47 wt %, and c is about 9 wt %, or wherein a is about 39 wt %, b is about 44 wt %, and c is about 17 wt %, -continued

POLY-007/POLY-008

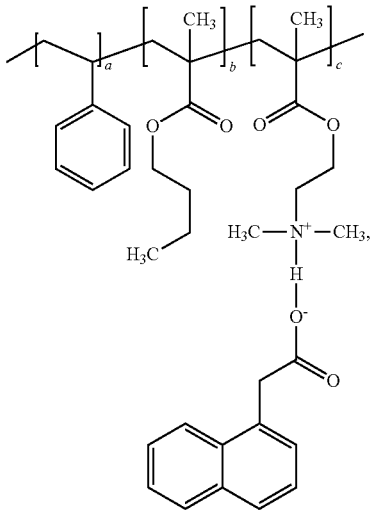

wherein a is about 46 wt %, b is about 48 wt %, and c is about 6 wt %, or wherein a is about 41 wt %, b is about 47 wt %, and c is about 12 wt %,

POLY-009

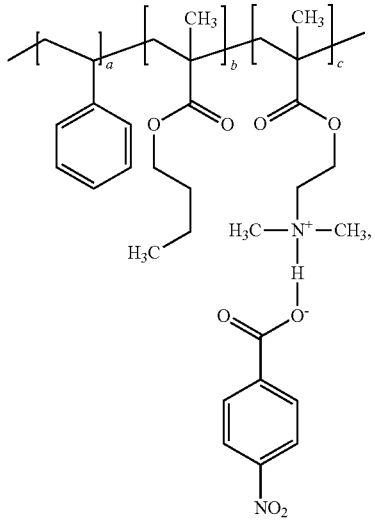

wherein a is about 46 wt %, b is about 48 wt %, and c is about 6 wt %,

-continued

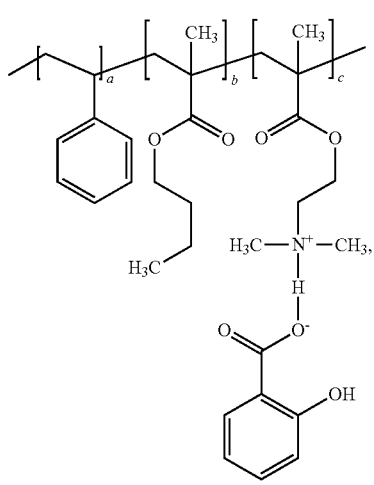

POLY-010 wherein a is about 46 wt %,
b is about 49 wt %, and c is about 5 wt %, or

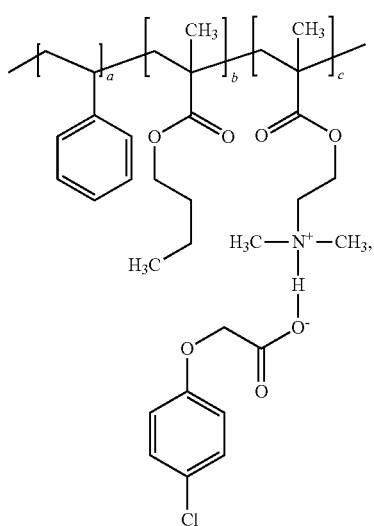

POLY-011 wherein a is about 46 wt %,
b is about 48 wt %, and c is about 6 wt %.

11. The fertilizer granule of claim 8, wherein Y3 represents repeat units of formula (IV):

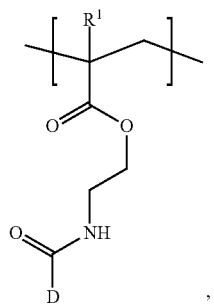

(IV)

wherein:

R$^1$ is a hydrogen atom or methyl;

D-C(=O)— is a residue of an organic acid that is a plant hormone or a phosphorus solubilizer.

12. The fertilizer granule of claim 11, wherein the copolymer of formula (II) has the following ideal chemical structures:

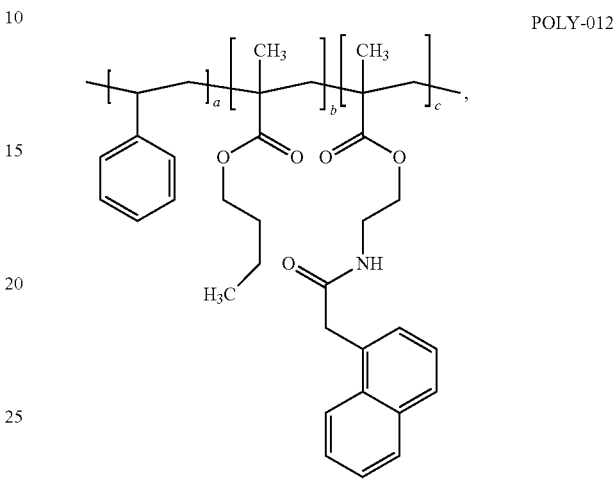

POLY-012 wherein a is about 47 wt%,
b is about 50 wt%, and c is about 3 wt%,

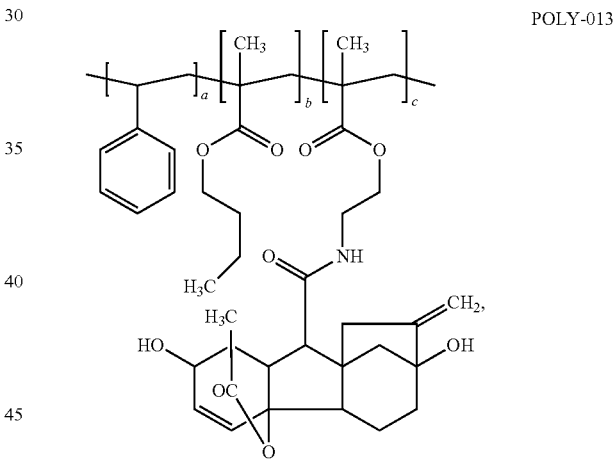

POLY-013 wherein a is about 47 wt%,
b is about 50 wt%, and c is about 3 wt%.

13. The fertilizer granule of claim 1, wherein the organic functional layer further comprises a water-swellable polymeric binder in the form of water-swellable copolymeric nanoparticles.

14. The fertilizer granule of claim 13, wherein the copolymer making the water-swellable copolymeric nanoparticles is of formula (I):

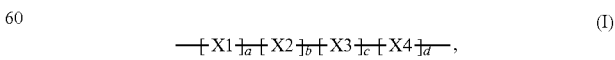

(I)

wherein:

X1 represents styrene repeat units;

X2 represents alkyl acrylate or alkyl methacrylate repeat units;

X3 represents alkoxy dialkyl vinylsilane, dialkoxy alkyl vinylsilane, or trialkoxy vinylsilane repeat units;

X4 represents acrylic acid, methacrylic acid, acrylamide, methacrylamide, vinyl phosphoric acid, or N,N-dimethylaminoethyl methacrylamide repeat units; and a, b, c and d represent the weight percent of repeat units X1, X2, X3, and X4, respectively, based on the total weight of the copolymer, and each vary between about 0.5 wt % and about 50 wt %, and wherein the X3 repeat units are optionally crosslinked with each other within the nanoparticles.

15. The fertilizer granule of claim 14, wherein some of the X3 repeat units are crosslinked with each other within the nanoparticles.

16. The fertilizer granule of claim 14, wherein the copolymer making the water-swellable copolymeric nanoparticles has the following ideal chemical structure:

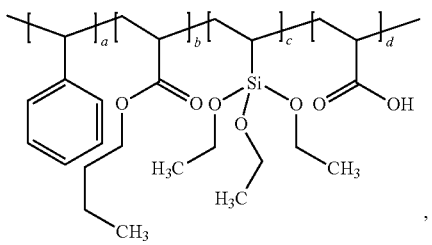

POLY-001

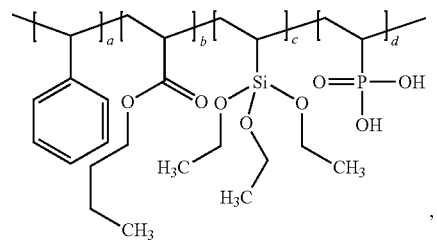

POLY-002

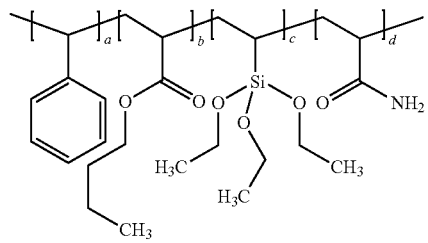

POLY-003 wherein a, b, c and d are about 48 wt %, about 48 wt %, about 3 wt % and about 1 wt %, respectively, based on the total weight of the copolymer.

17. The fertilizer granule of claim 1, wherein the microbial suppressor is a nitrification inhibitor, which is dicyandiamide, 2-chloro-6-(trichloromethyl)pyridine, 5-ethoxy-3-trichloromethyl-1,2,4-thiadiazole, 2-amino-3-chloro-6-methylpyridine, 2-mercaptobezothiazole, 2-sulfanimalamidothiazole, or a combination thereof.

18. The fertilizer granule of claim 1, wherein the phosphorus solubilizer is citric acid, lauric acid, alkyl sulfuric acid, wherein the alkyl group is a linear or branched alkyl chain with 4 to 24 carbon atoms, oxalic acid, or gluconic acid or a salt thereof.

19. The fertilizer granule of claim 1, wherein the plant hormone is abscisic acid; an auxin; a gibberellin; gluconic acid, salicylic acid; jasmonic acid; oxalic acid; citric acid; or pipecolic acid.

* * * * *